United States Patent [19]
O'Brien et al.

[11] Patent Number: 6,001,383
[45] Date of Patent: Dec. 14, 1999

[54] CYANOGEN FUMIGANTS AND METHODS OF FUMIGATION USING CYANOGEN

[75] Inventors: Ian G. O'Brien, deceased, late of Hawker, by Lorna Eileen O'Brien, legal representative; Frances James Michael Desmarchelier, Queanbeyan; Ren Yonglin, Lyneham, all of Australia

[73] Assignees: Commonwealth Scientific and Industrial Research Organisation, Parkview; University of Canberra, Bruce, both of Australia

[21] Appl. No.: 08/765,058
[22] PCT Filed: Jul. 5, 1995
[86] PCT No.: PCT/AU95/00409
  § 371 Date: Mar. 20, 1997
  § 102(e) Date: Mar. 20, 1997
[87] PCT Pub. No.: WO96/01051
  PCT Pub. Date: Jan. 18, 1996

[30] Foreign Application Priority Data

Jul. 5, 1994 [AU] Australia ............... PM 6669

[51] Int. Cl.$^6$ .................. A01N 25/00; A01N 59/24; A01N 37/34
[52] U.S. Cl. ............... 424/405; 424/607; 514/526
[58] Field of Search ............ 514/526; 424/607, 424/405

[56] References Cited

U.S. PATENT DOCUMENTS 3,535,076 10/1970 Fahnenstich et al. ............ 23/151

FOREIGN PATENT DOCUMENTS 197706 5/1923 United Kingdom .
237344 7/1925 United Kingdom .

OTHER PUBLICATIONS

The Merck Index, 10th Ed., Pub. 1983, p. 385, Entry 2686.

Primary Examiner—Jose G. Dees
Assistant Examiner—Alton Pryor
Attorney, Agent, or Firm—Sughrue, Mion, Zinn, Macpeak & Seas, PLLC

[57] ABSTRACT

A fumigant, comprising cyanogen ($C_2N_2$) provides a viable alternative to conventional fumigants such as methyl bromide, phosphine and carbonyl sulphide. Cyanogen ($C_2N_2$) can be used as such a fumigant in the control of a range of biota, including insects, mites, nematodes, fungi and their spores, viruses, spiders, bacteria, molds and rodents. It is also suitable for use on a variety of commodities, including grain, seeds, meats, fruit, vegetables, timber, plants, cut flowers and soil. It is shown that an efficacious concentration of cyanogen ($C_2N_2$) as a fumigant leaves a very low residue and can be readily flushed from commodities. In particular, it has been observed that a mixture of ($C_2N_2$) and carbon dioxide have a synergistic effect when applied to various biota. The term "cyanogen" is defined as the gas (as STP) cyanogen, ($C_2N_2$), essentially free from hydrogen cyanide and other cyanogenic compounds, (that is, compounds that give rise to hydrogen cyanide). Cyanogen, which has also been termed dicyan and oxalonitrile, as a fumigant, may be shown as $(CN)_2$, $C_2N_2$, or NC—CN.

15 Claims, 53 Drawing Sheets

Figure 37

CYANOGEN FUMIGANTS AND METHODS OF FUMIGATION USING CYANOGEN

TECHNICAL FIELD

This Appln is a 371 of PCT/AU95/00409 filed Jul. 5, 1995. This invention concerns fumigants. More particularly, it concerns fumigants as gas, or in solution which include the cyanogen ($C_2N_2$), and methods of fumigation using such gaseous and dissolved fumigants.

BACKGROUND TO THE INVENTION

Fumigants are widely used for the disinfestation, and protection against infestation, that is usually required to protect particulate commodities (such as grain) and other stored produce (including durable and perishable foodstuffs), porous bulk materials (for example, soil or timber) and spaces (typically, empty buildings). An ideal fumigant should be toxic to insects, mites, nematodes, bacteria, fungi and their spores, viruses and moulds and other pest biota. It should be effective in low concentrations. It should ideally have a low absorption by materials in the fumigated region. It should have a low mammalian chronic toxicity and leave either no residue or an inert residue. In addition, the ideal fumigant should present no difficulties as far as safe handling is concerned, and it should not adversely affect the commodity or space that is being fumigated.

No fumigant meets all of these "ideal" criteria. The two fumigants most commonly used in the fumigation of grain, other particulate materials, fruit and timer are phosphine and methyl bromide, although carbonyl sulphide has recently been proposed as an alternative to these fumigants (see the specification of International patent application No. PCT/AU93/00018, which is WIPO Publication No. 93/13659).

Phosphine is the preferred fumigant for grain stores and the like because it is effective against grain pest and leaves little residue (which is essentially a harmless phosphate). However, phosphine is spontaneously combustible when its concentration exceeds a relatively low value, and is unable to kill all stages of insects in a short period when used at acceptable concentrations.

Methyl bromide is more toxic to grain pests than phosphine when used for short periods of fumigation, but phosphine is more toxic to grain pests when long term fumigation is effected. Methyl bromide has a lower flammability than phosphine, but recent work has shown that methyl bromide depletes the ozone layer. Thus the use of methyl bromide as a fumigant is currently being phased out, following the Montreal protocol.

Carbonyl sulphide is currently undergoing extensive testing, and has not yet been approved for use as a fumigant, despite some clear advantages over both methyl bromide and phosphine. Other fumigants that have been used against grain pests include acrylonitrile, carbon disulphide, carbon tetrachloride, chloropicrin, ethylene dibromide, ethylene dichloride, ethylene oxide, hydrogen cyanide and sulphuryl fluoride. It will be noted that a halogen is present in many of these "conventional" fumigants, none of which has the "ideal" fumigant properties.

For many years, there has been a constant seeking of new fumigants and there is no doubt that the quest for improved fumigants will continue.

SUMMARY OF THE INVENTION

The present invention seeks to provide a new fumigant that has properties which make it a viable alternative to the conventional fumigants, particularly in the control of insects, mites, nematodes, fungi and their spores, bacteria, viruses, moulds and other pest biota.

In one broad form, the present invention provides a fumigant comprising cyanogen ($C_2N_2$) (as herein defined), in solution or in association with a carrier gas, wherein the concentration of cyanogen is in the range from 0.01 mg $L^{-1}$ to to about 160 mg $L^{-1}$.

Preferably, the carrier gas is an inert gas and also preferably the carrier gas has a low oxygen concentration.

In a preferred embodiment of the invention the carrier gas includes carbon dioxide.

According to a still further embodiment of the invention the fumigant is in solution, preferably an aqueous solution.

In a further broad form, the present invention provides a method of fumigation, comprising applying cyanogen ($C_2N_2$—as herein defined) in the gaseous form to a commodity and/or structure, wherein the concentration of cyanogen is in the range from 0.01 mg $L^{-1}$ to to about 160 mg $L^{-1}$, or applying cyanogen in an aqueous solution to a commodity and/or structure, such that the cyanogen concentration, if averaged over the volume of the enclosure and or structure, would be in the range from 0.01 mg $L^{-1}$ to to about 160 mg $L^{-1}$.

In a preferred form, said commodity includes grain, seed, meat, fruit, vegetables, timber, plants, cut flowers, and soil.

Preferably, said commodity includes, a silo, or like structure containing bulk grain (such as wheat) or the like, and a room, premises, appliance or the like, for dental, medical and/or veterinary applications.

In a preferred embodiment, said fumigant is able to control one or more of a range of biota, including viruses, insects, spiders, mites, nematodes, bacteria, moulds, fungi and their spores and rodents.

In another embodiment of the invention, said fumigant comprises, and/or is applied in an environment containing, carbon dioxide ($CO_2$).

Preferably, the humidity and/or pressure within an environment within which said fumigant is applied is adjusted to control the characteristics (e.g. increased toxicity and/or synergistic effects) of said fumigant.

In various preferred forms, said fumigation includes low flow gaseous fumigation, low pressure gaseous fumigation, high pressure gaseous fumigation, spraying of a fumigant as a gas, or in solution, and/or, soaking of a commodity in a fumigant as a gas, or in solution.

BRIEF DESCRIPTION OF THE DRAWINGS

The present invention will become more fully understood from the following detailed description of preferred but non-limiting embodiments thereof described hereinafter in connection with various examples outlining experimental procedures by the inventors, in connection with the accompanying drawings, wherein:

FIGS. 37 to 41 show the sorption of $C_2N_2$ by timber, compared with sorption of MeBr;

DETAILED DESCRIPTION OF PREFERRED EMBODIMENTS

Figure 1:
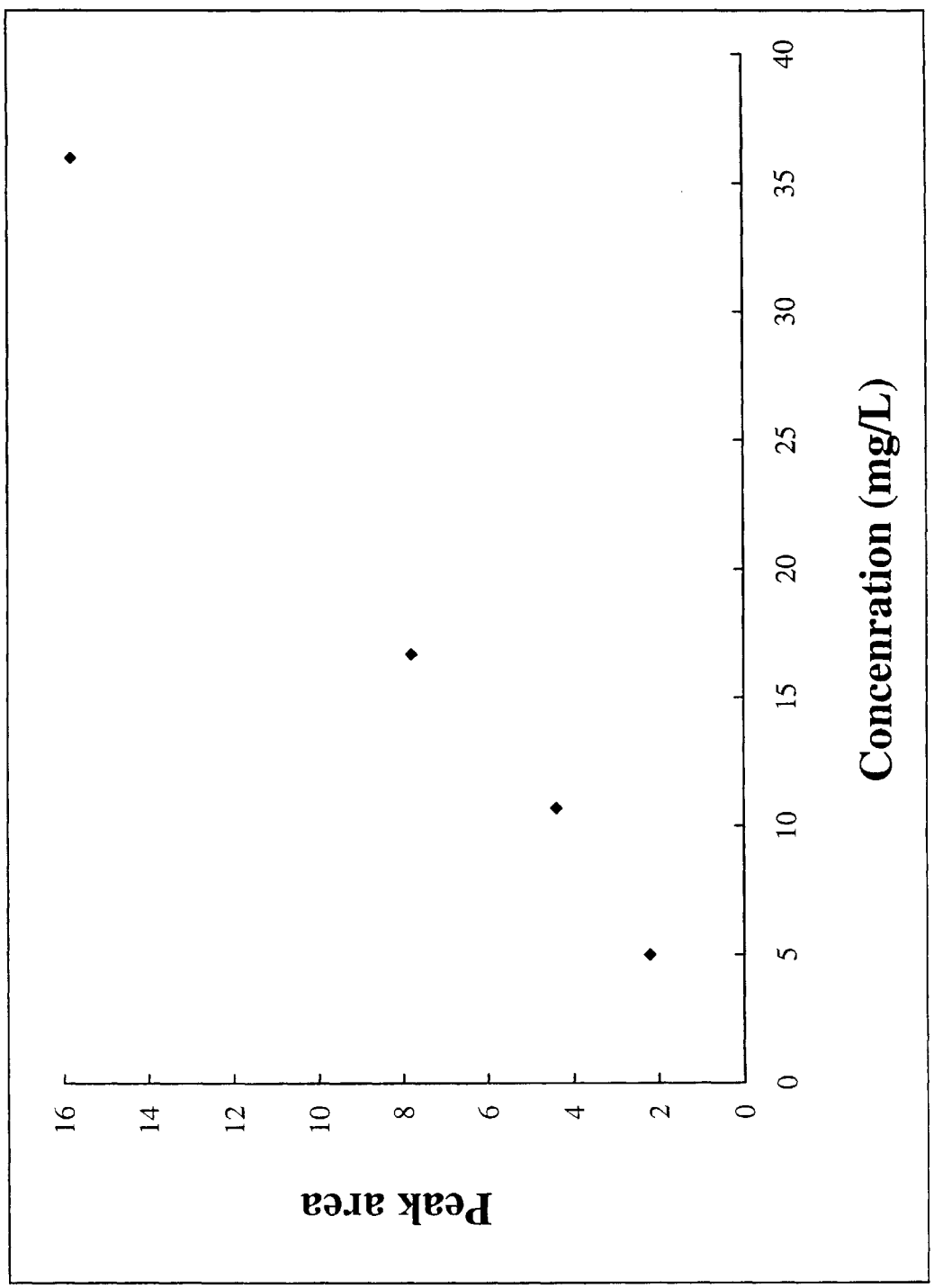
FIGS. 1 and 2 show graphical results of the analysis of $C_2N_2$ in the gaseous phase and in liquids.

It should be noted that in this specification and claims, when referring to the present invention, the term "cyanogen" is defined as a gas (when at STP) or a solution of cyanogen, $C_2N_2$, essentially free from hydrogen cyanide and other cyanogenic compounds (that is, compounds that give rise to hydrogen cyanide). Thus the cyanogen of the present invention is cyanogen as commercially prepared or purchased, without the presence of appreciable quantities of other chemicals, such as cyanogen chloride or hydrogen cyanide.

However, it is also possible that other chemical species which can liberate cyanogen can be utilized in place of, or in conjunction with cyanogen, in fumigation applications.

Cyanogen, which has also been termed dicyan and oxalonitrile, as a fumigant, may be shown as $(CN)_2$, $C_2N_2$, or NC—CN. Cyanogen occurs naturally in the atmosphere, being produced by plants and by the action of lightning. It is also present in other galaxies, and its spectral lines have been used in red-shift determinations to estimate the relative velocities of galaxies.

When reviewing the prior art, the present inventors were aware of a problem in the terminology used in older scientific papers and patent specifications. This problem is that, in the older scientific literature, any compound that is able to produce hydrogen cyanide (including those compounds which react with non-cyanogenic materials to produce hydrogen cyanide) was called a "cyanogen", whereas the compound that is called cyanogen today was termed "dicyanogen" or "dicyan". Any reviewer of the prior art in this field needs to be aware of this ambiguity of the older terminology.

Cyanogen has a substantial acute toxicity to humans and other warm-blooded animals but its chronic toxicity is insignificant (that is, small doses, ingested over a period of time, are not cumulative). In their paper entitled "The synthesis and chemistry of cyanogen", published in *Chemical Reviews*, Volume 59, pages 841 to 883, 1959, T K Brotherton and J W Lynn (referring to earlier work by A B Elkins) state:

"cyanogen is extremely poisonous, having a toxicity comparable to that of hydrogen cyanide. The maximum allowable vapor concentration is 10 parts per million."

In about 1913, J L Burckhardt, reporting the toxicity of cyanogen, concluded that (i) only doses of less than 0.1 mg of $(CN)_2$ per liter of air can be considered harmless for cats; (ii) 0.2 mg of $(CN)_2$ per liter is fatal to cats in a few hours; but (iii) rabbits can tolerate 0.4 mg per liter well, their fatal dose being between 0.6 and 0.8 mg of $(CN)_2$ per liter.

In the U.S. Pat. No. 1,399,829, dated Dec. 13, 1921, J W Van Meter states that cyanogen, chlorine and arsenical gases "have all been used separately with more or less success as fumigating agents, germicides, disinfectants, deodorizers and for the extermination of insects and animals". However, Van Meter provided no support for this statement, and the present inventors have located no prior reference (or a more recent reference) that would show the veracity of Van Meter's statement. Van Meter does state in the specification of U.S. Pat. No. 1,399,829 that "Cyanogen gas is a deadly poison to aphis and larva affecting citrus and other orchard trees . . . it is not injurious to the foliage . . . ". His invention, in fact, was a "combination or mixture of the above named gases". Although Van Meter asserted that he was able to pass a limited amount of chlorine through a potassium cyanide solution containing iron "to liberate the cyanogen", he observed that this gas is "lighter than air", showing that, in fact, he had produced a gas which was rich in hydrogen cyanide, for cyanogen is denser than air.

British patent No. 237,344, dated Apr. 24, 1924, is entitled "Cyanogen fumigants". The specification of that patent describes the use of hydrogen cyanide (HCN) and other cyanide derivatives, distributed over kieselguhr or other porous carriers, with sulphuric acid or oxalic acid added to prevent decomposition of the cyanides. Cyanogen itself, however, is not included in the "cyanogen fumigants" listed in the specification of UK patent No. 237,344.

It is also noted that in the aforementioned paper by T K Brotherton and J W Lynn, there is no reference to a fumigant potential for cyanogen.

Despite extensive investigation of the prior art, the present inventors have discovered no prior example of the use of cyanogen as a fumigant. It is believed that cyanogen's properties in regard to stability (it has been asserted that $C_2N_2$ decomposes readily in the presence of water) and toxicity has led to a belief that cyanogen is inherently unsuitable for use as a fumigant.

The present inventors have ascertained that this belief is unfounded, and that cyanogen, provided it is handled with due care, can be used in gases and solutions to provide fumigants which have significant advantages over currently preferred fumigants. In particular, (a) cyanogen can be mixed with other gases for gaseous fumigation, and if the fumigant carrier is air or other oxygen-rich gas, there is no risk of explosion provided the concentration of $C_2N_2$ is less than 6.6 percent, and even at concentrations of higher than 6.6 percent, a spark or flame is required to cause ignition of the oxygen/cyanogen mixture;

(b) cyanogen is soluble in water (and other solutions) and can be applied to a commodity or to a structure in low aqueous concentration by spraying or simply by pouring the solution on to the commodity or structure;

(c) while cyanogen is absorbed quite readily into grain, other particulates or stored foodstuffs, it can ideally be used for rapid fumigation of bulk grain and the like either by use of cyanogen as gas with a significant level of $CO_2$ (which reduces absorption) as carrier or use of a high concentration cyanogen fumigant either sprayed or passed through the grain at a rapid flow rate;

(d) it has been shown that fumigation of wheat and other seeds using an efficacious concentration of cyanogen for the fumigation has no effect on the germination rate of the wheat or other seeds (but it should be noted that when the concentration of cyanogen is 180 mg per liter or higher, the fumigant-containing gas acts as a herbicide, which can inhibit germination of some seeds);

(e) cyanogen leaves a very low residue on commodities as it is rapidly degraded with conversion to cyanide not the dominant pathway, in contrast to experience with the use of fumigants which contain hydrogen cyanide, which leave significant residues;

(f) cyanogen can be flushed from a particulate commodity at the end of a period of fumigation by passing an airstream through the particulate commodity;

(g) cyanogen can be removed from an airstream simply by cooling the airstream to a temperature below the liquefaction point of cyanogen (which is −21.17° C. at STP);

(h) cyanogen is able to control a range of biota, including insects, mites, fungi and their spores, bacteria, viruses and rodents;

(i) fumigation with cyanogen-containing fumigants enables long term storage of high moisture grain without spoilage;

(j) cyanogen is systemic in plants, and thus can be used systemically to control insects and plant diseases;

(k) cyanogen is active in both aqueous solution and as a gas, and is able to move through water, thus enabling control of bacteria, fungi and viruses in a range of situations such as those found in medical, dental, scientific and veterinary premises and the apparatus used in these applications; and, (l) cyanogen is useful in the preservation of meat and of fruit and vegetables.

The present inventors have also discovered that a mixture of cyanogen and carbon dioxide enhances the toxicity of cyanogen. There is currently no explanation for this observed synergistic effect of mixing cyanogen with carbon dioxide. However, the present inventors have hypothesised that the carbon dioxide increases the respiration rate of insects, and other biota and this would increase the rate at which the cyanogen enters the pests respiratory systems. This is, however, merely an unsubstantiated hypothesis and may or may not be responsible for the observed synergistic effect.

Thus, according to the present invention, there is provided a fumigant which comprises cyanogen and a carrier gas, the concentration of cyanogen being generally in the range of from 0.01 mg $L^{-1}$ to 160 mg $L^{-1}$.

The carrier gas may be an inert gas. The carrier gas will conveniently have a low oxygen concentration (for example, burner gas). Preferably, the carrier gas contains carbon dioxide.

Also according to the present invention, there is provided a fumigating liquid comprising cyanogen in an aqueous (or other liquid) solution.

The present invention also encompasses a method of fumigation which comprises: applying a gaseous fumigant or a fumigant in solution in accordance with the present invention to a commodity for the required period of fumigation.

The method of fumigation of this invention includes low flow gaseous fumigation, low pressure gaseous fumigation, high pressure gaseous fumigation, spraying of a fumigant in solution, and soaking of a commodity in a fumigant in solution. This list is not exhaustive.

With low flow fumigation, air or other carrier gas containing a predetermined concentration of cyanogen is passed slowly through a particulate commodity, in a manner similar to the phosphine fumigation method that is described in the specifications of International patent applications Nos PCT/AU90/00268 and PCT/AU94/00324. The concentration of cyanogen in the fumigant-containing gas depends on sorption and time exposure but will preferably be in the range of from about 0.01 mg $L^{-1}$ to about 5 mg $L^{-1}$. As also noted above, the preferred carrier gas contains carbon dioxide, because the enhanced toxicity of the combination of cyanogen and carbon dioxide enables a lower concentration of cyanogen to be used, without sacrificing the efficacy of the fumigation.

Low pressure fumigation of a stored commodity can be effected with a gaseous cyanogen fumigant when the commodity is stored in an essentially gas-tight chamber. The chamber is evacuated, or substantially evacuated, then the cyanogen-containing gas is introduced into the chamber. This technique ensures that the cyanogen-containing gas is distributed throughout the chamber, thus establishing a predetermined fumigation regime (based on toxicological considerations) for the entire stored commodity. The inventors have determined that in low pressure fumigation, the fumigant can achieve the same toxic endpoint as if it were present at STP (although exposure time may need to be varied), thus minimising the amount of fumigant required to achieve a toxic effect.

High pressure fumigation of a stored commodity is also possible when the commodity is stored in an essentially gas-tight chamber. After the optional step of evacuating the chamber, the cyanogen-containing gas (preferably including carbon dioxide) is introduced into the chamber until a predetermined over-pressure of the gas in the chamber has been established. If the chamber is then sealed, fumigation of the commodity will be maintained until the chamber is opened and the cyanogen-containing gas is flushed from the chamber.

Insect pests in a stored commodity may be killed more quickly with high pressure fumigation than when low-flow or low-pressure gaseous fumigation is used. Since the additional equipment required to establish high pressure fumigation makes this technique were mostly to perform, it will be used mainly for the rapid disinfestation of high value commodities.

In each of the gaseous fumigation techniques described above, it is possible to trap the cyanogen that has been used for the fumigation either by cooling the fumigant-containing gas that leaves the vessel or chamber in which the fumigated commodity is stored, or by chemical degradation or absorption of the cyanogen (which includes passing the cyanogen-containing gas through a chemical—for example, an amine or an absorbent.

The solubility of cyanogen in water and a selection of other liquids is given in Table 2 of the aforementioned paper by Brotherton and Lynn. Liquid fumigation of commodities, as noted above, can be effected by spraying the commodity with a liquid (usually water) containing cyanogen in a pre-determined low concentration (chosen in accordance with toxicological considerations). Alternatively, the cyanogen-containing liquid can be poured onto the commodity to cover it or to trickle through it. The contact with the liquid fumigant is maintained by constant or intermittent (but periodic) application of the liquid fumigant to the commodity, thus maintaining the fumigation of the commodity for any required period. At the end of the fumigation period, the cyanogen-containing liquid can be removed from the commodity by (a) washing with water, followed (if necessary) by drying with a clean airstream, or (b) by flushing the commodity with a clean airstream, which takes up both the carrier liquid and the cyanogen of the liquid fumigant.

Cyanogen is commercially available in cylinders of compressed $C_2N_2$. Such cylinders of cyanogen can be used as the source of cyanogen for the gaseous and liquid fumigants of, or used in, the present invention. However, on-site generators of cyanogen may be used, instead of commercial cylinders of the gas, as the source of cyanogen. Examples of on-site generators include (i) those which subject a mixture of nitrogen and carbon dioxide to a carbon arc discharge, optionally with recycling the unreacted $N_2$ and $CO_2$; and (ii) those in which a carbon filament is heated to about 2,200° C. in an atmosphere of nitrogen. Other alternative sources of cyanogen include gas cylinders containing a compressed mixture of cyanogen and carbon dioxide and/or a low oxygen atmosphere, and sorbent materials which contain a cyanogen that can be released when required.

EXAMPLES

The inventors of the present invention have conducted numerous experiments to demonstrate the efficacy of cyanogen ($C_2N_2$) as a fumigant. A number of these experiments are detailed in the following Examples.

Example 1

Analysis of $C_2N_2$ in the Gaseous Phase and in Liquids

Aim. The air was to determine $C_2N_2$ concentrations in air.
Materials and Methods $C_2N_2$ was determined by gas-liquid chromatography, on a Varian 3300 gas chromatograph, equipped with a thermionic specific detector, selective for nitrogen and phosphorus. Columns used were megabore columns, of internal diameter 0.53 mm; either DBwax (J & W 127-7012) at an isothermal temperature of 60° C. or BP624 (SGE, 50QC5/BP624, at an isothermal temperature of 110° C.

Methodology for samples in air

Standards of gas, determined from a Gow-Mac gas density balance, were diluted by injecting known volumes into 120 mL flasks, fitted with a Mininert valve, and containing two glass beads. After mixing by shaking the flask and leaving for 1 h, aliquots (20 µL) were injected into the gas chromatograph. The response was recorded and plotted against the applied concentrations.

Methodology for samples in water, and other solvents

Water (10 mL) was pipetted into Erlenmeyer flasks of known capacity (typically 11.5 mL), which were then fitted with a Mininert valve. Known quantities of gas were injected, with an air tight syringe, into the water. The flask was allowed to stand for 1 h at 25° C. Aliquots of the liquid (1 µL) and of the headspace gas (20 µL) were injected into the gas chromatograph. The response was recorded and plotted against added concentrations.

Results

A plot of peak area (arbitrary units) versus concentration of $C_2N_2$ is shown in FIG. 1, for the case of 30 µL injections and the DBwax column. The curve is linear over the range 0–35 $mgL^{-1}$, but extrapolation of the curve to higher concentrations underestimates the response. The signal to noise ratio at 20 $µgL^{-1}$ (approximately 10 ppm, V/V) was 240. Thus the method is sufficiently sensitive to detect below the TLV value of 10 ppm, V/V (Sax and Lewis, 1989).

Figure 2:
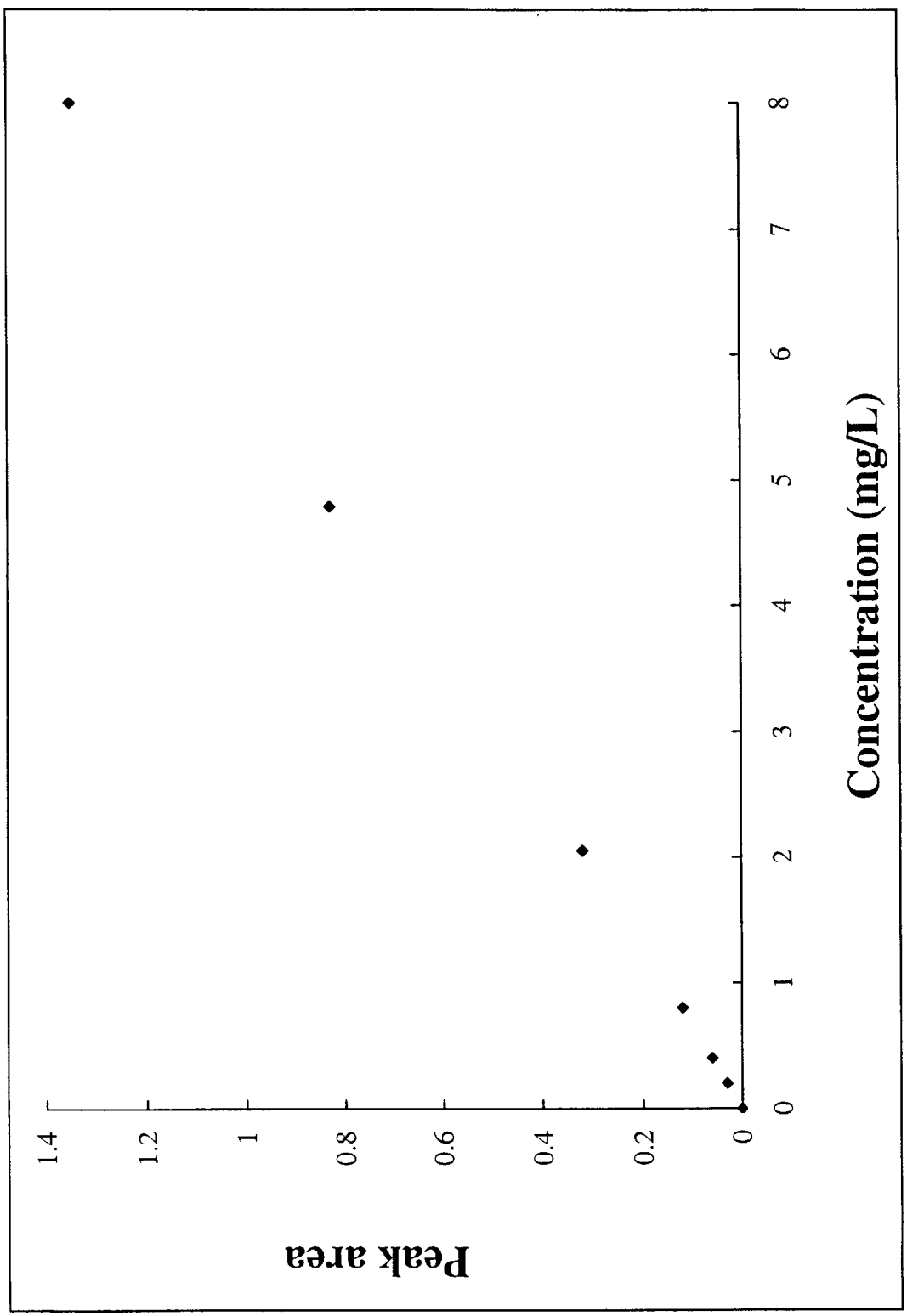

Aqueous solutions of $C_2N_2$ also produced a linear response in the region tested. 0–8 $mgL^{-1}$, for the case of 1 µL injections onto DBwax (FIG. 2). In this situation, the water chromatographed after the fumigant.

Summary

Measurement of $C_2N_2$, either in water or in air, presents no particular difficulties, and it is possible to measure well below the TLV value.

Example 2

Efficacy of $C_2N_2$ in Mixtures of Air and Carbon Dioxide

Aim: to determine whether $C_2N_2$ is effective in mixtures containing carbon dioxide, and whether carbon dioxide potentiates $C_2N_2$.

Materials and Methods

A mixture of carbon dioxide (40% V/V) and air was made up in a Tedlar bag, and water (10 µL) added to compensate for the aridity of the carbon dioxide source. Insects were connected to this source in Dreschel bottles, and the fumigation performed as discussed under the flow-through technique.

In other experiments, 270 mL erlenmeyer flasks were flushed with 40% carbon dioxide in air. The apparatus consisted of a quickfit connection, with a tap inlet for the carbon dioxide air mix, and a glass outlet. After flushing, the tap was closed and the gas outlet was fitted with a septum for injection of the fumigant $C_2N_2$ and for sampling for analysis of the fumigant. Moist filter paper was added to the side of the flasks. Assays were also conducted in flasks with air, without added carbon dioxide. All bioassay procedures of dosing, temperature and interval between dosing and assessment of mortality were identical, with the only difference being the proportion of carbon dioxide in the atmosphere of the fumigation chamber.

The test insect was adult *Rhyzopertha dominica* (F.), strain CRD2.

Fumigant concentrations were determined on a Varian 3300 Gas Chromatograph, equipped with a Thermionic Specific detector, after separation on a DBwax column, of internal diameter 0.53 mm.

Results

In the flow through experiments, exposure for 1 h to $C_2N_2$, at 0.83 $mgL^{-1}$, achieved 100% mortality, both as assessed at the end of exposure and after a recovery period of 1 weeks. However, at lower doses apparent acute mortality was less than that 1 week later. Exposure for 45 min. resulted in a mortality of 5.4%.

In the static experiments, mortality after a holding period of 48 h, after a 23 h exposure to 0.125 $mgL^{-1}$, was 97%, in the case of $CO_2$, versus 1%, in the case of air. For a 2 h exposure to 0.5 $mgL^{-1}$, mortality was 80%, in the case of $CO_2$, versus 2.5%, in the case of air. In all cases, some insects, after a recovery period of 48 h, were affected, and mortality after 2 weeks may be higher.

Discussion $C_2N_2$ can be applied in $CO_2$, either in a flow through manner or under static conditions. Synergism with $CO_2$ has been demonstrated. Co-application with $CO_2$ has potential uses, eg in method of storing in cylinders, in helping to mix in silos, in reducing fire hazard, and in controlling the pH of water, in conditions were bacteria or moulds may be present in water.

Synergism from $CO_2$ at increased pressure is shown in Example 45.

Example 3

Analysis of Residues of $C_2N_2$ by Sampling the Headspace over Ground Grain Aim: to determine residues of $C_2N_2$ in fumigated wheat by a standard procedure and to ascertain the amount of fumigant likely to be released during milling of wheat.
Materials and Methods Australian standard white wheat was deliberately fumigated with a high dose of fumigant by adding 5 mL of fumigant to 25 g of wheat in a 120 mL container, sealed with a Mininert valve. The initial calculated headspace concentration was 4%, V/V (40,000 ppm, V/V), and the fumigant was applied at the rate of 420 g/g (420 ppm, W/W). After storage for 10 days at 30° C. in a sealed container, wheat (20 g) was immediately transferred to a sealed blender, and ground for 20 sec. The headspace gas (50 µL) was injected into a Varian 3300 Gas Chromatograph, equipped with a thermionic specific detector, and separated on a DBwax column, of internal diameter 0.53 mm. The response was compared with that of hydrogen cyanide and $C_2N_2$.

Results

Two peaks were observed on the chromatograph of the headspace from both fumigated and control wheat, but neither was $C_2N_2$. The limits of detection were such that the residues in wheat were less than $6\times10^{-11}$ g/g on the grain.

One of the peaks co-chromatographed with hydrogen cyanide. Levels corresponded to, on average, $5\times10^{-8}$ g/g in control wheat and $5.6\times10^{-8}$ g/g in fumigated wheat. The difference between these two values was not significant.

The peak that chomatographed before $C_2N_2$ was not identified, other that to demonstrate that it had a shorter retention time than phosphine. An educated guess is that this peak is cyanic acid. If so, and assuming the same response to the detector as hydrogen cyanide, residues in both the control and fumigated wheat were between $2\times10^{-8}$ g/g and $3\times10^{-8}$ g/g.

Discussion

The method used to test grain for residues of fumigant is widely used; the results correspond to those reported in Example 26. That is, $C_2N_2$ is rapidly broken down on wheat in sealed containers. A residue less than $6\times10^{-11}$ g/g from an application of 420 g/g represents an enormous loss, and this level of loss has never previously been demonstrated for any insecticide applied to grain.

The concentration of both $C_2N_2$ and of hydrogen cyanide in a sealed container, above ground grain was considerably less, in each case, than the TLV value of 10 ppm. V/V, despite the very large amount of $C_2N_2$ applied. Thus flour millers will not be exposed to unlawful levels of fumigant during the milling of wheat previously fumigated with $C_2N_2$ (subject to withholding periods to be determined by regulatory authorities).

Example 4

The efficacy of $C_2N_2$ in Mould Control

Aim: to determine the efficacy of $C_2N_2$ against moulds.

Materials and Methods

Wet wheat

Wheat was conditioned to 30% moisture content, W/W and placed in 270 mL flasks, with 30 g of wheat per flask. Flasks, equipped with a septum inlet, were stored at 30° C. $C_2N_2$ was applied to flasks at doses of 0, 20, 40 and 80 $mgL^{-1}$. After 24 h, the wheat was removed from flasks and placed in sterile jars, which were covered with filter paper. Each experiment was replicated four times.

Moulds present in the wheat were identified by Dr. Ailsa Hocking, CSIRO Division of Food Science and Technology. The % infection of grains was 78% by *Alternaria infectoria*, 17% by *Alternaria alternata*, 4% by *Epicoccum nigrum* and 1% each by Dreschlera sp., Fusarium sp. and Penicillium sp.

Dry wheat

Wheat of 11.6% moisture content was fumigated as described in the previous section. After fumigation for 24 h, wheat was placed on nutrient Agar, and incubated at 25° C. for 7 days.

Results

Wet wheat

Wheat in the control jars rapidly became mouldy, and the individual grains coalesced into solid lumps. No visible mould was detected in any of the fumigated commodities. Fumigated grain was kept for 4 weeks at 30° C. without any appearance of mould.

Dry wheat

The wheat did not become mouldy. On plating on nutrient Agar, the control wheat became mouldy, but no moulds were observed at doses of 20,40 and 80 $mgL^{-1}$. Mould growth from the dosage at 10 $mgL^{-1}$ was observed, but it was less than in the control. The moulds observed in the control wheat were Alternaria sp. and Penicillium sp., which were present before the fumigation, and were thus not artefacts of the procedure.

Discussion

Reference is made to Example 21. This Example and Example 21 are essentially replicates, by different scientists. These results, coupled with completely independent results from Example 21, indicates that $C_2N_2$ is highly effective in controlling moulds. The long period of protection given by this fumigant indicates that it kills spores, and is not merely fungistatic.

The potential use of $C_2N_2$ for mould control is considerable. For example, it can be used as an alternative to drying in situations where the grain is wet, or it can be used to hold grain for certain periods to extend the useful period of driers. The use of $C_2N_2$ for mould control reduces germination, and it is not proposed for all purposes. However, currently the fungistat propionic acid is widely used to control moulds on grain for animal feed. $C_2N_2$ would have potential use in such situations.

The ability of $C_2N_2$ to be applied as a solution, as well as a gas, has many potential applications for mould control eg for disinfesting machinery in food premises and, indeed, in disinfesting the premises themselves.

Moulds were controlled on both dry and wet wheat. Normally one would rely on the aridity to contain molds on dry grain; however, in some situations areas prone to moisture migration, such as the tops of silos, could be fumigated to kill mould spores, as a preventative measure. The ability to kill mould spores at both high and low humidities is useful in disinfestation of moulds in buildings and machinery, etc.

The moulds controlled included major genera such as Alternaria, Fusarium, Penicillium, Dreshslera and Coelomycete.

For purposes of disinfestation of moulds in machinery and buildings, the ability of $C_2N_2$ to act in both the vapour and liquid phase, and to penetrate water, is extremely useful as is its ability to control bacteria and insects. Thus it is a general sterilisation agent. In contrast, ethylene oxide is poorly soluble in water and formaldehyde has a low vapour pressure. In addition, each of ethylene oxide and formaldehyde is a suspect carcinogen (Sax and Lewis, 1989). The TLV value for ethylene oxide is 0.1 ppm; that for formaldehyde is "1 ppm: suspected carconogen" (ACGIH). The TLV value for $C_2N_2$ is 10 ppm.

Example 5

Efficacy of $C_2N_2$ in Preserving Meat Quality

Aim: to determine the efficacy of $C_2N_2$ in preservation of meat.

Materials and Methods

Fresh (unfrozen) meat was purchased at local supermarkets and sliced. Slices, e.g. approximately 20 g of lamb liver, was placed in 750 mL jars, equipped with septum lids. $C_2N_2$ was applied to give concentrations of 0, 20, 40 and 80 $mg.L^{-1}$. The jars were stored at 37° C. for 48 h, and for further periods at 30° C.

Results

The control liver rapidly lost colour, and became putrid and smelly in a space of hours. No visible effect was observed in any of the fumigated liver for a period of 48 h. A change in colour was observed starting at 2 days for the fumigation with 20 $mgL^{-1}$, and 3 days for the fumigation at 80 $mgL^{-1}$. No effect was observed 8 days after fumigation with the highest tested dose.

Discussion

The ability of $C_2N_2$ to control bacteria, moulds and insects at high humidities, and to rapidly decay, are desirable attributes for meat preservation. The potential for meat preservation is considerable. For example, meat can be sterilised inside plastic bags, glass containers or in larger containers, and bacterial contaminants can be destroyed. Potential uses are in wholesale and retail meat premises, and for uses where refrigeration is not available (eg military, campers).
Cross references
Cross reference is made to Examples 4, 21, 19, 28, 16 and 6.

Example 6

Efficacy of $C_2N_2$ in Preservation of Fruit Quality

Aim: to determine the efficacy of $C_2N_2$ in preservation of fruit and vegetables.
Materials and Methods Kiwi fruit, mandarins and mushrooms were tested. Two of each commodity were placed in 750 mL glass containers, equipped with a septum lid, with separate jars for each commodity. Fumigant was injected into each container to give concentrations of 0, 10, 20, 40 and 80 mgL$^{-1}$. Commodities were kept at 37° C. for 8 d. Commodities were removed, and quality assessed by visual inspection at time of opening and after a further 2 days storage at 25° C. Each treatment was duplicated.
Results The untreated (control) Kiwi fruit became soft. At 8 and 10 days, the colour had changed to a mixture of green and yellow, the fruit was very soft, and free water had escaped from inside the fruit. The fruit fumigated at 10 and 20 mgL$^{-1}$ exhibited some of these changes, but to a lessened extent. The fruit fumigated at 40 mgL$^{-1}$ retained its original colour and consistency. However, the fruit fumigated at the highest dose showed some signs of browning.

The treated fruit, at each dose, remained firm. There was no other observed effect on quality.

The unfumigated mandarins became mouldy. After 8 and 10 days, the mandarin flesh had become very soft, and it was difficult to separate the segments from the skin, or from other segments. No mould was observed on the mandarins fumigated at the two highest doses, and quality of the mandarins fumigated at the two lower doses was better than that in the control. However, the skin colour was altered in all treatments, although the flesh colour was not affected. The least effect on skin colour occurred at the dose of 40 mgL$^{-1}$.

The unfumigated mushroom also became mouldy. After 8 and 10 days, it was difficult to recognise the dark remnants as once having been mushrooms. Mushrooms fumigated at 10 mgL$^{-1}$ resembled the control, after 8 days. Those fumigated at 20 mgL$^{-1}$ retained their original shape, but free water was lost from the mushrooms. Those fumigated at either of the two higher doses retained their shape and colour, including the white colour at the top of the mushrooms. No visible mould was observed on the treated mushrooms after fumigation at 40 or 80 mgL$^{-1}$, though the mushrooms lost some free water.
Discussion Fruit and vegetable quality can deteriorate through moulds and bacteria, as well as through insect attack. In other Examples, it has been shown that $C_2N_2$ is effective against moulds, bacteria and insects, and can be effective at the high humidities found in storage of fruit and vegetables. In addition, a principal metabolite of $C_2N_2$ is oxalic acid, which is widely present in the plant kingdom.

The results indicate the potential for $C_2N_2$ in preservation of fruit and vegetables.

The use of $C_2N_2$ to preserve fruit and vegetables requires appropriate control of the dose, and both low doses and excessive doses can cause harm.

The potential is enormous, and includes packaged fruit in retain and wholesale premises, fumigation of fruit prior to shipment, and packaging for purposes where refrigerated is not possible (eg for camping, for the armed forces, etc).
Cross reference The reader is referred to Examples 19, 4, 21, 28, 35 and 15.

Example 7

Toxicity of $C_2N_2$ to Whitefringed Weevil in Soil, and Sorption in Soil

Aim: to determine the efficacy of $C_2N_2$ as a soil fumigant, to measure its sorption in soil and to test whether it would be effective when applied as a gas and in aqueous solution.
Materials and Methods The species tested was whitefringed weevil, *Graphognatus leucoloma* (Boheman), which is a serious soil pest of pastures and of crops such as potatoes. Soils tested were from West Australia, where *G. leucolama* is a major pest. Soil samples and insects were provided by John Mathiesson, of the CSIRO Division of Entomology.

Tests without soil

For tests against the insect, 50 first-instar larvae were placed in Erlenmeyer flasks (138.5 mL capacity), equipped with a septum inlet. The fumigant was applied as a gas, and the flasks were kept 24 h at 20° C. The flasks were then unstoppered, and mortality assessed after leaving overnight. The procedure was identical to that used to assess other fumigants, including methyl bromide and carbon bisulphide (Mathiesson, Desmarchelier, Vu and Shackleton, unpublished results).

Concentrations of $C_2N_2$ were determined on a Varian 3300 Gas Chromatograph, equipped with a thermionic specific detector, after separation on a DBwax column, of internal diameter 0.53 mm. Concentrations were determined 1 h after injection and 1 h before removing the stopper, and the mean concentration is recorded in the tables. On average, the concentration declined by 12% over the measurement period of approximately 22 h.

Test in soil

In tests on soil, 50 first-instar larvae were added to soil, which was placed in sealed flasks. The fumigant was applied either as a gas or in aqueous solution. After an exposure period of 24 h, during which the fumigant was measured, the flask was aired overnight. The number of live and dead larvae were counted under a microscope, after flotation of the larvae in water, and mortality in fumigated soil was compared with that in the control. Insects able to move were classified as live.

a. fumigant applied in water

For tests against the insect in soil, flasks of capacity 138.5 mL were approximately half filled with soil (30 g). First-instar larvae (50) were added to each jar. The fumigant was applied in an aqueous solution (2 mL or 4 mL).

b. fumigant applied as a gas

The fumigant was applied as a gas to flasks with the same filling ratio as those used for the fumigant applied in water. The flasks were of capacity 29.5 mL, and fitted with a Mininert valve. Three types of soil were used (6.4 g), namely Pemberton loam, Sadie peat and Myaluys sand.
Results Toxicity in chambers free of soils Toxicity of the fumigant, applied as a gas to insects in erlenmeyer flasks without soil, is outlined in Table 1. Complete (100%) mortality was obtained for average concentrations greater than, or equal to, 1.5 mgL$^{-1}$. Below that level, mortality declined. Mortality was 56% at an average concentration of 0.59 mgL$^{-1}$. The concentration by time product to kill 95% of the larvae is approximately 26 mg.h. L$^{-1}$, which is slightly below the figure for methyl bromide recorded in comparable tests (Mathiesson, Schackelton, Vu and Desmarchelier, unpublished results). $C_2N_2$ is considerably more toxic to *G. leucoloma* than carbon bisulphide, which is also a fumigant widely used in soil fumigation.

Toxicity in soil, for the fumigant applied in water

Mortality of first instar larvae, after fumigation with $C_2N_2$ in soil, is shown in Table 2, together with the amount applied and the concentration of $C_2N_2$ in the headspace approximately 23 h after addition of fumigant. Complete mortality was obtained.

Toxicity in soil, for the fumigant added as a gas

Toxicity for the fumigant added in a gas is shown in Table 3. For the Pemberton loam, mortality was 100% and the headspace concentration of $C_2N_2$, 23 h after application, averaged 1.11 $mgL^{-1}$. For the Myaluys sand, mortality was 99%, and the headspace concentration, 23 h after application, averaged 0.89 $mgL^{-1}$. Mortality was zero on the peat soil, and no fumigant was detected 23 h after application.

Discussion

The fumigant $C_2N_2$ proved effective against a major pest in soil. It was effective in soil, whether applied as a gas or in aqueous solution.

The ability to apply $C_2N_2$ in soil is important because soil fumigation with methyl bromide is a major cause of release of this gas into the atmosphere.

TABLE 1

Toxicity of $C_2N_2$ to *G. leucolama* for a 24th exposure at 20° C.

| Average concentration (mg.L$^{-1}$) | Mortality |
|---|---|
| 5.1 | 50/50; 50/50 |
| 2.3 | 50/50; 50/50 |
| 1.5 | 50/50; 50/50 |
| 1.27 | 49/49; 48/49 |
| 0.99 | 40/50; 39/49 |
| 0.59 | 31/50; 25/51 |
| 0 | 0/50; 0/50 |

TABLE 2

Toxicity of $C_2N_2$ to *G. leucolama* in soil (30g) in a sealed flask (138.5 mL) at 20° C. The fumigant was applied in water to insects in Pemberton loam soil.

| Amount applied (mg) | Concentration in air at 23h (mg.L$^{-1}$) | Method of application | Number recovered | |
|---|---|---|---|---|
| | | | live | dead |
| 0 | 0 | wet | 38 | 0 |
| 1.85 | 0.93 | wet | 0 | 44 |
| 1.85 | 0.85 | wet | 0 | 46 |
| 3.7 | 3.49 | wet | 0 | 32 |
| 3.7 | 3.08 | wet | 0 | 48 |

TABLE 3

Toxicity of $C_2N_2$ to *G. leucolama* in soil (6.4 g) in a microflask equipped with mininert valve (29.5 mL) at 20° C. The fumigant was applied as a gas to insects in Sadie Peat (S), Pemberton loam (P) and Myaluys sand (M) soils

| Soils | Amount applied (mg) | Concentration in air at 23h (mgl$^{-1}$) | Method of application | Number recovered | |
|---|---|---|---|---|---|
| | | | | live | dead |
| M | 0 | 0 | dry | 47 | 4 |
| | 0.34 | 0.085 | dry | 1 | 46 |
| | 0.34 | 0.09 | dry | 0 | 51 |
| P | 0 | 0 | dry | 44 | 6 |
| | 0.34 | 1.05 | dry | 0 | 50 |
| | 0.34 | 1.17 | dry | 0 | 50 |
| S | 0 | 0 | dry | 43 | 2 |
| | 0.34 | 0 | dry | 47 | 0 |
| | 0.34 | 0 | dry | 48 | 0 |

Example 8

Application of $C_2N_2$ Using Flow Through Techniques

Aim To determine the toxicity of a continuous stream of $C_2N_2$ in air to insects.
Method and Materials
Four pieces of equipment were connected in line. These were:
1—a Tedlar gas bag of 100 L capacity;
2—an aquarium pump;
3—a gap meter/rotameter;
4—a bank of tubes (insect chambers) interconnected via dreschel heads and polythene tubing.
The flow of air through the Tedlar bag and then through the insect chambers was 50 mls min$^{-1}$.
Insect species tested were *Rhyzopertha dominica*(F), strain CRD2, Oryzaephilus Surinamensis(L), strain NOS405 and *Tribolium castaneum* (Herbst), strain CTC4.
The Tedlar bag was filled with air and $C_2N_2$ was injected through a septum into the bag to give a certain concentration of $C_2N_2$ in air. (Note a Tedlar bag has just one filling/emptying port and a septum seal).
A tube from the gas bag was connected to the inlet of the pump. The outlet of the pump was connected to the rotameter inlet. The outlet of the rotameter was connected to the bank of tubes. The last tube vented to the exterior.
Experiments were conducted at room temperature, 22–25° C. At the end of the exposure period, the insect chambers were disconnected and mortality assessed immediately, to give "acute" mortality, and again after a holding period, on wheat at 30° C. of 1 week.
Fumigant concentrations were determined by gas chromatography, on a Varian 3300 Gas Chromatograph, equipped with a Thermionic Specific Detector, after separation on a DBwax column, of internal diameter 0.53 mm. Concentrations used to calculate doses were the measured concentrations.
Results
Results are summarised in Table 4. The fumigant was effective in killing insects in a flow-through method of application, whereby the fumigant was applied in an air stream which was vented to the atmosphere.
Discussion
The technique of applying toxic gases in an air stream which vents to the atmosphere is used to apply ammonia and phosphine to grain. This low-flow technique can also be used with $C_2N_2$.

TABLE 4

Toxicity of insects of $C_2N_2$ in an air stream

| Insect Species | Amount applied (mgL$^{-1}$) | Expsoure period (Hrs) | (CxT) product (mg hr L$^{-1}$) | Mortality (%) acute | Mortality (%) 1 week |
|---|---|---|---|---|---|
| CRD2 | 0.04 | 22 | 0.88 | 13 | |
|  | 0.2 | 12 | 2.4 | 99 | 100 |
| NOS405 | 0.07 | 24 | 1.68 | 0.6 | 20 |
|  | 1.5 | 2 | 3 | 30 | 61 |
| TC4 | 1.0 | 14 | 14 | 100 | 100 |
| TC4 | 1.0 | 5.4 | 5.4 | 96 | 100 |

TABLE 5

Efficacy of $C_2N_2$ against L. bostricophila

| Amount applied (mg.L$^{-1}$) | Exposure period (Hrs) | (CxT) product (mg hr L$^{-1}$) | Mortality (%) post exposure | Mortality (%) 1 day |
|---|---|---|---|---|
| 0.5 | 1 | 0.5 | 100 | 100 |
| 0.25 | 1 | 0.25 | 100 | 100 |
| control | 1 | 0 | 12 | 12 |

Example 9

Efficacy of $C_2N_2$ against psocids (Pscoptera)

Aim To assess the toxicity of $C_2N_2$ against Psocids

Materials and Methods

Two species of psocids were tested. These were *Liposcelis bostrichophila* (Badonnel) and *Liposcelis entomophila* (Enderlein). The first species is parthenogenetic, and was obtained from an infestation in a household in Canberra. *L. entomophilia* is sexual, and was obtained from an infestation in a commercial wheat storage in Western Australia.

Psocids were brushed off filter paper strips into a small glass crystallising dish. Psocids were counted as they were tipped and brushed into the test chambers. These were Erlenmeyer flasks, (11.5 ml capacity) equipped with Minin-ert valves for injection of gas and sampling.

In other experiments, psocids were put in chambers with paper, and the chambers fumigated. These experiment was performed because psocids are not merely a pest of grain storages and households, but also a pest of libraries, museums, etc. as their common name of "book lice" testifies.

A few droplets of water were added to the higher inner surface of the flask prior to addition of insects and sealing.

Results

Mortality of *L. bostricophila* is shown in Table 5. This species of insect was rapidly killed, with 100% mortality obtained from a very low concentration by time product of 0.25 mg.h.L$^{-1}$.

An exposure of 1 h to 0.25 mgL$^{-1}$ of $C_2N_2$ killed 95% of adult *L. entomophila* and 100% mortality was obtained from a 1 h exposure to a concentration of 0.5 mgL$^{-1}$.

An exposure of 0.5 mgL$^{-1}$ for 2 h controlled *L. bostricophila* on paper, with adult mortality being 100% at the end of the exposure period and at final assessment, 1 day later. The control mortality was 12% at final assessment.

An exposure period of 1 h to each of 0.5, 1.0 and 1.5 mgL$^{-1}$ resulted in 100% mortality of adult *L. entomophila*, as assessed at the end of the exposure period.

Discussion

The fumigant $C_2N_2$ is effective in killing psocids in a variety of situations, such as empty chambers and in chambers where paper is present. Thus $C_2N_2$ can be effective in public buildings, libraries, museums, herbaria, etc, as well as in situations where durable or perishable commodities are kept. Psocids prefer high humidities, and the ability of $C_2N_2$ to act in such situations is useful.

Example 10

Application of $C_2N_2$ in a Recirculation System and the Effect on Insects

Aim: To determine whether $C_2N_2$ could be applied in a recirculation system and whether $C_2N_2$ applied in a continuous gas stream has a higher toxicity to insects that when applied under static conditions.

Materials and Methods

A recirculation system was established comprising a pump, a gas reservoir (20 L glass bottle stirred with a magnetic stirrer), a septum for injection of fumigant and for sampling gas concentrations and 6 Dreschel tubes, each of capacity 20 mL. Insects, typically 20 adults, were placed in each tube. The fumigant was injected into the system, while the pump was operating. After concentrations had been averaged throughout the system by recirculation, three of the six insect chambers were disconnected and sealed immediately. Three of the six chambers remained under recirculation. The disconnected chambers held under static conditions and the chambers subjected to a recirculating gas concentration were dosed for equal periods of time in all experiments, and at identical temperatures (22–24° C.).

Test insect were adults of *Rhyzopertha dominica* (F.), strain CRD2, and *Tribolium castaneum* (Herbst), strain CTC4.

Mortality was assessed at the end of the exposure period, to give "acute" mortality, and again after a 2 week holding period on wheat at 30° C., 55% relative humidity to give "final" mortality. Insects were classified as dead if they showed no movement of any description.

Results and discussion

Results are shown in Table 6. Mortality was higher in the chambers dosed under flow conditions for each species. The difference between results from recirculation and from static exposure were, however, not great.

Discussion

The fumigant $C_2N_2$ can be used with recirculation. The results demonstrate that the fumigant can be distributed in an air stream, and that it is toxic whether or not the forced recirculation is stopped. Thus recirculation, whether continuous or discontinuous, increases the options for control of insects and other pests. The toxic concentration for a 22 h exposure against *R. dominica* was a low 0.04 mgL$^{-1}$ (approximately 20 ppm, V/V). This is only twice the TLV for worker exposure. Thus the ratio of toxic dose to insects to TLV is unexpectedly low.

TABLE 6

Mortality of R. dominica and T. castaneum exposed to $C_2N_2$ concentrations under static and flow conditions

| Insect species | Applied amount (mg.L$^{-1}$) | Exposure period (Hrs) | (CxT) product (mg hr L$^{-1}$) | Mortality (%) acute | final |
|---|---|---|---|---|---|
| RD2 | f-0.04 | 22 | 0.88 | 13 | 29 |
| RD2 | s-0.04 | 22 | 0.88 | 6 | 14 |
| TC4 | f-1.0 | 5.4 | 5.4 | 95.6 | 77 |
| TC4 | s-1.0 | 5.4 | 5.4 | 89.3 | 70 | f - Continuous gas flow for the duration of experiment (50 mls/min)
s - Static no gas flow (stoppered after gas flows established)

Example 11

Effect of Humidity on Toxicity of $C_2N_2$ to Insects

Aims:
1. To determine the effect of relative humidity on the toxicity of $C_2N_2$ to insects;
2. To see if $C_2N_2$ were toxic in aqueous solution, as well as in gaseous form.

Materials and Methods

Method 1

Varying humidities were generated in 275 ml flasks prior to addition of insects. The flasks were then sealed with a septum inlet and dosed with identical amounts of $C_2N_2$. Toxicity was determined under identical conditions of holding period, temperature, etc., with the only variable being the relative humidity in the flasks.

Three humidities were generated. In one method, flasks were left in a room at 30% humidity and, in a second method, flasks were left in a room at 60% humidity. In the third method, a damp piece of filter paper (Whatman No.1) was stuck to the side of the flask such that visible water was observable throughout the experiment, but insects did not come into contact with the water.

Method 2

In this method, $C_2N_2$ was added, in two ways, to insects on wheat (20 g) in 270 mL Erlenmeyer flasks which had previously been left open to room air. In one method, the fumigant was added as a gas; in the second method, it was added in a solution of water (0.1 ml). All bioassay conditions were identical, apart from the method of application.

The amount of fumigant applied was determined by gas chromatography, using a Varian 3300 Gas Chromatography equipped with a thermionic specific detector, after separation on a DB wax column, of internal diameter 0.53 mm.

The test insect was Rhyzopertha dominica strain CRD2. Mortality was assessed after a holding period of two weeks on flour at 30° C., in the case of Method 1, and after a holding period of 1 week, in the case of Method 2.

Results

Method 1

The effect of relative humidity on the toxicity of $C_2N_2$ to adult R.dominica is demonstrated in Table 7. The toxicity of the fumigant increased at higher humidities. This effect was observed over a range of concentrations and over a range of exposure periods.

Method 2

The effect of method of application is demonstrated in Table 8. The fumigant was toxic, whether it was applied as a gas, or in solution.

Discussion

The enhancement of activity of the fumigant at higher humidities is an unexpected effect, especially with regard to the magnitude of the effect. High relative humidities exert a synergistic effect on the fumigant, and water can be regarded as a synergist.

The ability to apply a fumigant both as a gas and as an aqueous solution is novel. It relies partly on the solubility of the fumigant in water. This is high, and the Merck Index states that 1 volume of water dissolves approximately 4 volumes of gas. This would generate an aqueous concentration of approximately 8 mg of $C_2N_2$ per mL of water. A saturated solution would be approximately 0.15M. The toxicity of $C_2N_2$ applied in water also partly depends on the fact that the gas is toxic at high humidities. This is because application in water generally has the effect of raising the relative humidity.

Thus there are two unusual effects, namely enhancement of activity with water and the ability to apply the fumigant in water.

The first effect is useful in a number of areas, especially those where relative humidity is high, which include glasshouses, enclosed areas containing vegetables and cut flowers, tropical climates and other areas where the humidity is high.

The ability to apply the fumigant as an aqueous solution is useful in many areas. For example, the fumigant can be sprayed onto durable or non-durable commodities, plants, sterilisation chambers and empty chambers. It enables application via pumps, for larger applications, or syringes, for smaller applications, and by other methods where the volume of liquid can be measured, as distinct from measuring gas volumes, which is a more complicated procedure.

The high solubility of $C_2N_2$ in water also facilitates quantification by chemical procedures that do not require expensive machinery, such as gas chromatographs.

TABLE 7

Effect of relative humidity in the fumigation chamber on the toxicity of $C_2N_2$ to R. dominica

| Amount applied (mgL$^{-1}$) | Exposure period (Hrs) | Relative humidity | (CxT) product (mg hr L$^{-1}$) | % Mortality 2 week |
|---|---|---|---|---|
| 0.375 | 17 | wet | 6.6 | 100 |
| 0.375 | 17 | 60% | 6.3 | 100 |
| 0.375 | 17 | Dry | 6.3 | 94 |
| 0.375 | 2 | wet | 0.75 | 35 |
| 0.375 | 2 | 60% | 0.75 | 20 |
| 0.3752 | 2 | dry | 0.75 | 1 |
| 1.25 | 0.4 | wet | 0.52 | 100 |
| 1.25 | 0.4 | 60% | 0.52 | 92 |
| 1.25 | 0.4 | dry | 0.52 | 8 |

TABLE 8

Toxicity of $C_2N_2$ applied either as a gas or in aqueous solution

| Amount applied (mgL$^{-1}$) | Exposure period (Hrs) | Application method | (CxT) product (mg hr L$^{-1}$) | Mortality (%) 1 week |
|---|---|---|---|---|
| 0.8 | 2.16 | wet | 1.7 | 100 |
| 0.8 | 2.16 | dry | 1.7 | 100 |
| 0 | 2.16 | control | 0 | 5 |
| 1.25 | 0.4 | wet | 0.5 | 2 |
| 1.25 | 0.4 | dry | 0.5 | 4 |
| 0 | 0.4 | control | 0 | 2 |

Example 12

The Toxicity of $C_2N_2$ to Bactocera (Formerly Dacus) tryoni (Froggart)

Aim: To determine lethal doses of $C_2N_2$ for Bactocera Tyroni (Froggart) (Queensland fruit fly.)

Method and materials

Early larvae (20) were placed on a wet strip of filter paper supported by a strip of perspex. This strip was placed into an Erlenmeyer flask sealed with a ground glass septum seal top. $C_2N_2$ gas was injected into the flask via the septum seal. After exposure, the tops were removed and the flasks flushed with a stream of air for 30 seconds then left to air for 30 minutes before sealing with paper.

Results

Results are shown in Table 9.

Complete control was achieved at 1.5 mg $L^{-1}$ dosed for a period of two hours. The concentration by time (C×T) product was a low 3 mg.h. $L^{-1}$.

Discussion

Queensland fruit fly is an important pest of fruit, and the subject of quarantine restriction in parts of Australia and in many importing countries. It is also a representative of the Diptera. The results also demonstrate the efficacy of $C_2N_2$ in environments of high humidity.

Cross reference is made to Example 11, which outlines further data and data by application of $C_2N_2$ as a liquid.

TABLE 9

Mortality of *B. Tyroni* exposed to varying concentrations of $C_2N_2$

| Applied amount (mg $L^{-1}$) | Exposure period (Hrs) | CxT product (mg hr $L^{-1}$) | Mortality % 48 hrs after end of exposure |
|---|---|---|---|
| 0.05 | 2 | 0.1 | 0 |
| 0.05 | 24 | 1.2 | 2.5 |
| 0.2 | 2 | 0.4 | 0 |
| 0.75 | 2 | 1.5 | 40 |
| 0.8 | 2 | 1.6 | 62.5 |
| 1.5 | 2 | 3 | 100 |
| 3 | 2 | 6 | 100 |

Example 13

Removal of $C_2N_2$ From Gas Streams

Aim: to determine procedures for removing $C_2N_2$ from gas streams.

Materials and Methods

The apparatus comprised a 3-necked flask (500 mL capacity), with one neck equipped with a septum for injection of the fumigant, and one connected to a supply of gas (e.g., nitrogen). The third neck, for exhaust of fumigant, was connected to a glass tube, of internal diameter 6 mm, with a sampling septum before the trap (the inlet septum), a trap, and a second sampling septum after the trap (the outlet septum).

Traps tested were granulated charcoal in a glass tube of internal diameter 6 mm, with length of granulated charcoal both 157 mm and 530 mm, a 5% solution of ethanolamine in water, a small (55 mm) charcoal trap surrounded by dry ice and dry ice, without any chemical trap. In the case of dry ice trap, the effluent gas was run into a Dreschel bottle, wrapped in dry-ice, and sampling septa were placed at the inlet and outlet of the Dreschel tube.

A small amount of fumigant (typically 0.5 mL, approximately 1 mg) was injected into the 3-necked flask. Samples of gas (50 μL) were taken from the inlet septum and injected into the gas chromatograph and a similar procedure was used for samples at the outlet septum. Fumigant concentration was determined on a Varian 3300 Gas Chromatograph, equipped with a Thermionic Specific Detector, after separation on a BP624 or DBwax column, of internal diameter 0.53 mm.

Results

Figure 3:
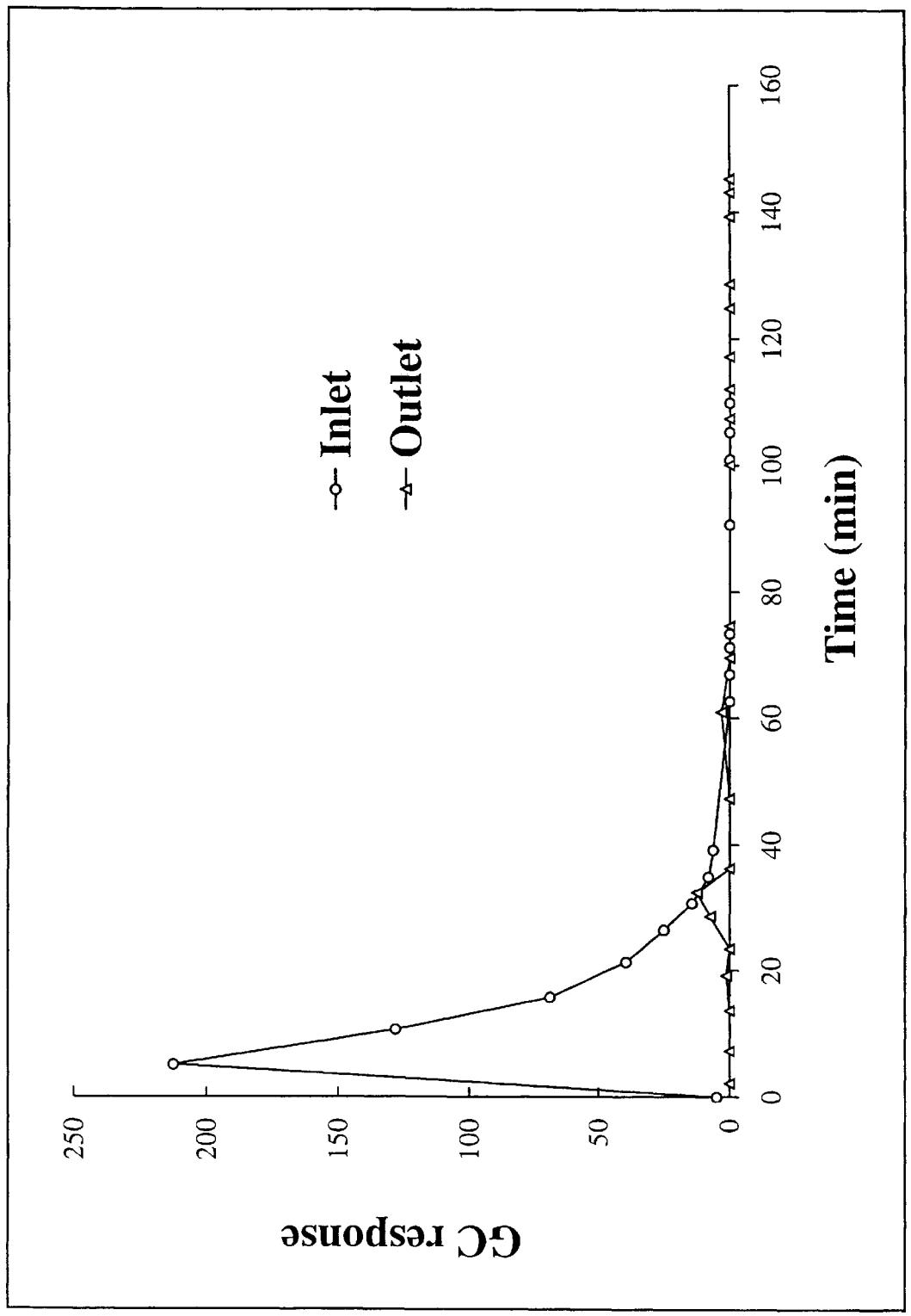
FIGS. 3 to 7 graphically illustrate the results of various procedures for removing $C_2N_2$ from gas streams.
Figure 4:
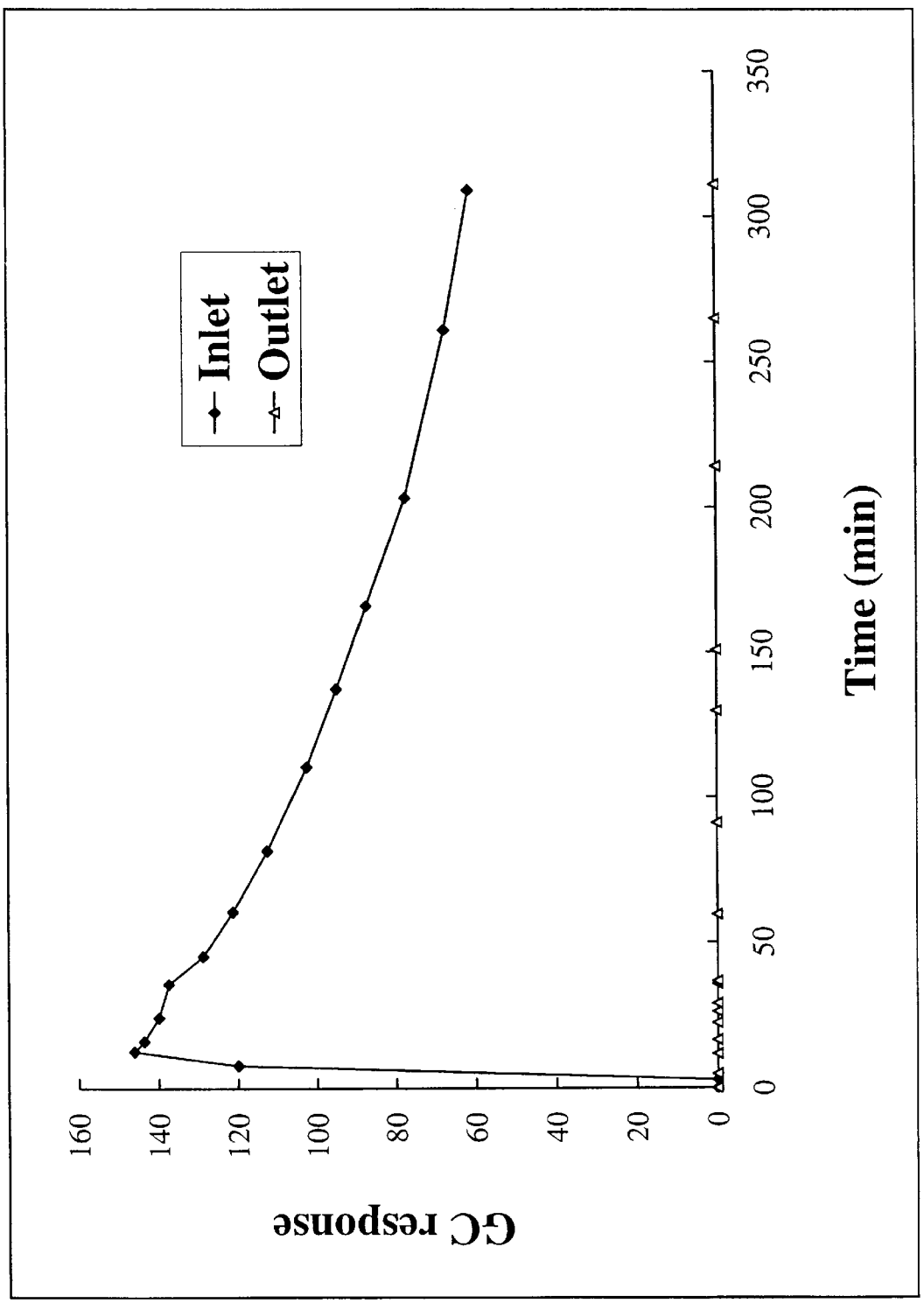
Figure 5:
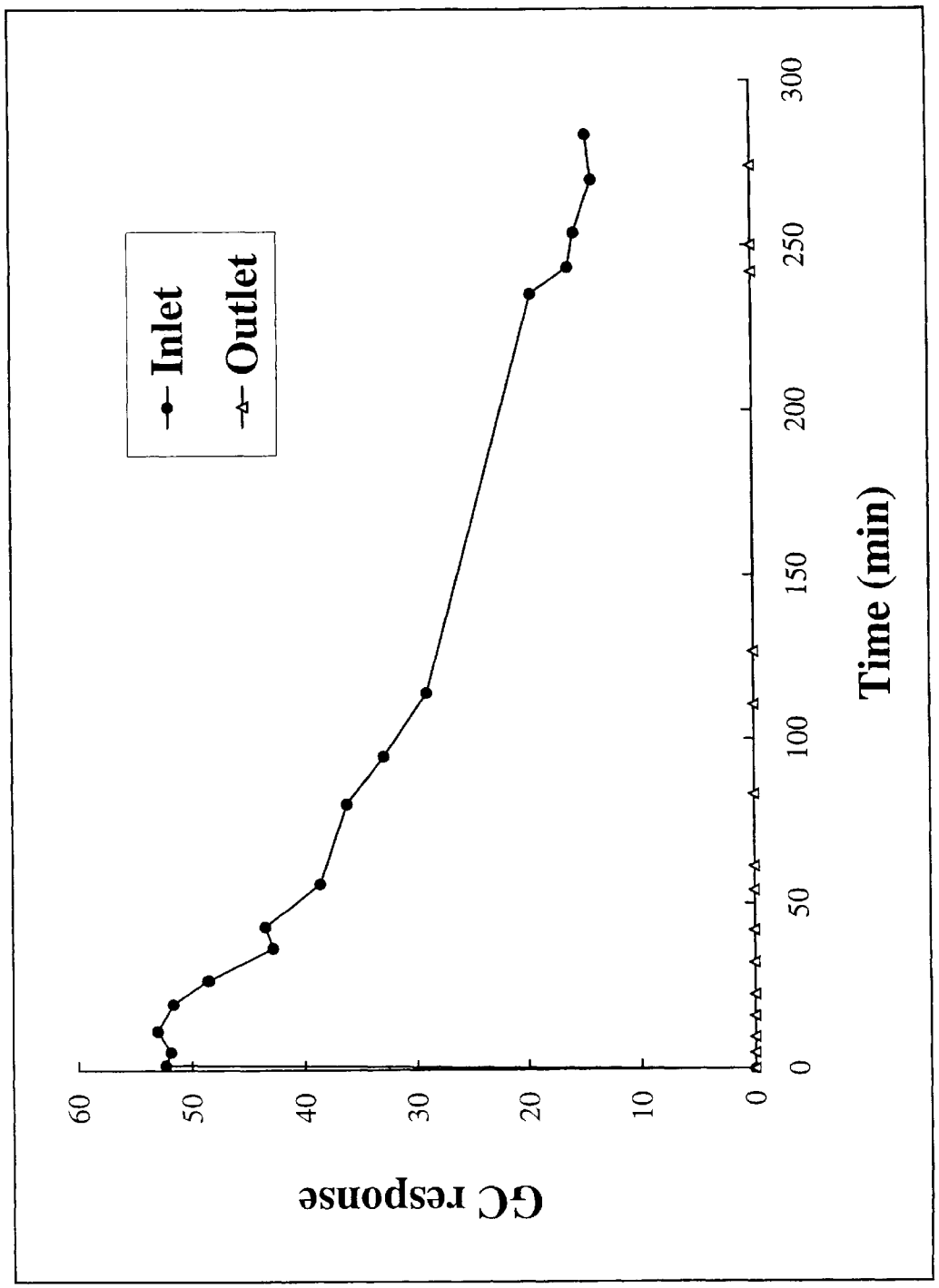
Figure 6:
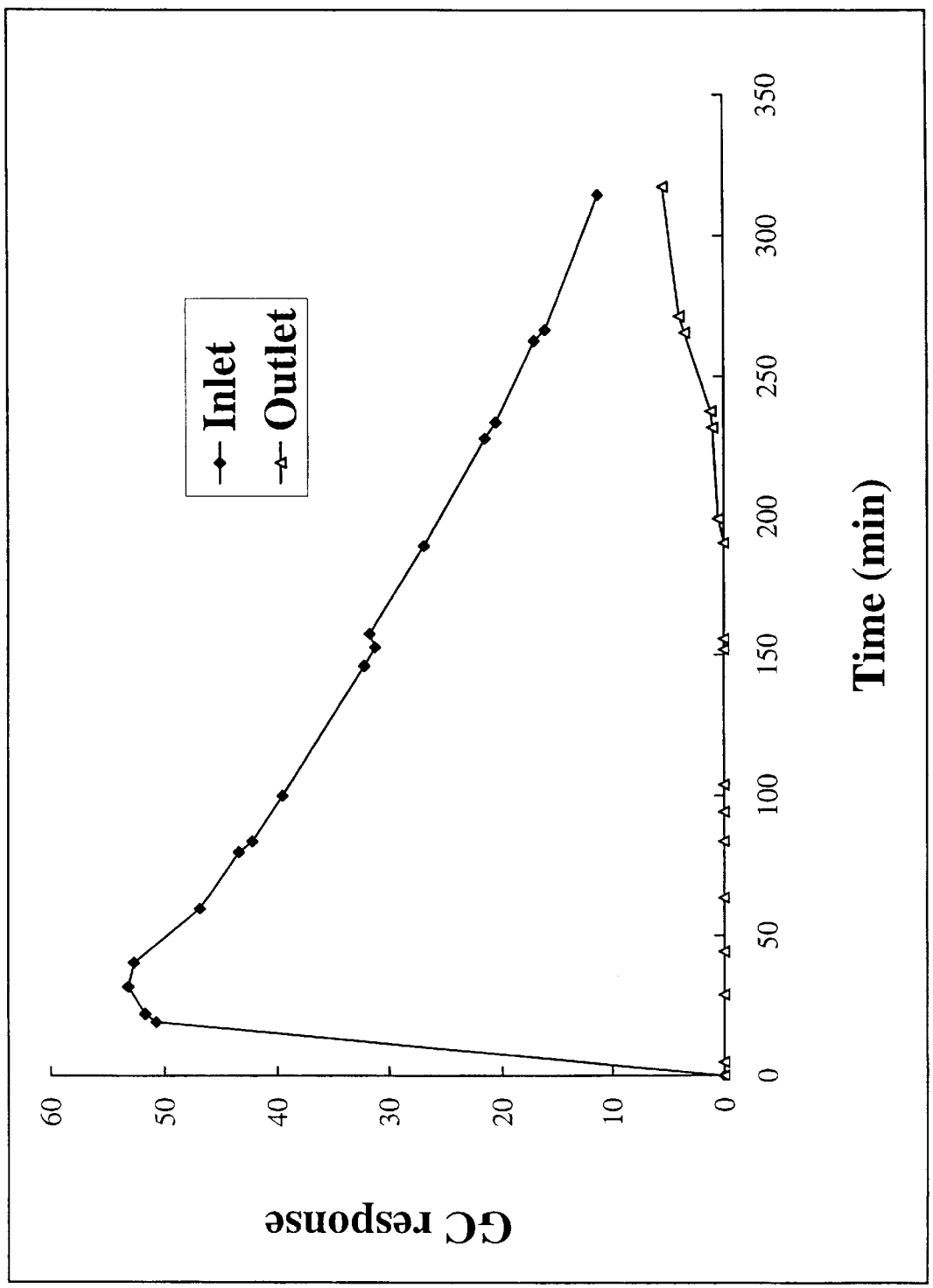
Figure 7:
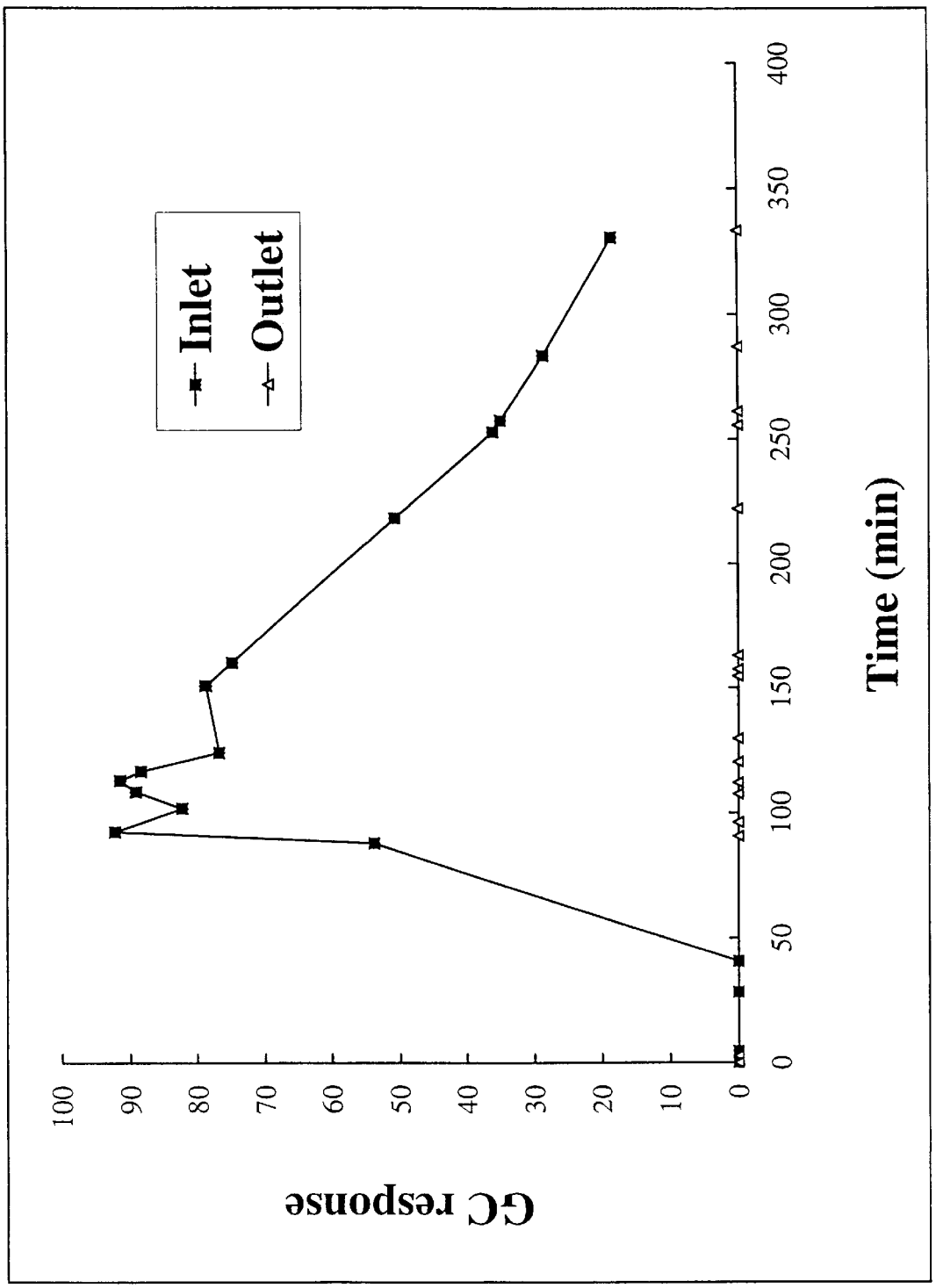

With the charcoal trap of 157 mm length (see FIG. 3—$C_2N_2$ trapped in a short glass column which contained granulated charcoal), a small amount of fumigant was detected at the outlet sampling point. This small trap absorbed most, but not all, of the fumigant. The longer trap (530 mm) absorbed all of the fumigant (see FIG. 4—$C_2N_2$ trapped in a long glass column which contained granulated charcoal). The solution of ethanolamine in water was also fully efficient (see FIG. 5—$C_2N_2$ trapped in a 5% v/v solution of ethanolamine in water). With this trap, as with the long charcoal trap, no fumigant was detected with prolonged purging. The dry ice trap was fully efficient while the dry ice was present (150 min.). With the removal of the dry ice, the system did not trap the fumigant (see FIG. 6—$C_2N_2$ trapped in dry ice without any chemical trap). The small charcoal trap with dry ice was fully efficient, even after the removal of the dry ice (see FIG. 7—$C_2N_2$ trapped in a small charcoal column surrounded by dry ice). However, after removal of the dry ice and the inlet system, some fumigant moved from the trap to the inlet sampling point, but not to the outlet sampling point.

Discussion

These trapping results are not unexpected, and fully consistent with known properties. Thus it is to be expected that a gas can be trapped, in a recoverable manner, below its boiling point and it is known that $C_2N_2$ reacts rapidly with amines (in this case ethanolamine), in a manner such that the chemical is rapidly destroyed. Trapping on charcoal is also a common procedure and, as is always the case for sorption, conditions such as quantities of sorbent must be adjusted to the situation set by flow rate, quantity of fumigant, etc.

However, it is very useful to be able to be able to trap a fumigant in a gaseous stream, and to trap it in ways that either destroy the fumigant, or enable it to be recovered, according to preference.

The list of traps is not exhaustive, and no novelty is claimed for the trapping procedures per se. The ability to trap is part of the package.

Example 14

Methods for Removing $C_2N_2$ in air or in Aqueous and Other Solutions After Fumigation, Apart from Methods Involving Removal of Air or Water Aim: to provide safe and rapid methods to remove $C_2N_2$ from air or liquids, by methods other than venting or removal.

Material and methods

The fumigant was placed in sealed flasks such as flasks fitted with Mininert valves or Erlenmeyer flasks, fitted with septum inlets. To these flasks were added common household reagents such as ammonia solution or ethanol or bleach (hydrogen peroxide). The decay of the fumigant was measured over time.

In alternative experiments, solutions of amines in water (20 mL) were placed in 270 mL flasks, fitted with septum inlets, and stirred with a magnetic stirrer. Fumigant was injected through the septum and its decay monitored. All measurements were performed on a Varian 3300 gas chromatograph, equipped with a thermionic specific detector, after separation on a DBwax column, of internal diameter 0.53 mm.

Results

Figure 8:
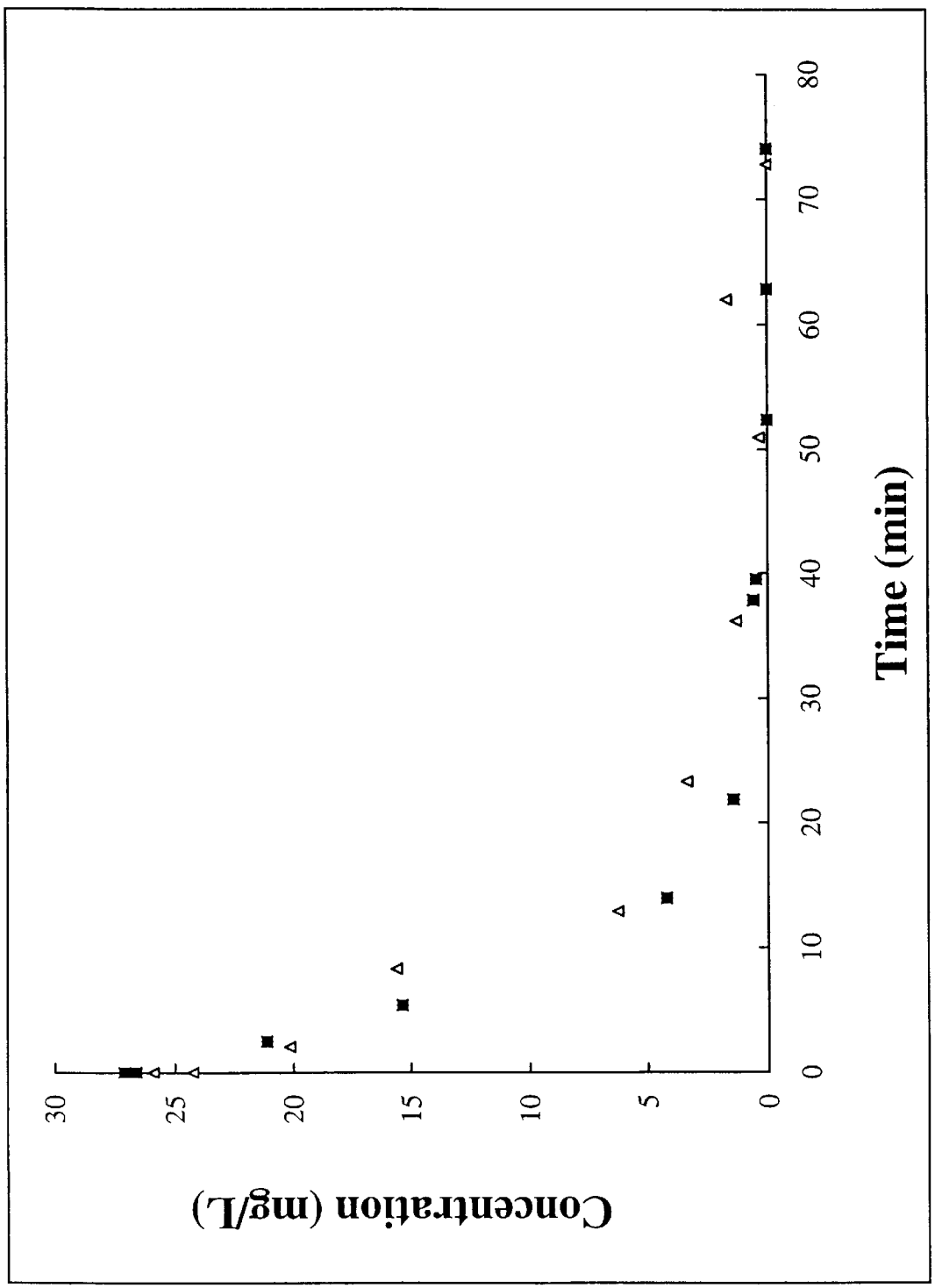
FIGS. 8 and 9 illustrate the results of procedures to remove $C_2N_2$ from air or liquids, by methods other than venting or removal.
Figure 9:
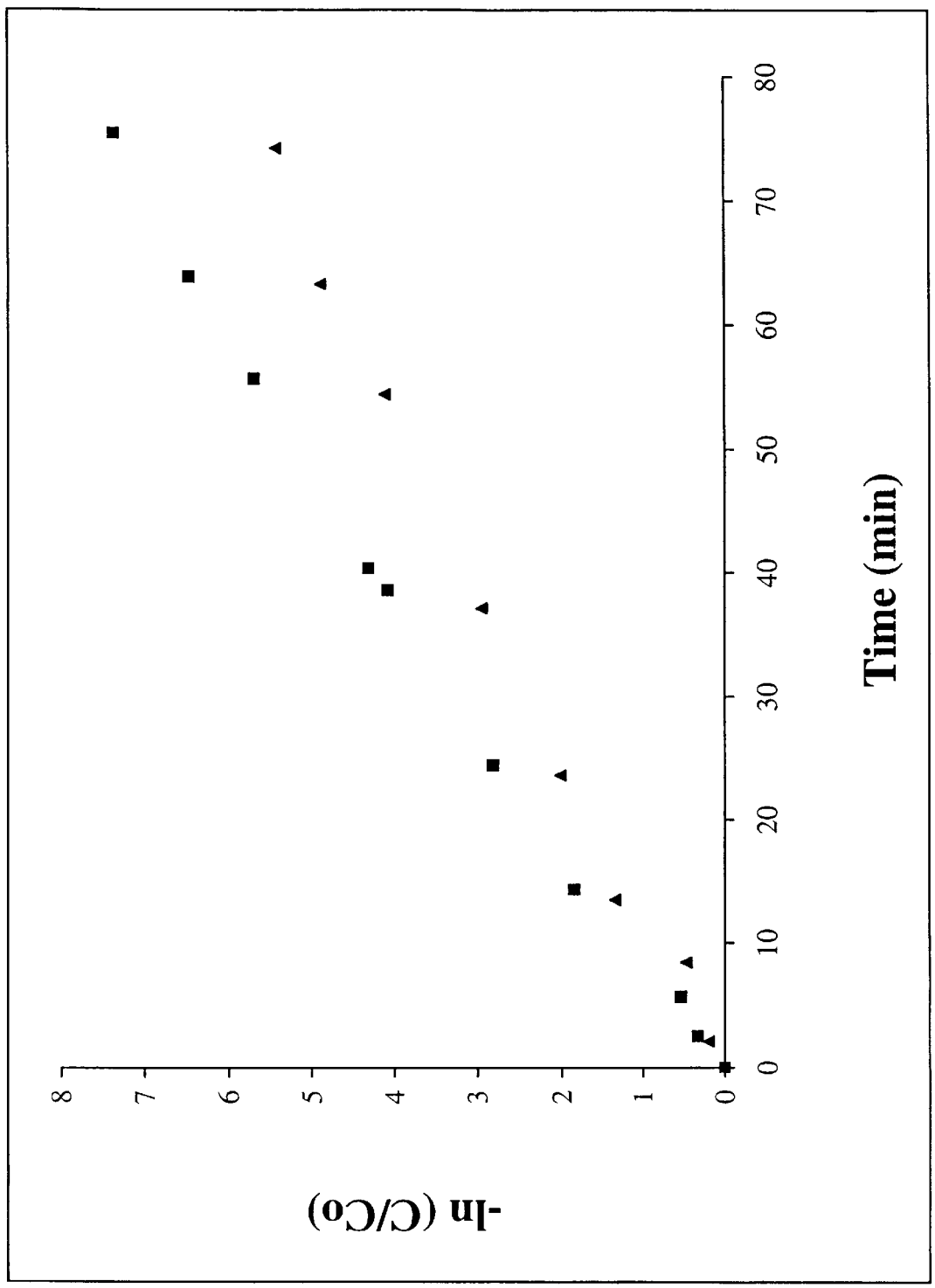

The disappearance of the fumigant from the headspace is illustrated in FIG. 8, which plots concentration of the fumigant against time after dosing. In FIG. 9, this loss is plotted according to the plot for first-order decay, Eq. 1. The vertical scale records the logarithm of the ratio of the concentration C, at time t, to the initial concentration. The depletion covers the range of $e^7$ (approximately 1000).

Addition of 0.5 mL aqueous ammonia (31%, W/W) to $C_2N_2$, at a concentration of 11.6 mg/L, resulted in a rapid loss of the fumigant. The concentration, C, as a proportion of the applied concentration, C*, declined exponentially with time t (in min) according to Equation 1, with an $r^2$ value of 0.9966. The half-life, that is, the time taken for a concentration to halve, was 59 sec. The concentration of $C_2N_2$ fell below the TLV value of 10 ppm, V/V, after 11 minutes.

$$\ln(C/C_0) = 4.4 - 6.699t \qquad \text{Equation 1}$$

Addition of $C_2N_2$ gas (5 mL) to a 120 mL flask containing 25 mL of 0.4M benzylamine in methanol was followed by a very rapid loss of fumigant, with more than 99% of the fumigant lost before it was possible to take a measurement (15 sec). The gas concentration declined from above 40,000 ppm, V/V (the theoretical applied amount) to less than the TLV value of 10 ppm in 8 minutes. The concentration over 0.2M sodium carbonate (washing soda) declined by a similar amount in 26 min.

When the concentrations in the head space had declined to less than the TLV concentration, the concentration in the liquid was measured and was undetectable. Thus the rapid disappearance from the headspace is due to breakdown, and not merely to absorption.

Addition of 5 mL of hydrogen peroxide in water (3%, V/V) to a 270 mL flask containing 2960 ppm hydrogen cyanide, V/V resulted in a rapid loss of hydrogen cyanide in the headspace. Decay was approximately exponential with a half-life of 1.8 min. The concentration fell below the TLV value of 10 ppm, V/V, after 14.2 minutes. The concentration of $C_2N_2$ was relatively stable over hydrogen peroxide.

Discussion

The reaction of $C_2N_2$ with amines has been well studied, from the point of view of the products formed (Brotherton and Lyn, 1959). Even so, the speed of the reaction was surprising. The novelty of the procedure lies in its use as part of a total procedure. That is, the fumigant can be introduced and held in an enclosed chamber, but the concentration removed rapidly by addition of such chemicals as ammonia. Thus $C_2N_2$ can be removed by trapping (cf Example 13), but also by addition of common chemicals which remove it from enclosed spaces, without the need for venting.

The rapid destruction of $C_2N_2$, in the gas phase, by reaction with a solution of an amine was also demonstrated in the section on removal of $C_2N_2$ from gas streams, where it was shown that the simple procedure of bubbling the gas through an aqueous solution of ethanolamine destroyed the fumigant (see Example 13).

The procedure has potential uses in many areas. For example, it can be used to make enclosed rooms safe for human entry a short time after end of fumigation, it can be used on small or large fumigation chambers, it glasshouses, or other situations where it is desired to reduce the $C_2N_2$ concentration rapidly.

The ability to rapidly destroy fumigant concentrations, by means other than trapping in an air stream and by addition of such common chemicals as ammonia, is novel, and has not been applied to any other fumigant, though such fumigants can be destroyed by more complicated procedures. It is feasible that hydrogen cyanide could be destroyed by similar procedures, but there is no simple way, using household chemicals, to destroy such fumigants as methyl bromide or phosphine. The use of a combination of reagents, such as washing soda and peroxide, removes and destroys both $C_2N_2$ and any hydrogen cyanide present.

Example 15

Chemistry of Cyanogen and Possible Metabolism Products

The chemistry of cyanogen has been reviewed by Brotherton and Lynn, 1959. A number of the reactions outlined by Brotherton and Lyn, 1959, eg those at high temperature, are of little immediate relevance to metabolism in grain or in mammalian systems. However, a number of reactions occur at room temperatures in water, or in water soluble solvents such as ethanol.

1. Chemistry of probable relevance to metabolism in grains

The main initial reaction is addition across a triple bond (a CN bond). This gives rise to product or intermediate (I). A second addition leads to product (II). Chemicals that react with cyanogen include primary and secondary amines, alcohols, active hydrogens (e.g. those adjacent to carbonyl groups or ester groups) and aldehydes with an α-hydrogen, i.e. those able to react in the enol form.

Compounds of type (I) and (II), with R formed from an amine, alcohol or active carbon, would be expected to be further biodegradable. Intermediates of type (I) could cleave to HCN and a one carbon unit ("formate" derivatives) and this occurs in dilute sodium hydroxide (Naumann, 1910). Intermediates of type (II) would be oxidised to 2-carbon units ("oxalate" derivatives).

The Matheson data sheet states that, in water, cyanogen gradually decomposes, on standing, into a mixture of ammonium oxalate, ammonium formate, hydrogen cyanide and urea, in addition to a more complex chemical, azulmic acid. The Merck index (1989) states that it is slowly hydrolyzed in aqueous solution to oxalic acid and ammonia. Thus, in water, breakdown follows both the formate and the oxalate pathway, with the latter predominating. Formic acid and oxalic acid are widely distributed natural constituents. For example, oxalic acid is a constituent of normal urine, with the average amount excreted by humans being 20–50 mg per day (Oser, 1966), although urinary oxalic acid is increased in certain diseases (oxaluria). Formic acid is also present in urine (Oser, 1966) and is present in dried fruits and grains in amounts up to 0.1% (unpublished results from our laboratory). Oxalic acid is present in most green vegetables, especially in spinach (0.0–0.9% oxalic acid) and rhubarb leaves (1.2%).

The metabolism of cyanogen of grain must eventually be studied using labelled materials. However, it is probable that the compounds of type (I) and (II) will be formed, together with their further degradation products. The amount of cyanide formed will give an indication of the amount of metabolism via the formate pathway, and can be measured using standard procedures.

2. Chemistry relevant to stability during transport and storage

The stability of cyanogen has been studied by Welcher et al., 1957, who concluded that cyanogen did not decompose or polymerise rapidly at moderate temperature and could be safely stored in Monel or stainless-steel cylinders in the absence of a stabiliser. The Matheson data sheet on cyanogen states that glass-lined equipment is suitable for conveying or processing cyanogen, as is stainless steel, monel and inconel up to 65° C.

Shipping of cylinders of cyanogen is approved in the USA, with appropriate labels (the reader is referred to Example 23).

Cyanogen contains a high latent energy, of the same order as acetylene, and can react explosively when mixed with oxidizing agents such as fluorine.

The flammability of cyanogen in air is 6–32%, V/V (Matheson data sheet) or 6.6–32%, V/V (Sax and Lewis, 1989).

Cross references in vitro studies were conducted with benzylamine and cyanogen Example 37, which showed that this model amine decomposed cyanogen, without being decomposed itself. That is, it acts as a catalyst. Studies on grain at very high doses shows that the decomposition of $C_2N_2$ to hydrogen cyanide was a minor pathway (Example 3 and 38).

Example 16

Sorption of $C_2N_2$ on Wheat and Stability in Sealed Glass Containers

Aim: to determine sorption of $C_2N_2$ on wheat, under conditions used in studies on viability, in some studies on insect toxicity and in some studies on the fate of residues, as determined in a fully-sealed system.

Materials and Methods

Australian standard white wheat (20 g), of moisture content 11.6%, was placed in a 270 mL Erlenmeyer flask equipped with a septum. Fumigant gas was applied to this container, and also to an equivalent container, which did not contain wheat. This empty flask was used to calculate the applied concentration, $C_0$. Headspace concentrations of $C_2N_2$ were measured, at timed intervals, over a period of 110 h. The fumigant was determined on a Varian 3300 Gas Chromatograph, equipped with a thermionic specific detector, after separation of a BP-624 column, of internal diameter 0.53 mm.

The applied concentration was measured at each sampling interval, and the measured concentration was compared with that of an equivalent standard prepared at each sampling interval.

The concentration in the headspace was plotted against sampling time and the loss of headspace concentration expressed as sorption.

Results

Figure 10A:
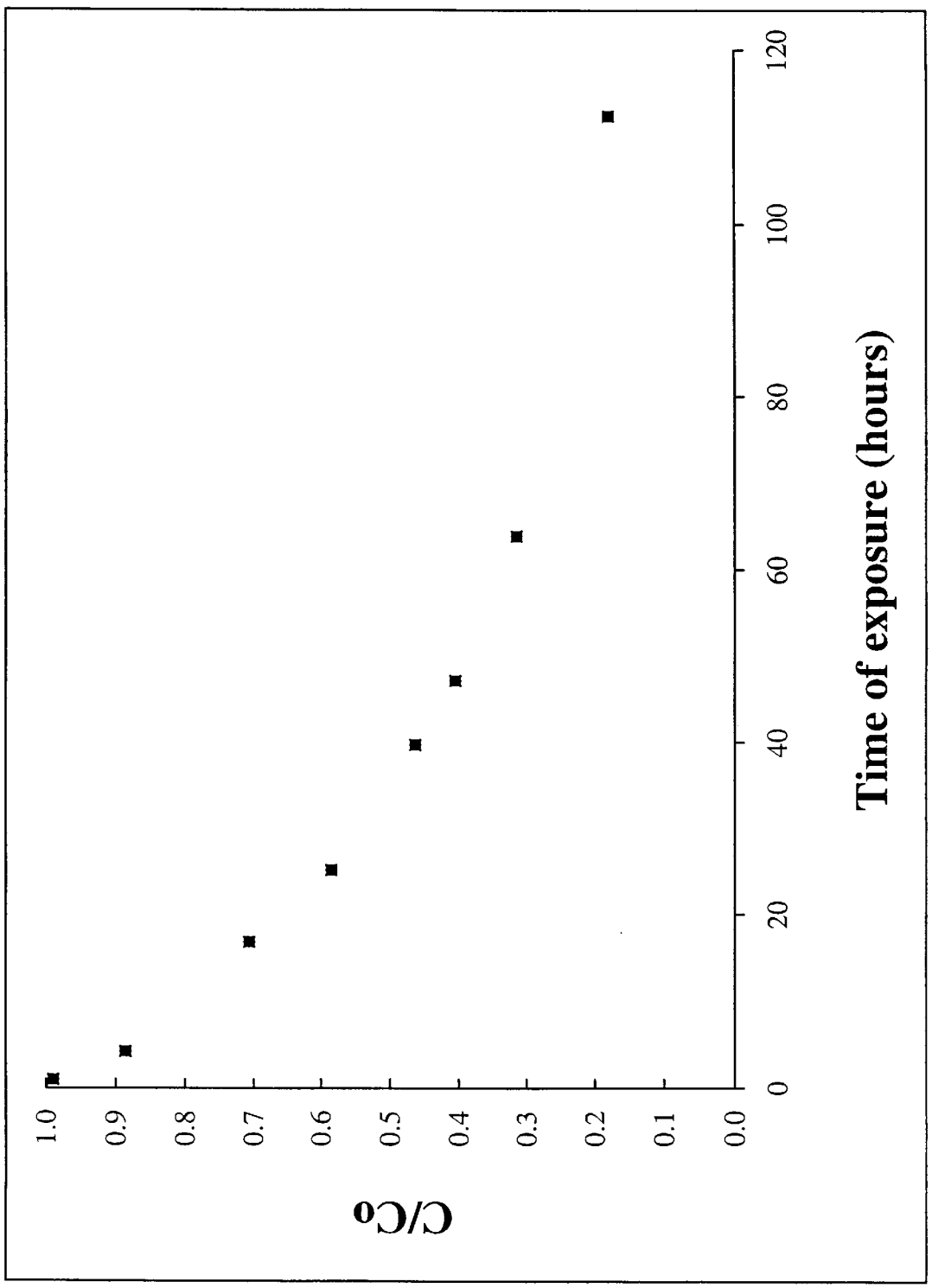
FIGS. 10(*a*) and (*b*) illustrate $C_2N_2$ sorption on wheat.
Figure 10B:
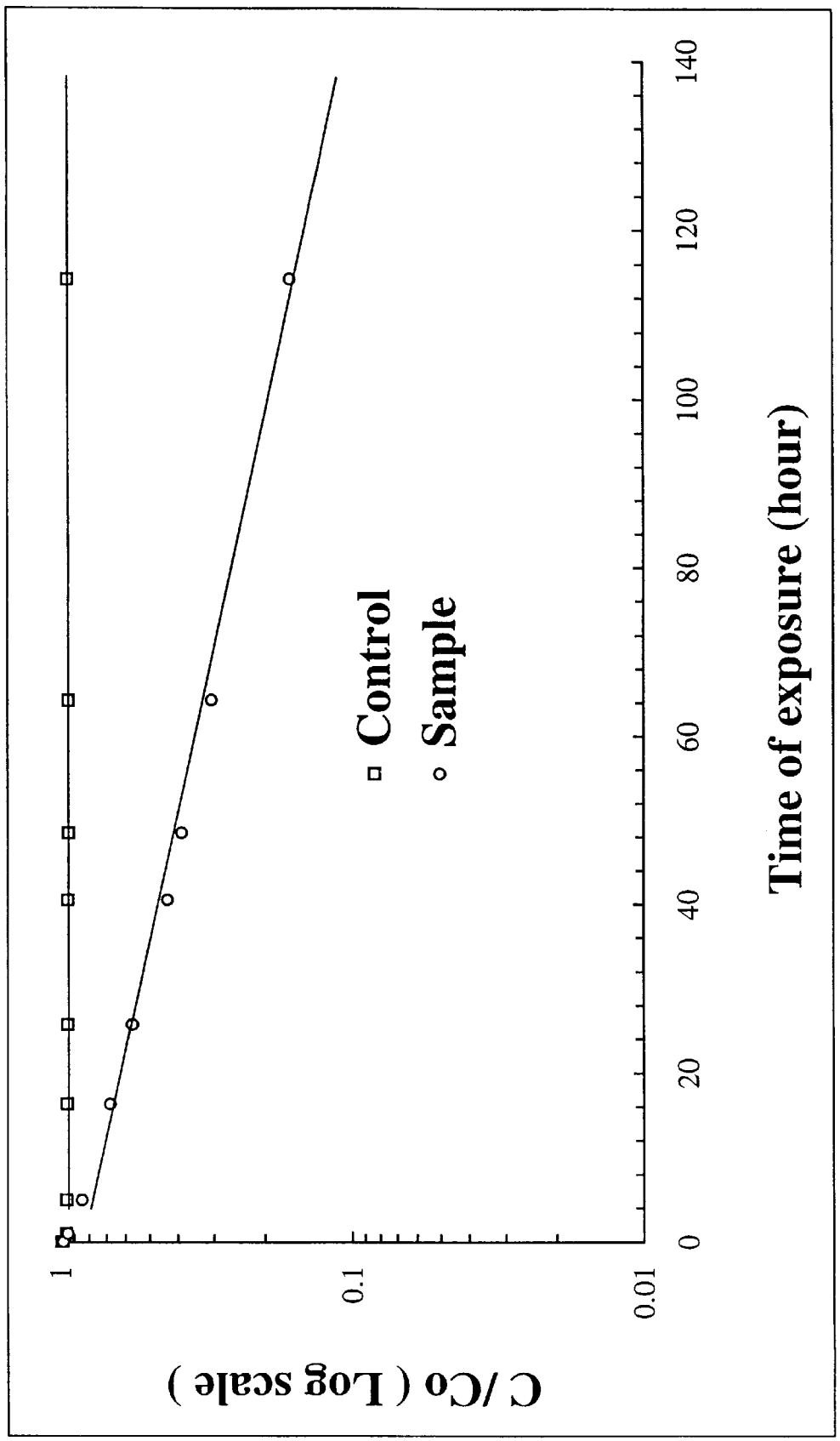

The decay of the fumigant in the headspace is shown in FIG. 10a, where it is expressed as a ratio of the applied concentration. The curve shows a typical pattern of a rapid initial drop in headspace concentration, followed by a decay that is approximately exponential (FIG. 10b). In this "exponential" decay, the half-life, that is the time for the concentration to halve, is approximately 43 h.

The control sample showed no loss of fumigant over a period in excess of 100 h. Thus $C_2N_2$ is stable in air in sealed glass containers.

Discussion

The form of sorption (that is, loss of headspace concentration) is not unusual for fumigants. The calculated dose could be corrected, if desired, to account for the space occupied by the wheat. This would have the effect of increasing the value of $C_0$ by 3.7%, and would be a constant effect, without any effect on the half-life.

The stability of $C_2N_2$ in air, under the conditions specified, is a pleasing result. It certainly facilitates experimental procedures, including those for studies on toxicity or on residues. The stability in air in sealed glass containers also justifies inferences such as the sorption on wheat is due to the commodity, rather than to leaks, breakdown on glass, etc.

Stability of the fumigant under controlled conditions has potential applications for specialised fumigation procedures. Such a case, for example, is sterilisation that requires a long exposure. In situations where breakdown of the fumigant occurs, a long exposure can be achieved via a flow-through procedure, or recirculation with fumigant added to maintain an appropriate or desired concentration. In other situations, the stability of the fumigant in air can be a useful tool for fumigation, maintaining sterility, etc.

Other sorption studies are reported for wheat (Example 26), soils (Example 42) and timber (Example 33).

The stability of $C_2N_2$ in air in a sealed glass container has no direct relevance to its stability in the atmosphere, because of the presence of other chemicals, including water, in the atmosphere, sunlight, etc.

Example 17

Aqueous $C_2N_2$ as a Dip to Control Insect Infestation on Plants

Aim: To assess the efficacy of $C_2N_2$ as a dipping agent to kill insects on plant material.

Materials and Methods

Two types of pot plants with natural infestations of pest insects were obtained from a local nursery; German Ivy (*Senecio mikanoides*)(GI) infected with aphids (family Aphididae) and mealy buts (family Pseudococcidae) and China Doll (*Radermachia sinica*)(CD) infected with mealy bugs. Short sections (approximately 5 cm) of each plant were cut such that they included representative samples of insects. These were then dipped into solutions of tap water, tap water and $C_2N_2$ tap water and a general wetting agent and tap water, wetting agent and $C_2N_2$.

Insect mortality was assessed after 2 hours, mealy bugs were removed carefully with a fine brush and viewed to see if their legs were moving and Aphids were simply viewed for movement, a lack of movement was assumed to indicate death.

The wetting agent used was Teric 215 (ICI, Australia) at a rate of 1 mL in 400 mL of tap water. $C_2N_2$ soutions were made by bubbling 4 mL of $C_2N_2$ gas with a concentration of approximately 80% into 40 mL of water or water/wetting agent solution in an container (approximately 130 mL) and shaking vigorously for two minutes.

Results

The plant material displayed no ill effects due to the various treatments. Insects from two major insect orders were killed. Control mortality from water with or without wetting agent was zero.

| Wetting agent | NF2 | Plant | Insect | Dead/Alive |
|---|---|---|---|---|
| No  | No  | GI | Aphid  | Alive |
| No  | No  | GI | M.Bug  | Alive |
| Yes | No  | GI | Aphid  | Alive |
| Yes | No  | GI | M.Bug  | Alive |
| No  | No  | CD | M.Bug  | Alive |
| Yes | No  | CD | M.Bug  | Alive |
| No  | Yes | GI | Aphid  | Some dead |
| No  | Yes | GI | M.Bug  | Some dead |
| Yes | Yes | GI | Aphid  | Dead |
| Yes | Yes | GI | M.Bug  | Dead |
| No  | Yes | CD | M.Bug  | Some dead |
| Yes | Yes | CD | M.Bug  | Dead |

Discussion

Aqueous solutions containing $C_2N_2$ have potential as a dip to kill insects on plant material. The concentration required has not yet been ascertained and will undoubtedly vary according to the level of control required and the insect pests being treated. It would also appear that the use of a wetting agent enhances the effectiveness of $C_2N_2$ as an insecticidal dip. Cross reference is made to control of other insects (e.g. Example 36) and to control with the fumigant applied in water (e.g. Example 7). The fumigant killed insects from the Aphidae and the Pseudococcidae.

Example 18

Effect of $C_2N_2$ on Germination of Wheat and on Lipid Composition

Aim: To assess the effect of $C_2N_2$ on wheat viability and on the lipid composition of wheat.

Materials and Methods

The wheat used was insecticide free Australian Standard White (ASW, approximately 11.4% moisture content, w/w, wet basis). Portions were conditioned to equilibrium after adding appropriate quantities of water. After one week at 25±1° C., samples were found to have moisture contents of 11.4%, 13.8% and 15.5%, with corresponding equilibrium relative humidities (e.r.h.) of 46.9%, 69.3% and 79.6%. Moisture content (wet basis) was calculated from the loss of mass of ground samples by oven drying at 130° C. for 2 hours. The e.r.h. was calculated from a measured equilibrium dew point observed on a MBW cooled mirror dew point meter placed in a closed loop with a 1 kg wheat sample.

Conditioned wheat samples (30 g) were placed in 270 mL Erlenmeyer flasks (filling ratio approx 10%), equipped with a septum inlet. Fumigant was injected into the headspace, five levels of fumigant (5, 10, 20, 40 and 80 mg.$L^{-1}$) and a control were used for each of four wheat samples of different moisture content, and for three different periods of exposure (24, 48 and 96 hours) at 25±1° C. Before germination, wheat was transferred to Petri dishes and aired for 24 hours.

Germination tests were carried out according to the principles stated in International Seed Testing Association Methods. Fifty seeds were saturated with approximately 40 mL of distilled water and wrapped in 2 rolled crepe filter papers (500×330 mm each). The seeds were arranged 3 cm apart on the top half of the sheet (i.e. 250×330 mm), using a seed counting board, and the lot covered by folding the lower half over them. Each doubled sheet was saturated with water and loosely rolled from one side to the other, perpendicular to the base. It was then held together with a rubber band and put in an upright position in the germination cabinet, at 20° C. The number of germinated seeds was counted after 4 days (vigour test) and after 8 days (total germination test). Each experiment was also replicated four times.

To measure the effect of $C_2N_2$ on lipid composition, 40 g Australian Standard White (ASW, approximately 11.4% moisture content, w/w, wet basis), was fumigated at 100 mg.$L^{-1}$ in a 750 mL glass jar, with a screw-top lip fitted with a septum for 48 h, and lipids extracted with petroleum ether+butanol(2:1 v/v)/hot water saturated butanol. In addition lipids from wheat extracted by Soxlet extration with hexane and commercial wheat germ oil were fumigated with $C_2N_2$ at very high levels, and then 1 g of oil was fumigated, in a 270 mL Erlenmeyer flask, with a fumigant concentration of 100 mg.$L^{-1}$, for 48 h at 20° C. and 30° C. Lipid composition was determined by both Ultra-Violet Spectroscopy and by Fourier Transform Infra-Red Spectroscopy. For the UV, absorbance was measured at 340 nm, and the IR spectra, in carbon tetrachloride, covered the range 1000–4000 wavenumbers, with quantitation at 1740, 2850, 2930 and 3000 wavenumbers.

Results

Figure 11:
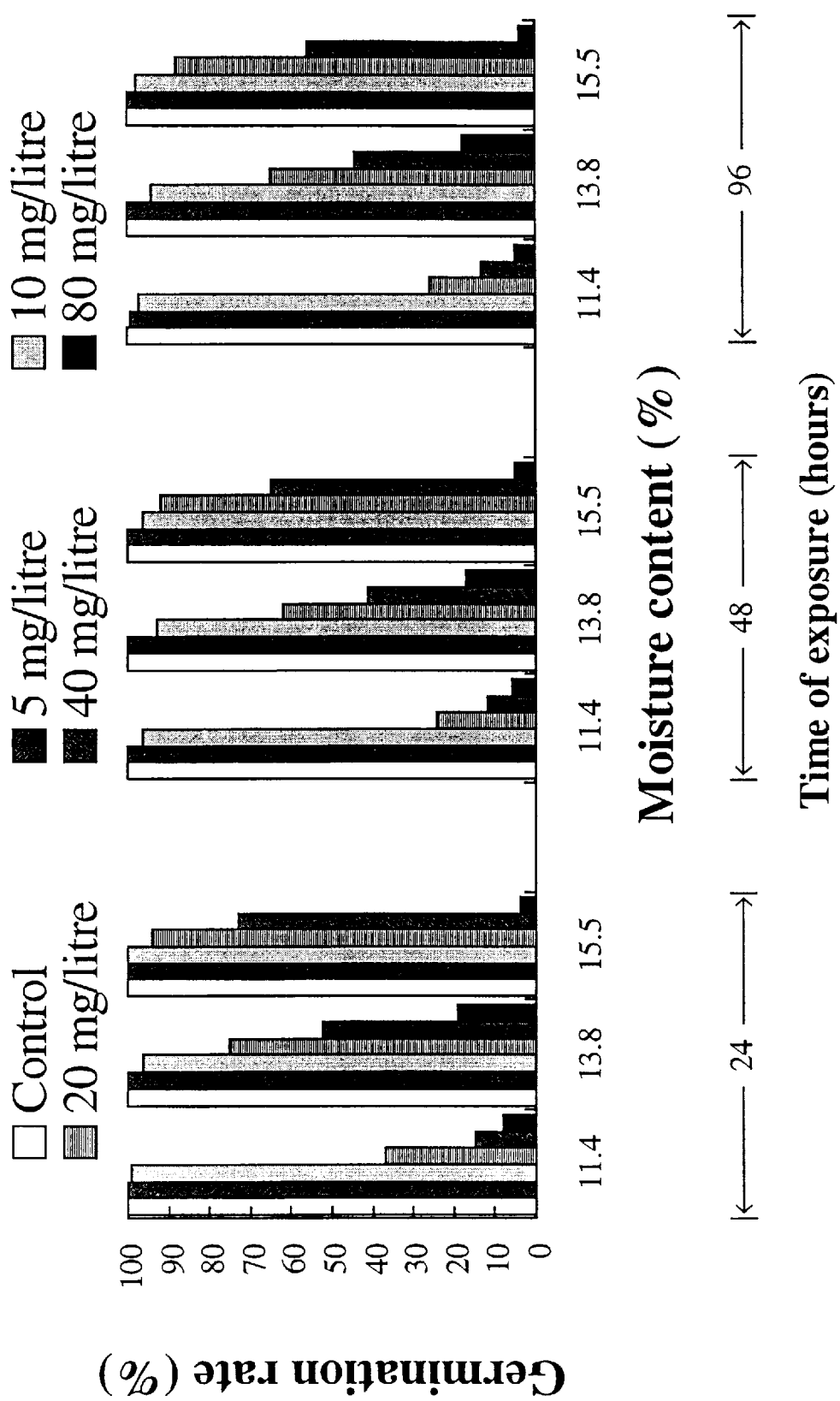
FIGS. 11, 12 and 13(*a*) to (*d*) illustrate the effects of wheat treated with $C_2N_2$.

The effect of $C_2N_2$ on vigour is summarised in FIG. 11. There was no effect at the applied concentration of 5 mg.$L^{-1}$. This corresponds to an application of 45 mg/kg(wheat). W/W, that is, 45 mg of fumigant per kg of wheat. There was a slight reduction in germination from the higher application of 10 mg.$L^{-1}$, though the effect was only significant for one of the three moistures studied.

Figure 12:
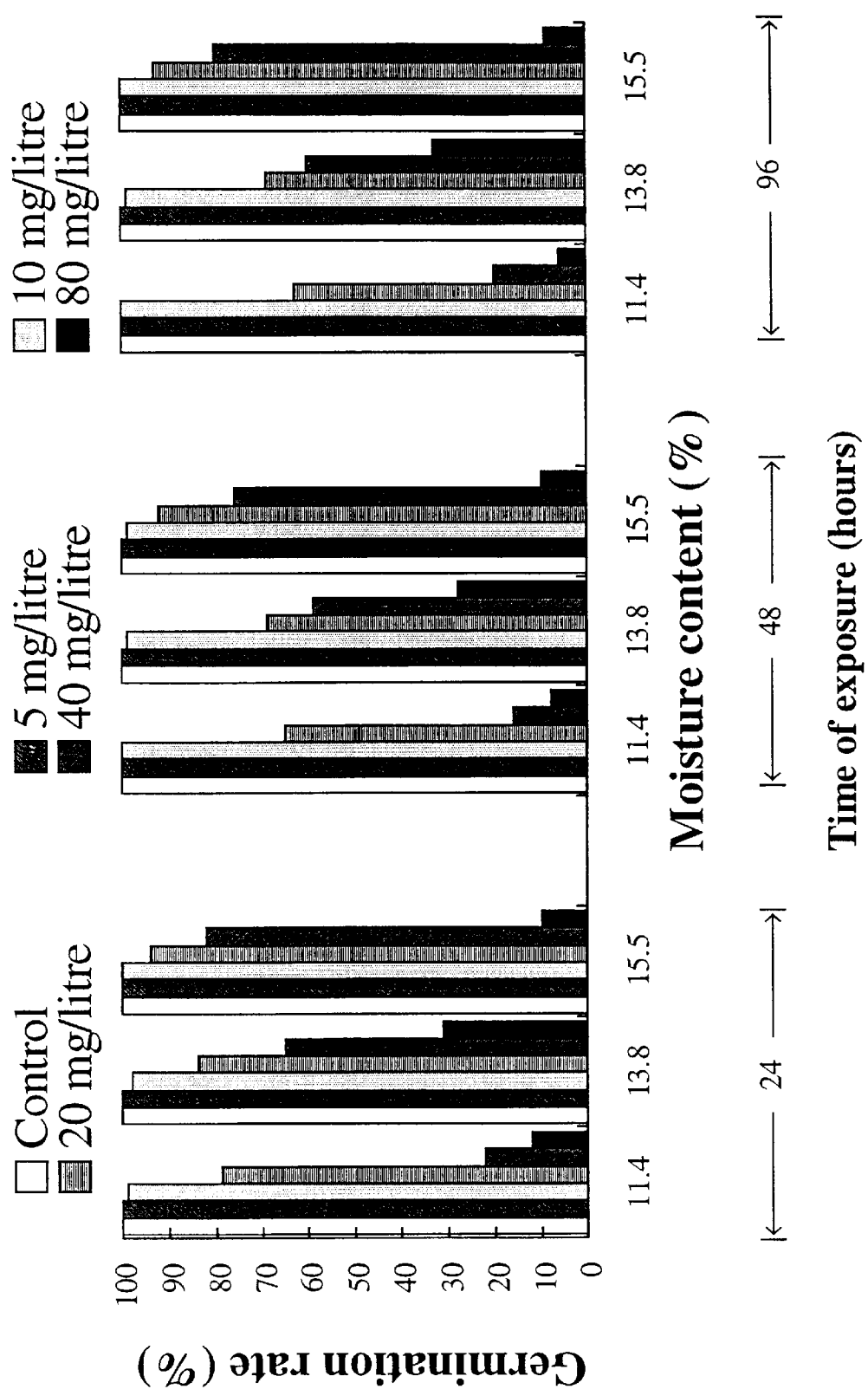
Figure 13A:
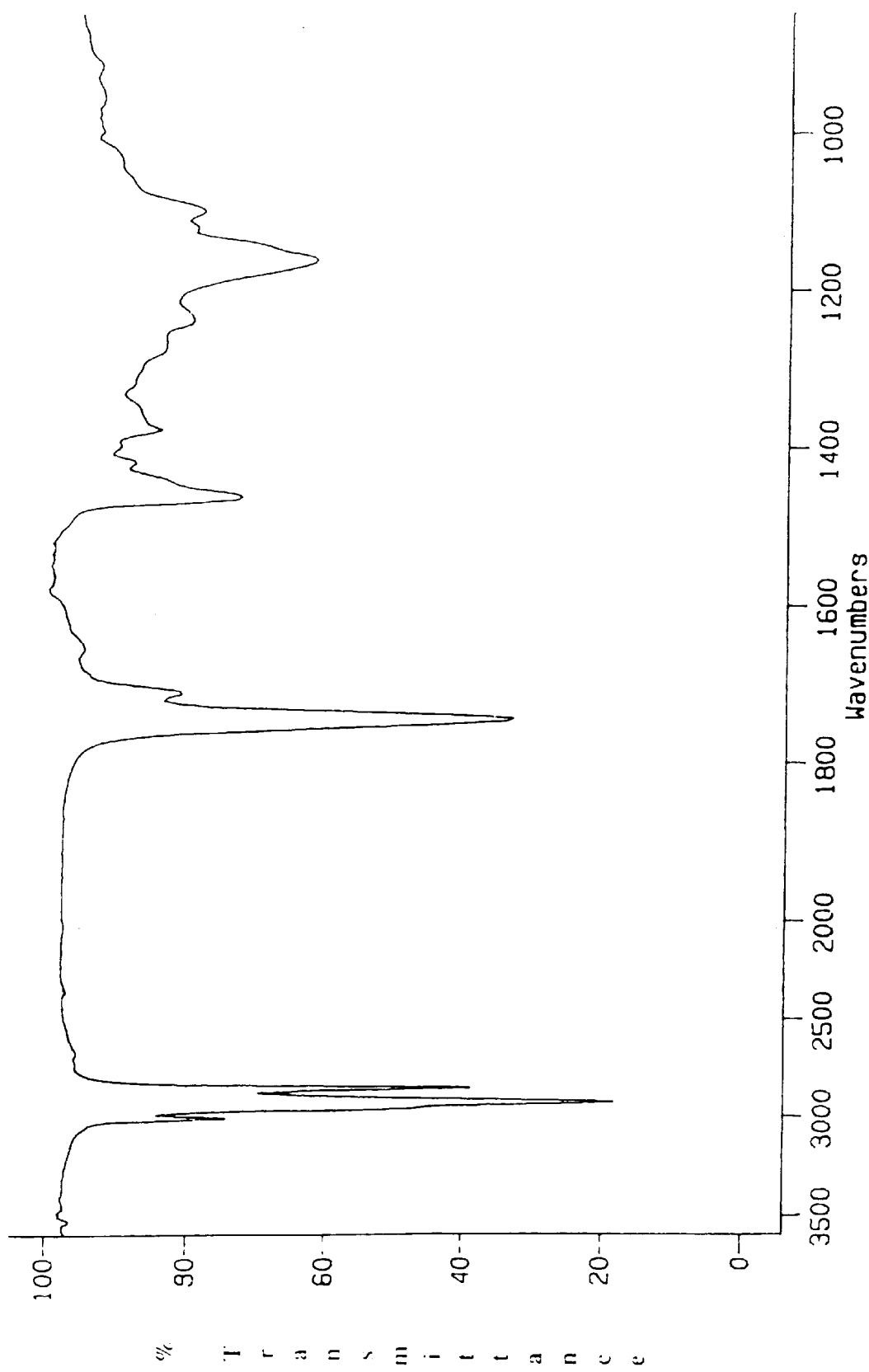
Figure 13B:
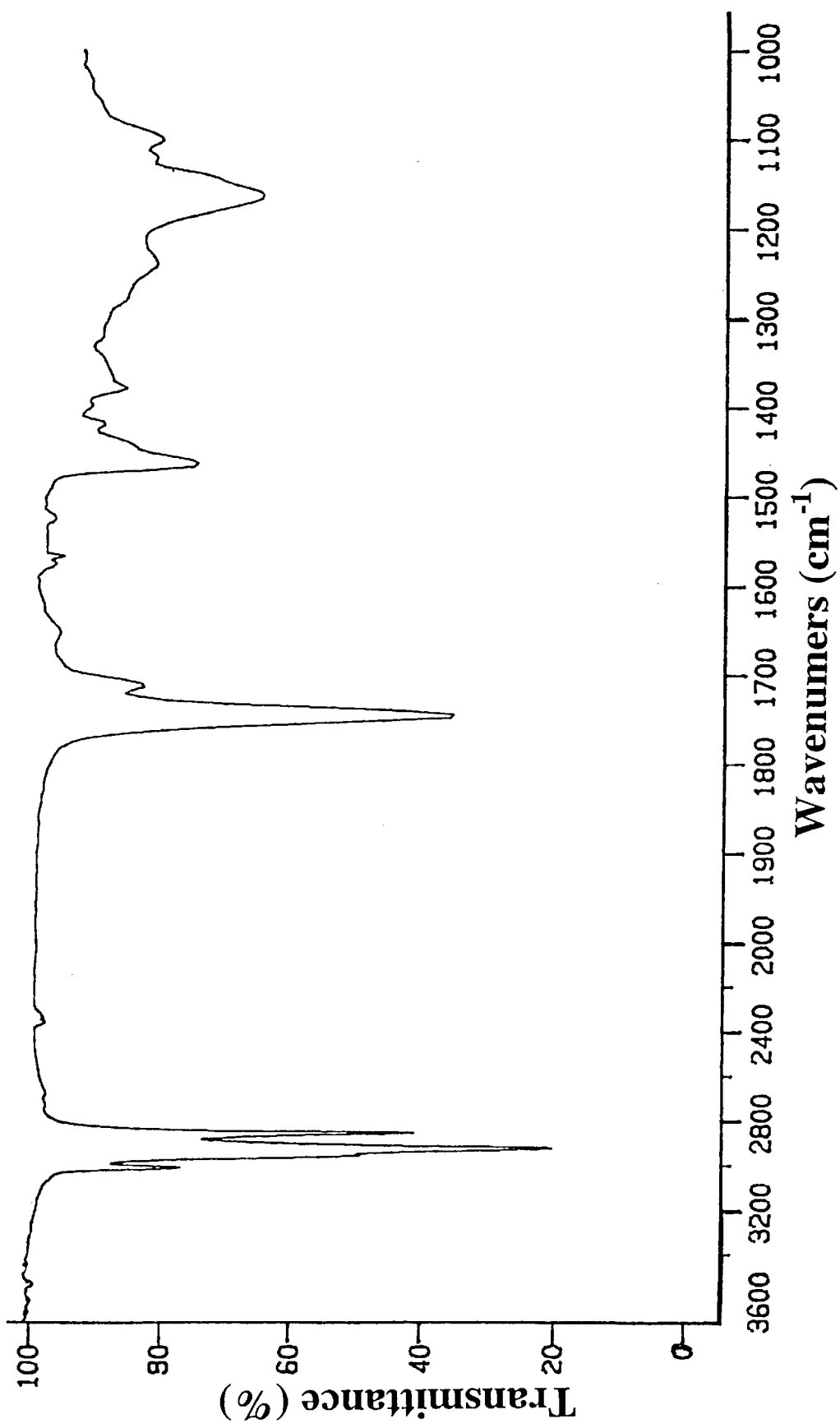
Figure 13C:
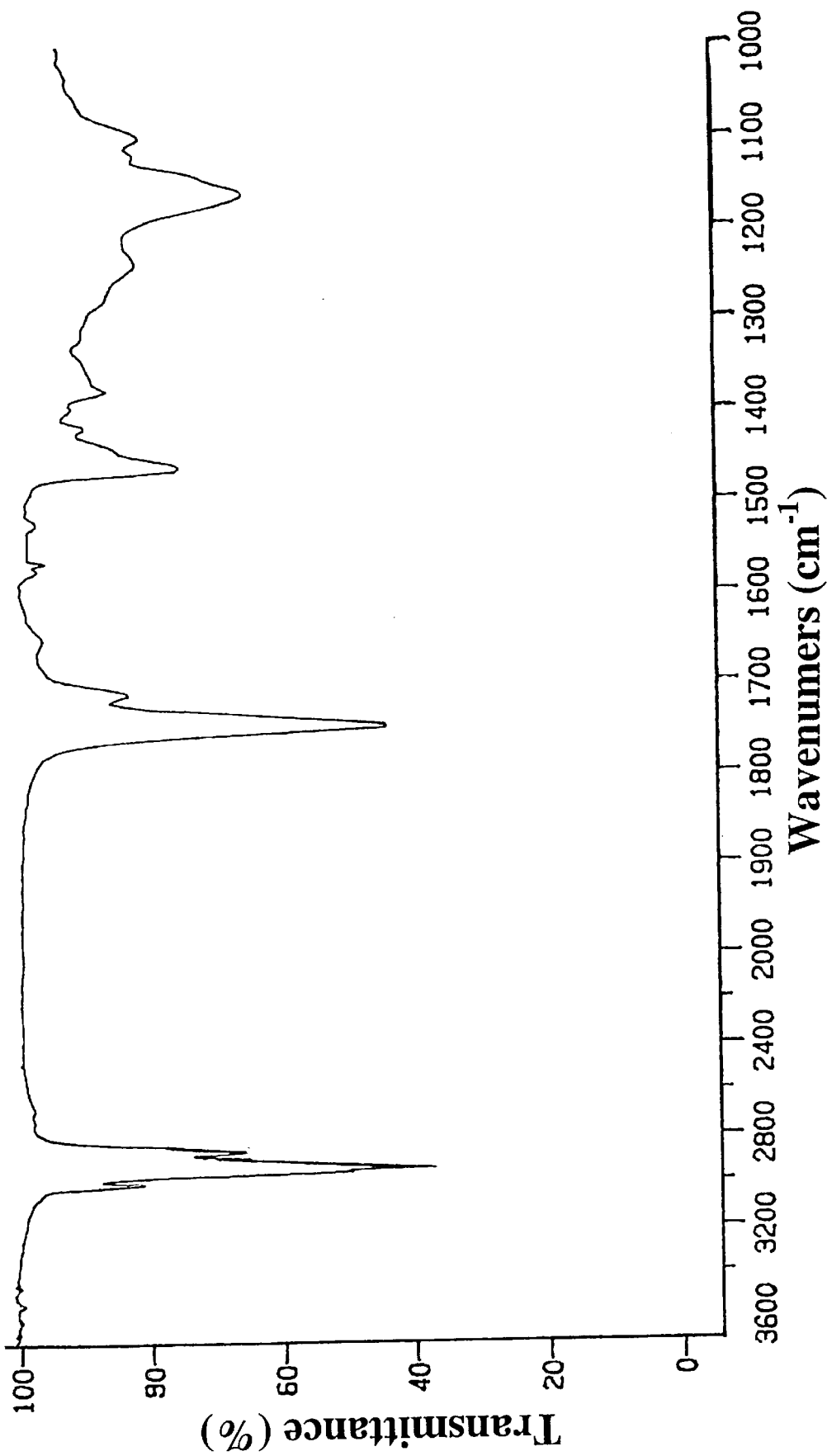
Figure 13D:
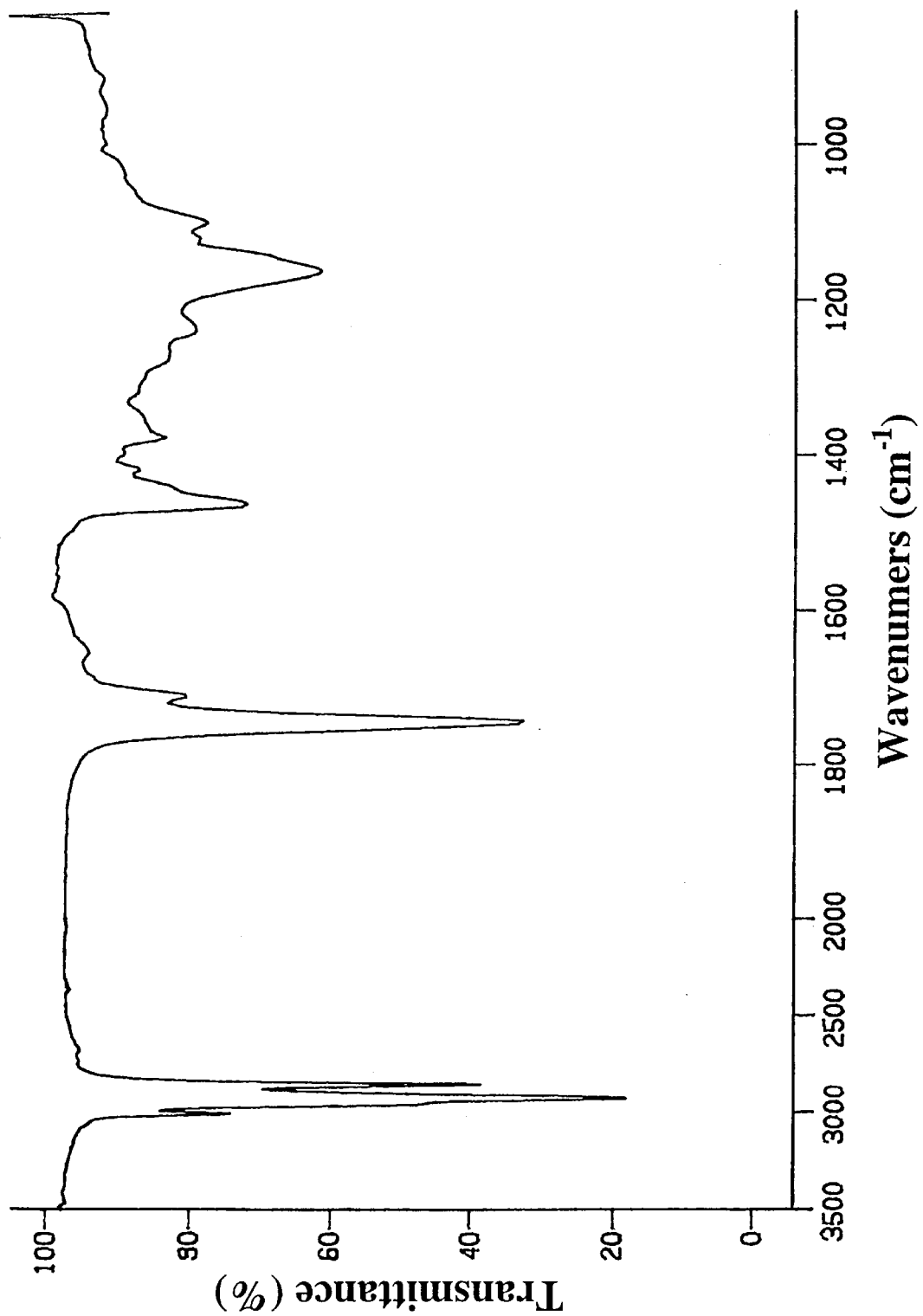

The effect of $C_2N_2$ on germination is shown in FIG. 12. There was no effect of germination at the applied concentrations of 10 mg.$L^{-1}$ (FIG. 2). This corresponds to an application of 90 mg/kg(wheat). Concentrations of 40 mg.$L^{-1}$ or above (180 mg/kg) considerably impaired germination.

The results in FIGS. 11 and 12 exhibit two unusual features. First, increasing the exposure period from 24 h to 48 h or 96 h had little effect on germination. Second, the effect of moisture content on loss of germination was contrary to expectation, in that it was less on wet than on dry grain.

There was no observed effect on lipid composition, from fumigation of wheat or oil, as assessed by UV and FTIR (FIG. 13). In the case of fumigation of oil, the amount applied was 27,000 mg of fumigant per Kg of oil. It was also, approximately, 0.1 mole of fumigant per mole of lipid, calculated as a monoglyceride, or approximately three times that molar proportion, for lipid calculated as a triglyceride.

Discussion

Although the concentration of fumigant was not measured in these experiments, it can be estimated from data obtained under similar conditions. Thus on the wheat of 11.4% moisture, and an applied concentration of 10 mg.$L^{-1}$, the concentration time product is close to 9000 mg.h.$L^{-1}$. This is several orders or magnitude above the doses needed to killed most insect species and stages. Thus, subject to further tests, results on germination are consistent with the ability to use the fumigant without affecting grain quality.

The experiment on the effect of $C_2N_2$ on lipids were conducted at extremely high levels, after experiments on wheat, at more feasible levels, showed no effect. Even at extremely high levels, no effect was observed.

Example 19

Control of Bacteria with $C_2N_2$

Aim: To determine the efficacy of $C_2N_2$ against bacteria, especially those of medical importance, and to determine whether it was effective in both aqueous and non-aqueous media.

Materials and Methods

All procedures used sterile equipment and reagents.

Three strains of bacteria were tested. These were *Bacillus cereus*, *Pseudomonas aeruginosa* and *Staphyloccus aureus*. Strains were supplied by the School of Human and Biomedical Science of the University of Canberra, and were chosen because of their importance in infection, because of their difficulty to control by other procedures and because of their different habitats.

To test the efficacy of the fumigant against bacteria in water, inoculum was placed in 2 mL of distilled water in 5 mL bottles. Two bottles were placed in a 700 mL glass jar, with a screw-top lip fitted with a septum. The fumigant was applied through the septum to give concentrations of 0, 20, 40, 80, 120 and 160 mg/L. The jar was kept at 35° C. for 20 h and 40 h. The lid was then removed, and the container aired for 4 h, before the addition of 2 mL of nutrient broth. The broth was incubated at 37° C. for 24 h, before assessment of live bacteria.

To test the efficacy of $C_2N_2$ in non-aqueous media, 7 mL of nutrient agar was placed in a 10 mL bottle and an innoculum of bacteria was placed on the ramp surface. The procedure of dosing was as described for bacteria in water.

Efficacy of the control measure was tested in 3 ways for the aqueous media.

These were:

1) the colour of the water, before addition of nutrient broth;
2) the clearness of the admixture of water and broth, after incubation;
3) Quantitative bacteria count, before plating on agar in petri dish, serial dilutions were carried on. In serial dilutions, the original inoculum was diluted out in a serial of dilution tubes. In our experiment, each succeeding dilution tube had only 10% of the number of bacteria as in the proceeding tube. That is, 20 μL of the sample were transferred of a tube containing 180 μL of sterile water.

For control in non-aqueous media, only the third procedure, namely quantitative counting after planting out on agar, was used.

Results

Aqueous medium

For bacteria in water, the nutrient broth was cloudy in the control, but clear and yellowed for all levels of fumigant in the case of *Pseudomonas aeruginosa*. Thus this strain was controlled at doses of 20 mg/L, and above, for 20 h exposure. For *Bacillus cereus*, the solution was clear and yellow at doses of 120 mg/L and above.

Visual assessment before addition of nutrient broth provided a good, and unexpected, indication of the level of control. Where mortality of bacteria was complete, the aqueous solution became yellow, whereas it remained cloudy but not yellowed when bacteria were not controlled.

Quantitative assessment after counting is recorded in Table 11.

TABLE 11

Effect of $C_2N_2$ in aqueous medium on control of bacteria, for exposure periods of 20 hours and 40 hours.

| Dose | Bacillus cereus (% control) | | Pseudomonas aeruginosa (% control) | |
|---|---|---|---|---|
| (mg/L) | 20 hour | 40 hour | 20 hour | 40 hour |
| Control | v | v | v | v |
| 20 | v | v | 100% | 100% |
| 40 | v | v | 100% | 100% |
| 80 | 10% | 30% | 100% | 100% |
| 120 | 50% | 100% | 100% | 100% |
| 160 | 100% | 100% | 100% | 100% | v - Bacteria growth normal

Non-aqueous media

Results of Quantitative assessment are shown in Table 12.

TABLE 12

Effect of $C_2N_2$ in non-aqueous media on control of bacteria for exposure periods of 20 hours and 40 hours.

| Dose | Baccillus cereus (% control) | | Pseudomonas aeruginosa (% control) | | Staphylococcus aureus (% control) | |
|---|---|---|---|---|---|---|
| (mg/L) | 20 hour | 40 hour | 20 hour | 40 hour | 20 hour | 40 hour |
| Control | v | v | v | v | v | v |
| 10 | v | v | v | 80% | v | 75% |
| 20 | v | v | 100% | 100% | 100% | 100% |
| 40 | 20% | 80% | 100% | 100% | 100% | 100% |
| 80 | 100% | 100% | 100% | 100% | 100% | 100% |
| 120 | 100% | 100% | 100% | 100% | 100% | 100% | v—Bacteria growth normal

Discussion

The fumigant controlled important strains of bacteria in both aqueous media and in non-aqueous media. This reflect the ability of the fumigant to be active in both air and water, and is based on the solubility in water and phase equilibrium between water and air. This ability to act in two phases is very useful in sterilisation in laboratories, hospitals, dental and veterinary premises, food premises and in all situations where bacteria may be found in aqueous media, non-aqueous media or a combination of both.

The bacteria tested included a Pseudomonas species, which is motile, aerobic and gram-negative, and a Staphyloccus species, which is non-motile, anaerobic and gram-positive (Blakiston, 1979). *Bacillus cereus* is a "genus causing food poisoning", and is aerobic and gram-positive (Miller and Keane, 1983). Miller and Keane describe the Pseudomonas genus as "gram-negative, strictly anaerobic bacteria, some species of which are pathogenic for plants and vertebrates". *P. aeruginosa* causes "blue pus" and "various human diseases, and *P. mallei* causes glanders, a disease of horses which is communicable to man" (Miller and Keane, 1983, p929). The Staphyloccoccus genus are "the most common cause of localised suppurating infections" (Miller and Keane, 1983, p1057). According to Blakiston, 1979, *S. aureus* "is responsible for a variety of clinical disturbances in man and animals, such as abscesses, endocarditis, pneumonia, osteomyelitis, and septicemia" (p1288) and *P. aeruginosa* is "the causative agent of various suppurative infections in man".

From other work in other documents, $C_2N_2$ can be used for general disinfestation, including moulds and invertebrates.

Cross references: Cross references are made to Example 5, concerning storage of meat, to Example 6, re: fruit. The ability to be active in water is covered in other Examples, and movement through water (Example 22) is relevant.

Example 20

Efficacy of $C_2N_2$ Against Nematodes

Aim: to determine the efficacy of $C_2N_2$ against nematodes.

Materials and Methods

Nematodes, in 2 mL of water, were placed in an Erlenmeyer flask, of measured capacity 11.5 mL and the flask was fitted with a Mininert valve. $C_2N_2$ gas, of measured concentration but typically close to 90%, V/V, and free of hydrogen cyanide (<0.5%) was injected into the flask. Alternatively, $C_2N_2$ in aqueous solution (0.2 mL) was injected into the flask. The flask was held at room temperature, in a room air-conditioned to 20° C. to 22° C. The species of nematode tested was infective juveniles of *Steinernema carpocapsae* strain BW.

In experiment 1, gas concentrations in the air over the water were measured at timed intervals, using a thermionic specific detector, after separation on a BP-624 megabore column. Concentrations were plotted against time after addition, and the area under the curve was manually measured to provide an estimate of the (concentration×time) product in the headspace.

After exposure for 22 h, the flasks were opened and the gas allowed to air. Mortality was assessed under a microscope 24 h after initial addition of fumigant.

Results

Concentrations of $C_2N_2$ in the headspace 5 minutes after gas addition were typically only one third of the nominal concentration, calculated on the assumption of no absorption in water. This is consistent with other results on the partitioning of $C_2N_2$ between water and air, which show strong sorption in water. For example, for a nominal concentration of 3.46 mg/L, headspace concentrations, 5 minutes after addition of fumigant, were 0.85 mg/L and 0.58 mg/L in fully replicated experiments. Concentrations declined rapidly in the headspace, in an exponential manner. For example, the half life from a nominal concentration of 3.48 mg/L was 0.94 h, the half life from a nominal application of 8.7 mg/L was 2.7 H and the half life from a nominal application of 17.4 mg/L was 5.2 h. Thus the headspace concentration over water, and the (concentration×time) product, varies in an unexpected way. This is shown in Table 13.

Nematodes died quickly after exposure to $C_2N_2$, as shown in Table 14. For example, a nominal application of 3.48 mg/L killed 404/404 nematodes of *S. carpocapsae*, as against a control mortality of only 5/462.

TABLE 13

Applied quantities of $C_2N_2$, half-life of this fumigant in the headspace, and concentration x time (CT) products in the headspace, for the system of 2 mL of water in an 11.5 mL erlenmeyer flask.

| Amount added (mg) | Half-life (h) | (CT) product (mg · h/L) |
|---|---|---|
| 0.40 | 0.94 | 0.72 |
| 1.0 | 2.7 | 4.0 |
| 2.0 | 5.3 | 16.8 |

TABLE 14

Toxicity of $C_2N_2$ to nematodes

| Experiment Number | Species | Applied amount (mg) | Method of application | Acute Mortality Dead | Live |
|---|---|---|---|---|---|
| 1 | S. carpocapsae | 0 | — | 5 | 212 |
| 1 | " | 0 | — | 0 | 243 |
| 1 | " | 0.04 | gas | 200 | 0 |
| 1 | " | 0.04 | " | 204 | 0 |
| 1 | " | 0.1 | " | 153 | 7 |
| 1 | " | 0.1 | " | 200 | 0 |
| 1 | " | 0.2 | liquid | 197 | 0 |
| 1 | " | 0.2 | gas | 218 | 0 |
| 2 | " | 0 | — | 0 | 266 |
| 2 | " | 0 | — | 0 | 228 |
| 2 | " | 0.02 | " | 201 | 0 |
| 2 | " | 0.02 | " | 266 | 0 |
| 2 | " | 0.008 | " | 17 | 245 |
| 2 | " | 0.008 | " | 1 | 267 |
| 2 | " | 0.004 | " | 3 | 282 |
| 2* | " | 0.004 | " | 5 | 277 |

Example 21

Application of $C_2N_2$ to Control Moulds

Aim: to determine the toxicity of $C_2N_2$ to moulds present in wheat grains.

Materials and Method

Wheat, Rosella variety, unsterilised, at 16% and 22% moisture content.

Gas tight 120 mL bottles with crimp-top mininert valves.

Sterilised plastic petri dishes containing Oxoid nutrient agar.

Large glass desiccators.

For each moisture content, 20 grams of wheat was weighed into each 120 mL bottle. The bottles were sealed with the mininert valves and dosed with $C_2N_2$ to give concentrations of 18, 35, and 70 mg L$^{-1}$. Controls with no fumigant added were sealed as well. All bottles were stored at 25° C. for exposure periods of 6 hours and 24 hours. Each treatment was carried out in duplicate. The total procedure was completely replicated.

Fumigant concentrations were determined by gas chromatography using a Varian 3300 gas chromatograph with a Thermionic Specific Detector, a DBwax column with internal diameter of 0.53 mm, and an isothermal column temperature of 60° C. When exposures were complete, the bottles were opened and the wheat aired for a few minutes. Samples of 10 grains from each bottle were then aseptically transferred to the agar plates. These were stored at 25° C. in desiccators with a water reservoir for 4 days. After 4 days the plates were removed and the grains assessed for mould growth and grain germination.

Moulds present in the control wheat were determined that "the fungi present in the wheat, and the level of contamination, are typical of many samples of Australian wheat with *Alternaria infectoria* (not a mycotoxin producer) and *A. alternata* (potentially mycotoxigenic) being the dominant flora." The % contamination of grains was 78%, for *A. infectoria*, 17% for *A. alternata*, 4% for *Epicoccum nigrum* and 1% for each of Drechslera sp., Cladosporium sp. and Penicillium sp.

Results

Figure 14A:
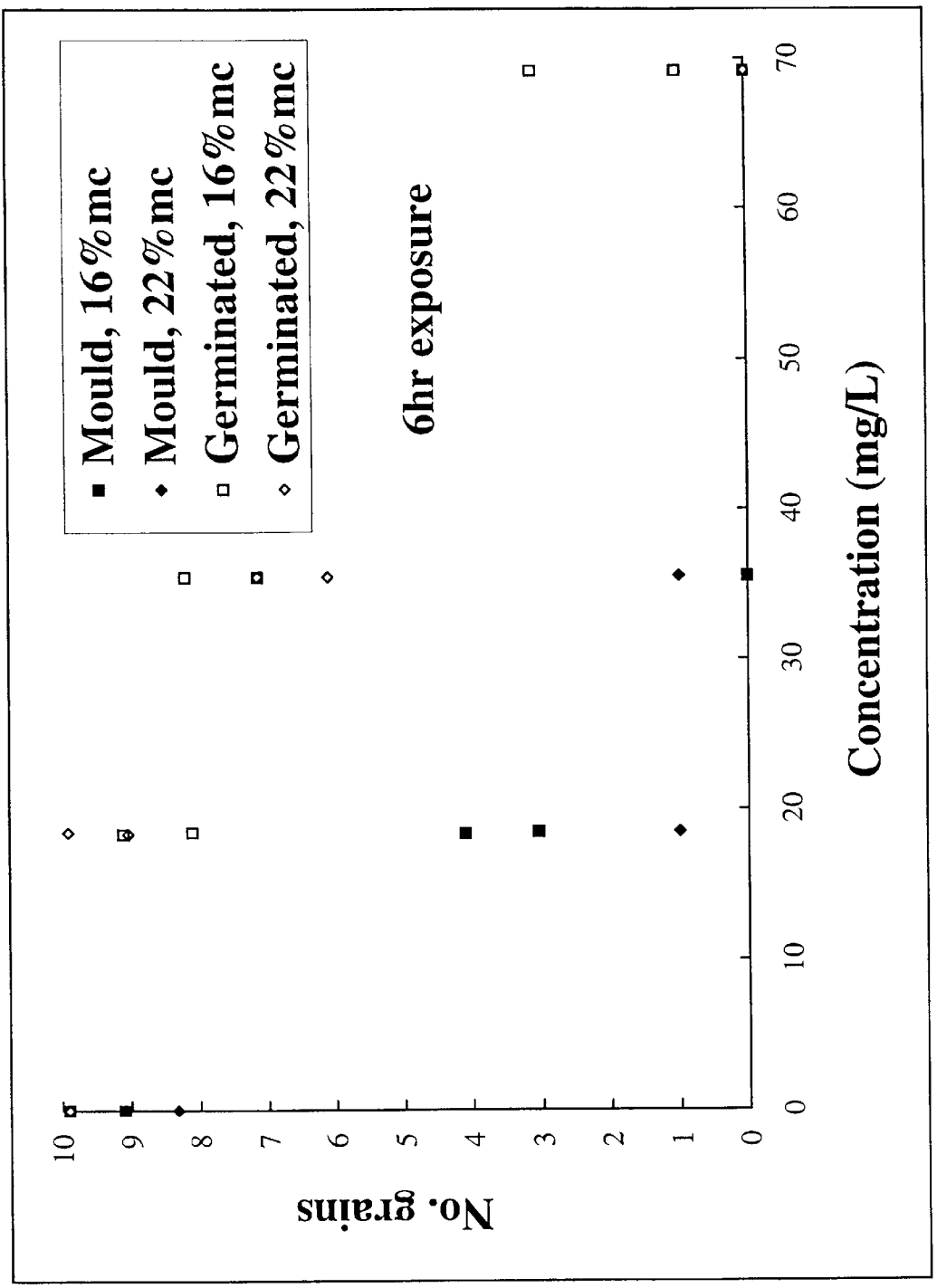
FIGS. 14(*a*) to (*c*) show the toxicity of $C_2N_2$ to moulds present in wheat grains.
Figure 14B:
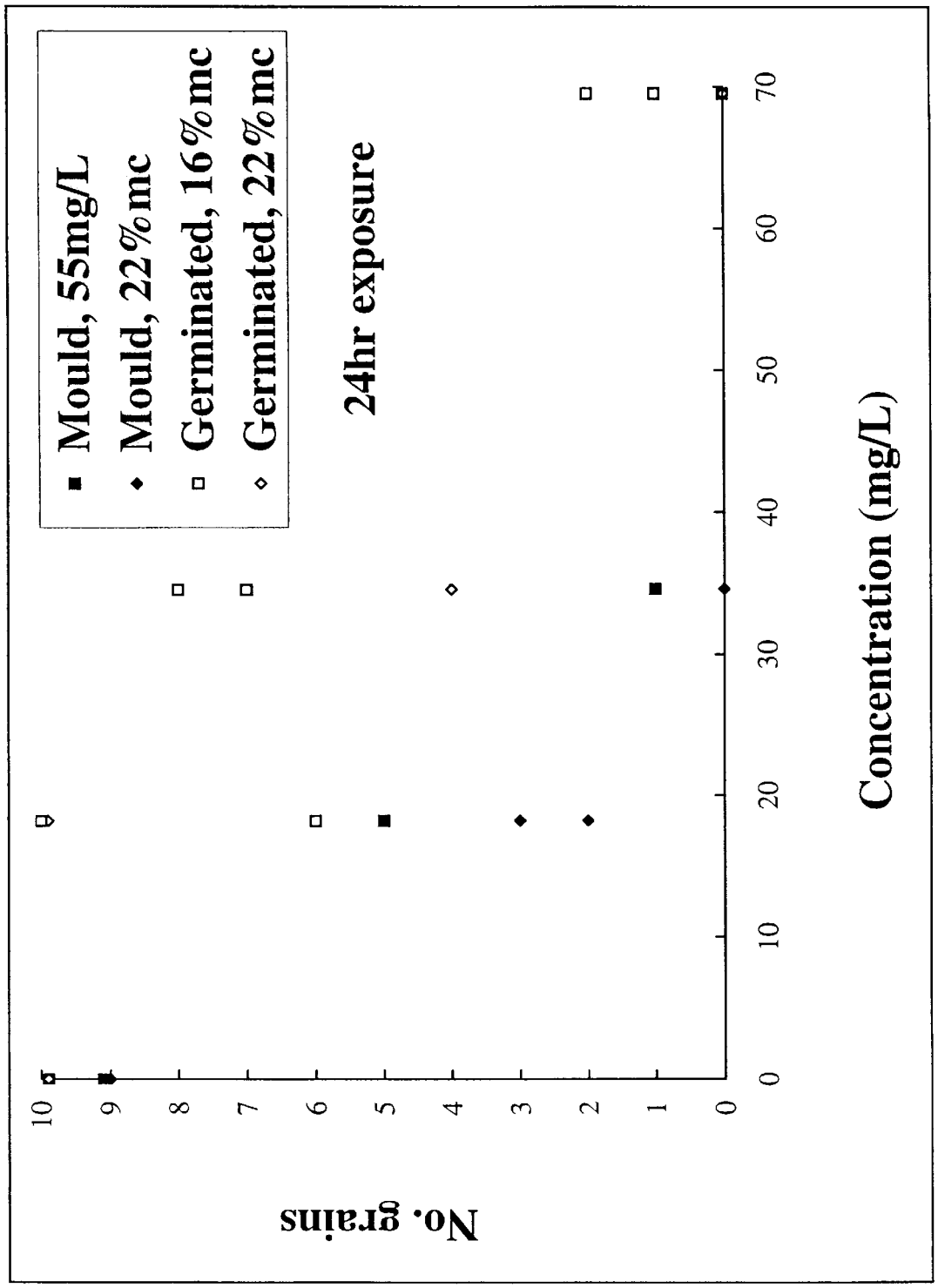
Figure 14C:
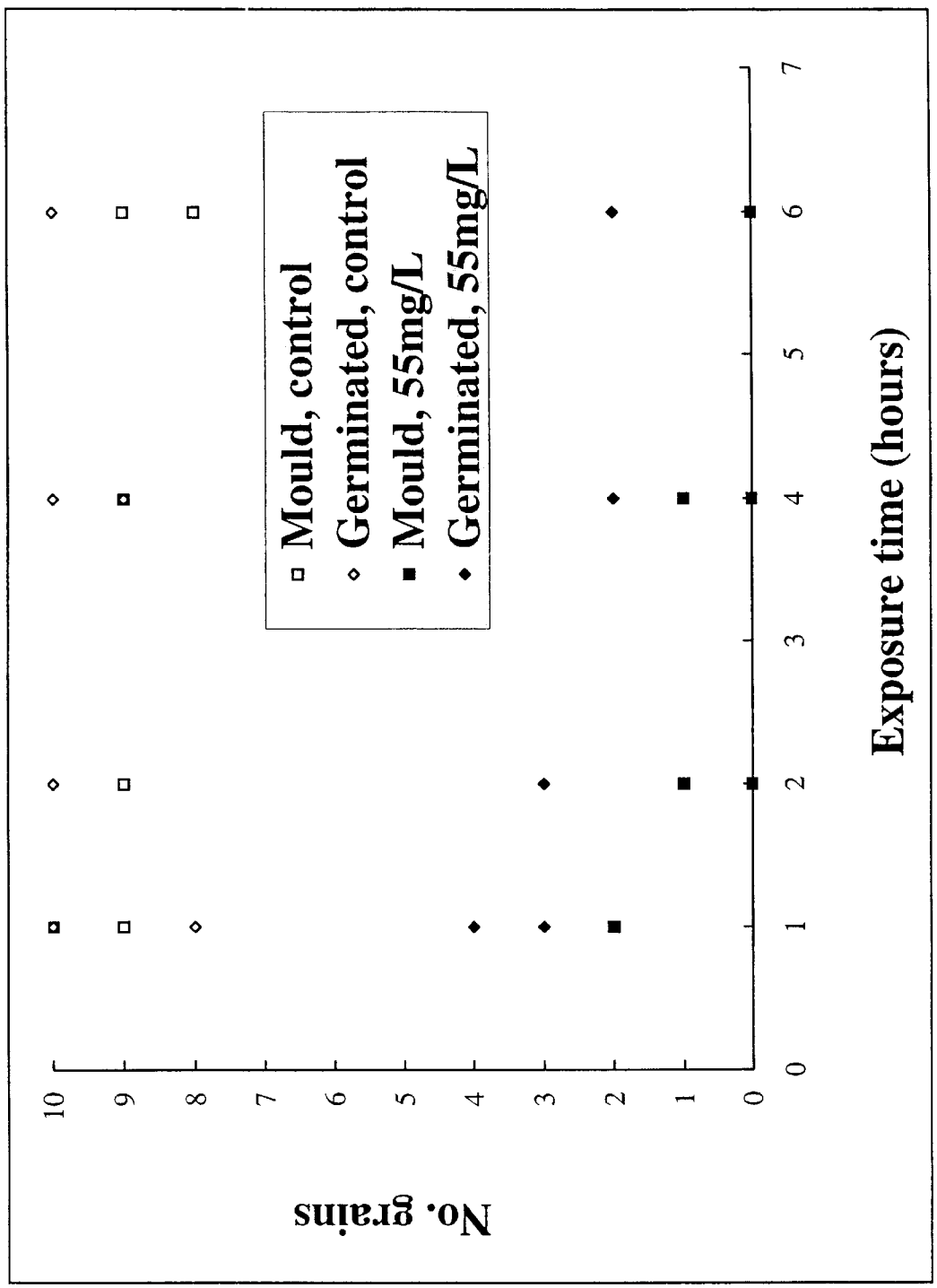

The effect of exposure for 6 h and for 24 h is shown in FIGS. 14(a) and 14(b). A concentration of 70 mg L$^{-1}$ of $C_2N_2$ on 20 grams of wheat killed the moulds present in the grain and also markedly reduced the germinability of the grain. A concentration of 35 mg L$^{-1}$ of $C_2N_2$ killed over 90% of the moulds present in the grain but reduced the germinability only slightly. A concentration of 18 mg L$^{-1}$ of $C_2N_2$ killed more than half the moulds present and had no effect on the germinability of the grain. The different moisture contents of 16 and 22% had no obvious effect on $C_2N_2$ toxicity at these concentrations. Neither did the different exposure periods of 6 and 24 h. The effect of shorter exposure periods to a concentration of 55 mg L$^{-1}$, is shown in FIG. 14(c).

Discussion

The fumigant $C_2N_2$ can be used for mould control in various ways, according to the desired effect. Thus it can completely kill moulds on wet grain, but at the cost of reduced germination, or largely suppress moulds, without reducing germination. Each option would be desirable under certain circumstances. For example, complete suppression would be desirable for grain to be held for considerable periods. Partial mould control would be useful where the aim was short term preservation, to enable, e.g. grain to be held for a longer period before drying or cooling.

Example 22

Movement of $C_2N_2$ Through Water

Aim to determine whether $C_2N_2$ moves through water, such that, e.g., the fumigant could be applied at one side of a water trap and move to the other side.

Materials and Methods

The apparatus comprised a glass U-tube, of height 140 mm, and internal diameter 18 mm, and a sampling septum at each end of the U-tube. Water was placed in the U-tube to a depth of 30 mm, such that water covered the bottom and part of the side arms.

$C_2N_2$ (1.5 mL 80%) was injected into one arm (called A-I) of the U-tube after removal of an equivalent volume of air. The fumigant was measured, at timed intervals, at each sampling septum, i.d. in each arm (A-I and A-II) of the U-tube.

40 mL water was placed in a 270 mL Erlenmeyer flask, equipped with a septum inlet. $C_2N_2$ (2 mL 80%) was injected into the headspace. The fumigant was measured at both headspace and water, at time intervals. After 90 hours, two flasks water were transferred to two 100 mL volumetric flasks, one of them was stirred, water samples were taken from the bottom of the flasks and the concentration of $C_2N_2$ in water and in the headspace was measured.

Experiment were conducted in an air-conditioned room, at an average temperature of approximately 22° C.

The fumigant was determined by gas chromatography, on a Varian 3300 Gas Chromatograph equipped with a Thermionic Specific Detector, after separation on a column DBwax, internal diameter 0.53 mm.

Results

Figure 15:
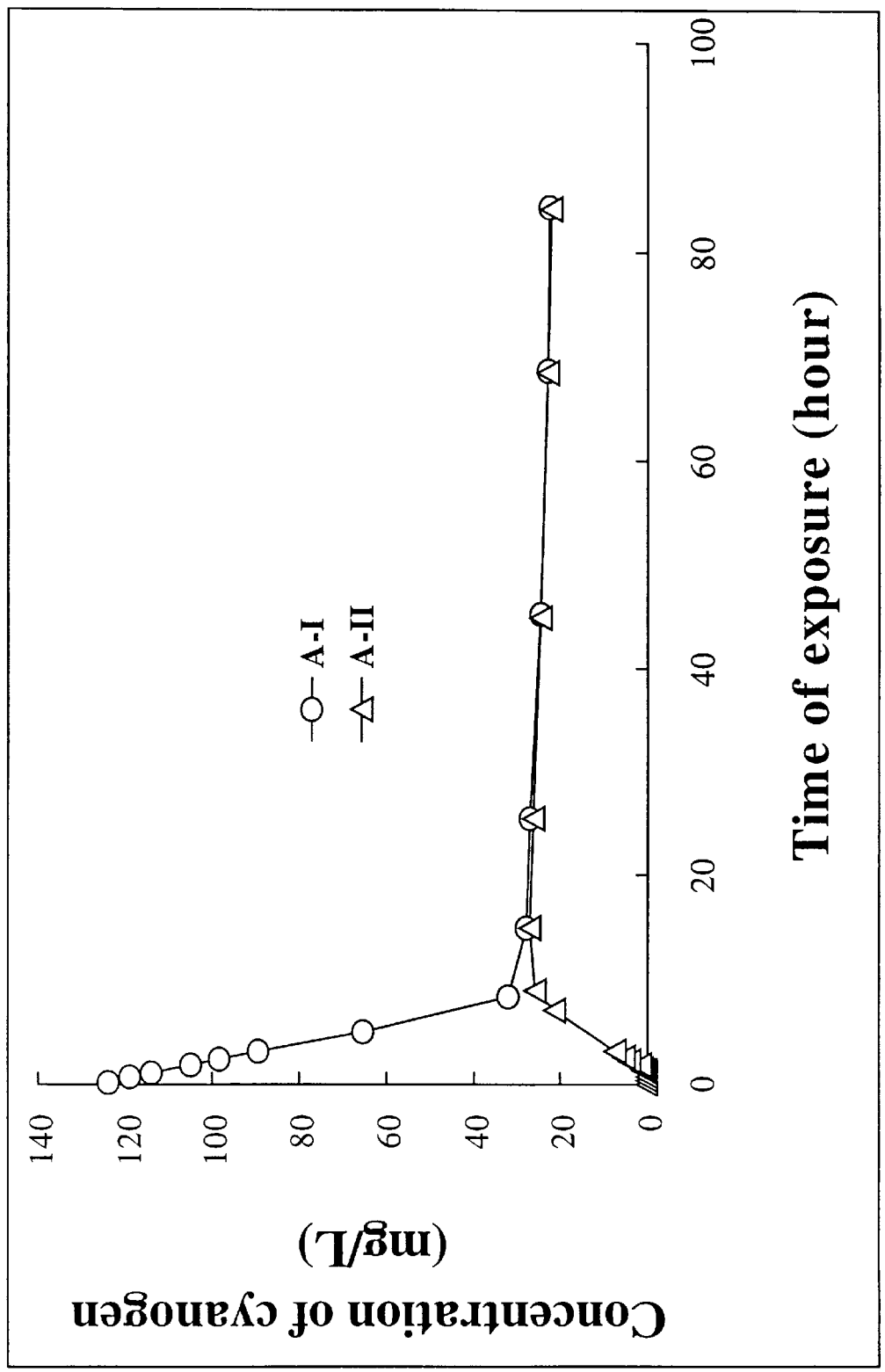
FIGS. 15 to 17 show the movement of $C_2N_2$ through water.

Movement of $C_2N_2$ through water was rapid. The system came to equilibrium after approx 10 hours (FIG. 15). The concentration of $C_2N_2$ in the headspace of each arm was 27 mg.L$^{-1}$ at equilibrium. The results in FIG. 15 shown that increasing the exposure period until 90 hours had very little effect on concentrations.

The calculated amount of $C_2N_2$ applied with 2.78 mg. The amount in the water was 1.3 mg at 90 h, and the amount in the headspace of the arms were 1.1 mg at 90 h. Thus the fumigant is relatively stable in distilled water.

Figure 16:
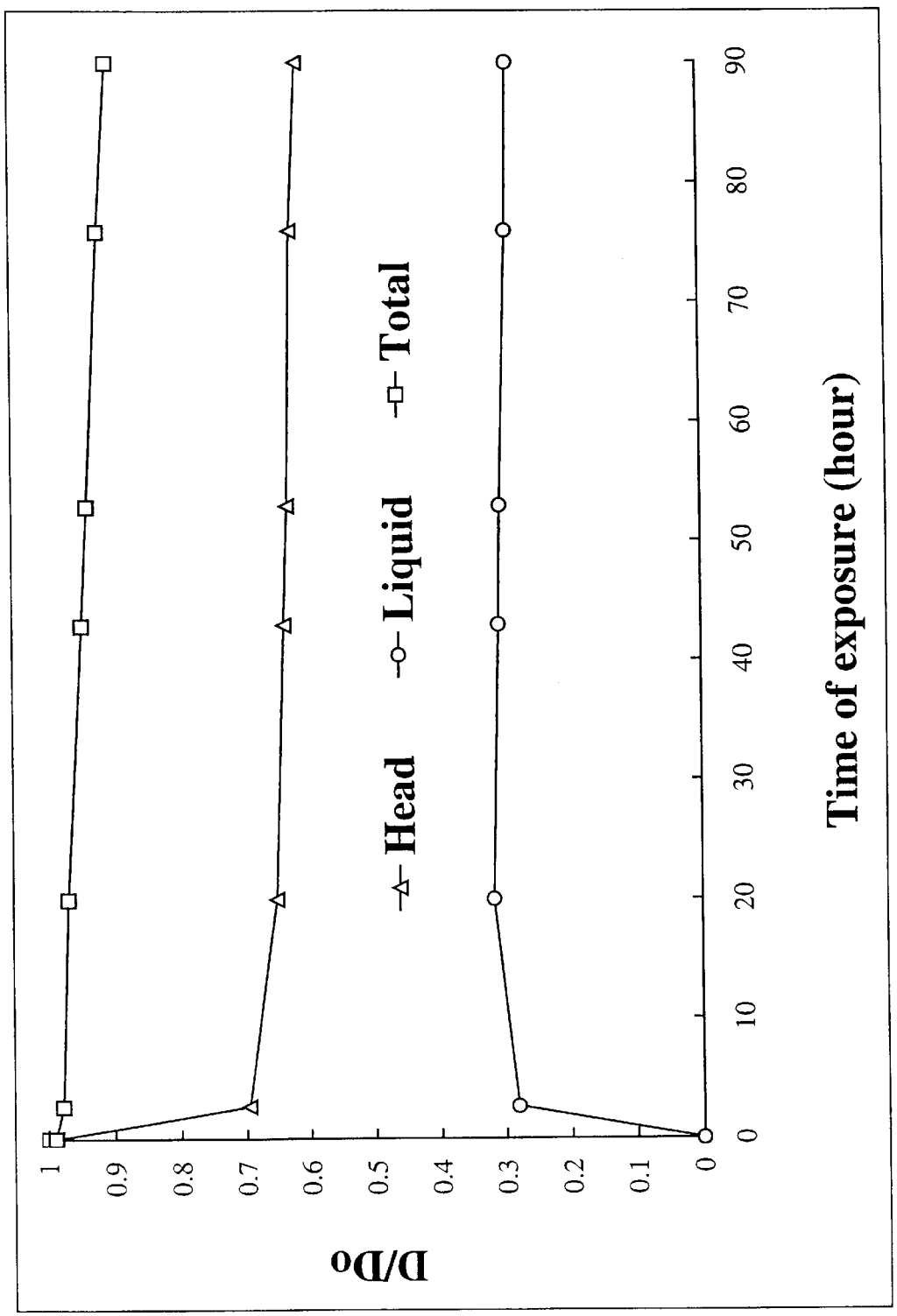

The distribution of $C_2N_2$ in water is shown in FIG. 16. After 10 hours, the system came to equilibrium. During the experiment period the total recovery was larger than 90%.

Figure 17:
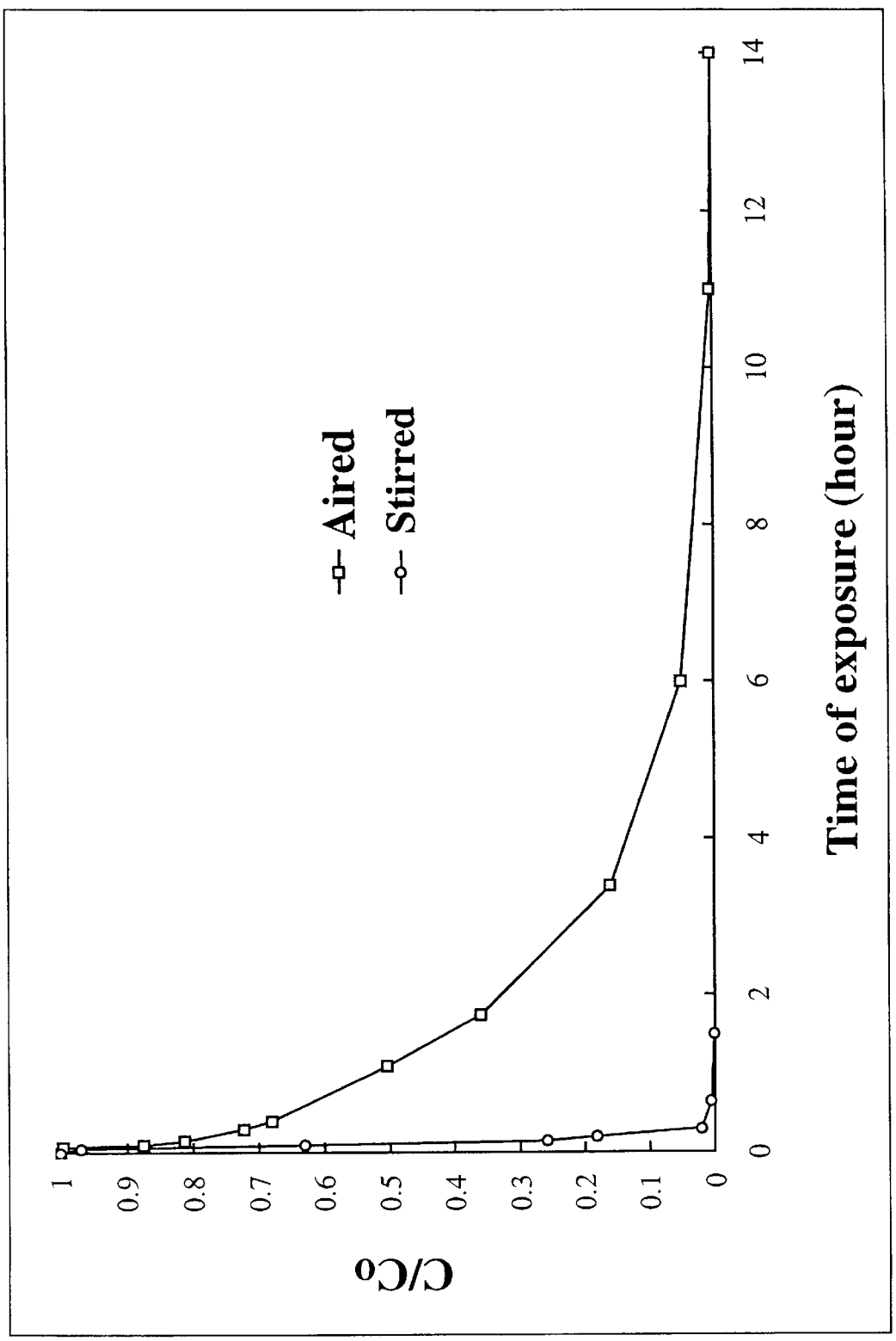

In experiments where $C_2N_2$ in water was rapidly transferred to a container, it was very rapidly released from water (FIG. 17), especially when the water was stirred The $C_2N_2$ concentration in the water and the headspace above the water became very low after stirring 0.2 h (e.g. less than 5 ppm. V/V. in the headspace) and it was lower than 10 ppm. V/V in the headspace after airing 2 h. Release of fumigant from the water was quantiative (greater than 99%).

Discussion

The movement of $C_2N_2$ through water to establish a toxic concentration at the other end of the water is a novel method of application of a fumigant gas. It relies on the solubility of the fumigant in water and its relative stability in water. These items are discussed in Example 31.

This novel method of application is important in situations where access may be difficult, especially where there is a water barrier to movement of air and gas. This situation is the normal one in water and sewerage pipes, which incorporate a water trap, typically in the form that resemble a U-tube, though usually with arms of unequal length. The novelty of the method is the ability to move through water to achieve high concentrations of the fumigant.

This ability to move through water is especially important for control of bacteria and viruses in water and sewerage systems, and for other situations where there is a water barrier. These include syringes and needles, which may contain a water barrier to gas movement, tubing, such are is used in dialysis and, more generally, in catheters, and a whole range of medical, dental, veterinary and scientific equipment.

The release of $C_2N_2$ from water, in an open container, can be used to apply the fumigant in water into a sealed space, which will result in release of the fumigant as a gas.

Example 23

The Mammalian Toxicity of Cyanogen

The toxicity of cyanogen is summarised in Sax and Lewis (1989). Fuller data are available, e.g. in a criteria document from the (U.S.A.) National Institute for Occupational Health and Safety (NIOSH: GT 1925000).

Cyanogen has worker safety limits (Threshold Limit Values) of 10 ppm (22 mg.m$^{-3}$) in both the USA and Germany. It has a (US) Department of Transport Number (1026) and these are generally internationally recognised.

Sax and Lewis (1989) summarise the toxicity as follows: "A poison by subcutaneous and possibly other routes. Moderately toxic by inhalation. Human system is effects by inhalation: damage to the olfactory nerves, and irritation of the conjunctiva". It appears that eye irritation is the first symptom of exposure to cyanogen, with the lowest effect observed after a 6 minute exposure to 16 ppm. This eye irritancy at a low dose may well be useful as a warning, but the only safe method relies of concentrations in the work space being below the TLV.

The TLV for cyanogen is 33 times higher than the TLV for phosphine, but the normal dose will not be 33 times as high, and the exposure period for cyanogen will be much shorter than for phosphine. It would appear, subject to careful checks in the workspace, that procedures that enable safe practices with phosphine will also enable safe practices with cyanogen.

Cyanogen contains a high latent heat, and is similar to acetylene in this regard. It is potentially explosive with powerful oxidants, and cylinders of gas should not be mixed with reactive chemicals. However, its lowest explosive limit in air is 6.6%, V/V (approximately 150 g. m$^{-3}$), which is considerably above the fumigant concentrations.

Example 24

Rates of Sorption of $C_2N_2$ in Wheat

Aim: To determine the rate of sorption of $C_2N_2$ into grain for different filling ratios and moisture contents.

Materials and Methods

Australian standard soft wheat (Rosella) of 11.6% moisture content, wet weight basis, was used for the 25%, 50% and 95% filling ratio sorption experiments. This wheat was moisture adjusted to give the 10%, 12% and 14% moisture content stocks which were left to equilibrate for a minimum of two weeks prior to fumigation.

$C_2N_2$ was applied to give concentrations of 6.73 mgL$^{-1}$, 13.38 mgL$^{-1}$ and 12.62 mgL$^{-1}$, for the 25%, 50% and 95% filling ratios respectively, in 120 ml bottles fitted with Mininert valved lids. Concentrations of 13.94 mgL$^{-1}$ 13.46 mgL$^{-1}$, 13.96 mgL$^{-1}$ were used for the 10%, 12% and 14% moisture content samples respectively. All sorption samples were made in triplicate and fumigant concentrations were determined at frequent timed intervals. Fumigant concentrations were detected by injection of 20 μL aliquots on a Varian 3300 Gas Chromatograph equipped with a Thermionic Specific Detector, after separation on a Dbwax column of 0.53 mm internal diameter.

Results

Figure 18:
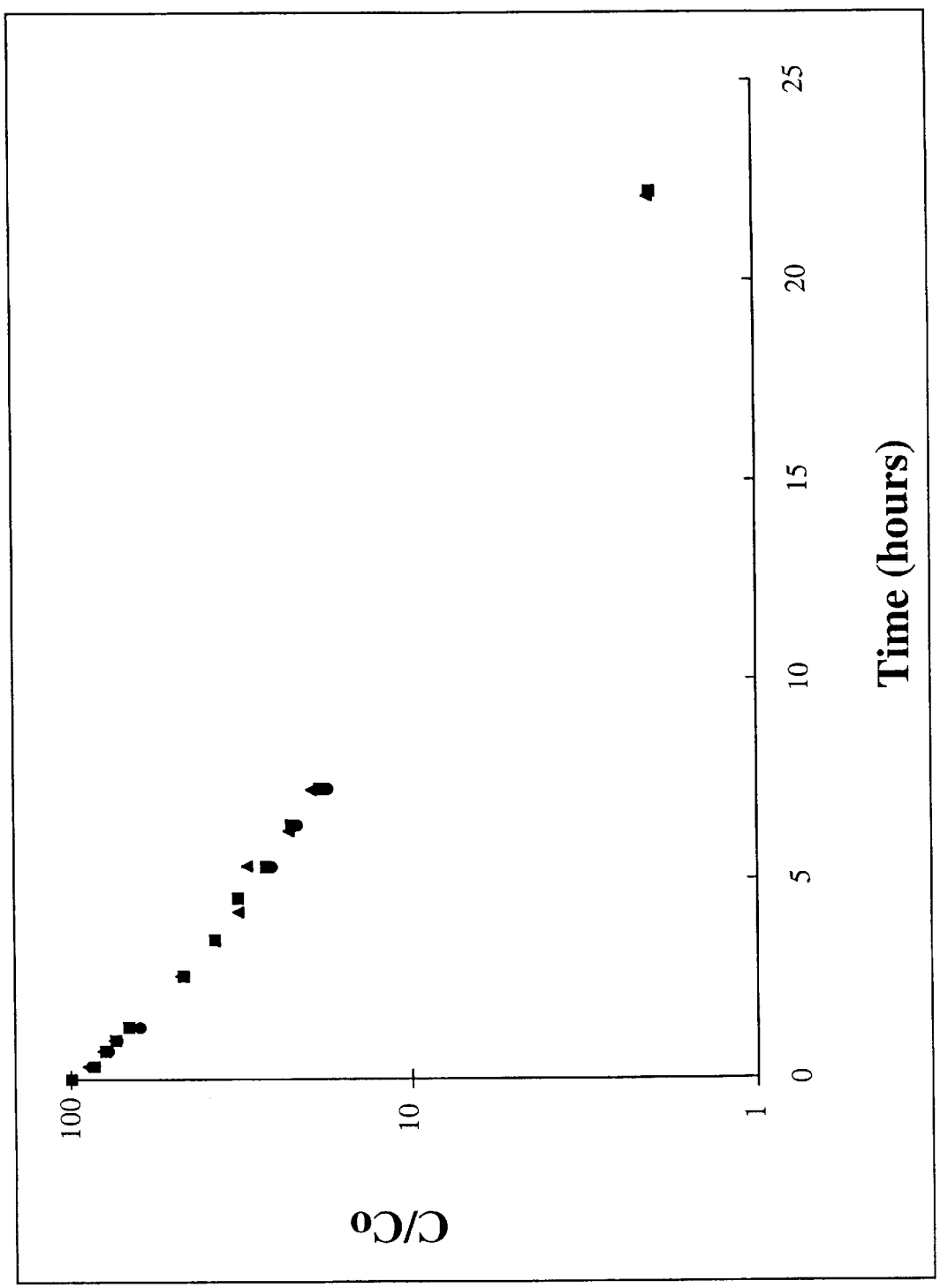
FIGS. 18 to 23 illustrate the rates of sorption of $C_2N_2$ in wheat.
Figure 19:
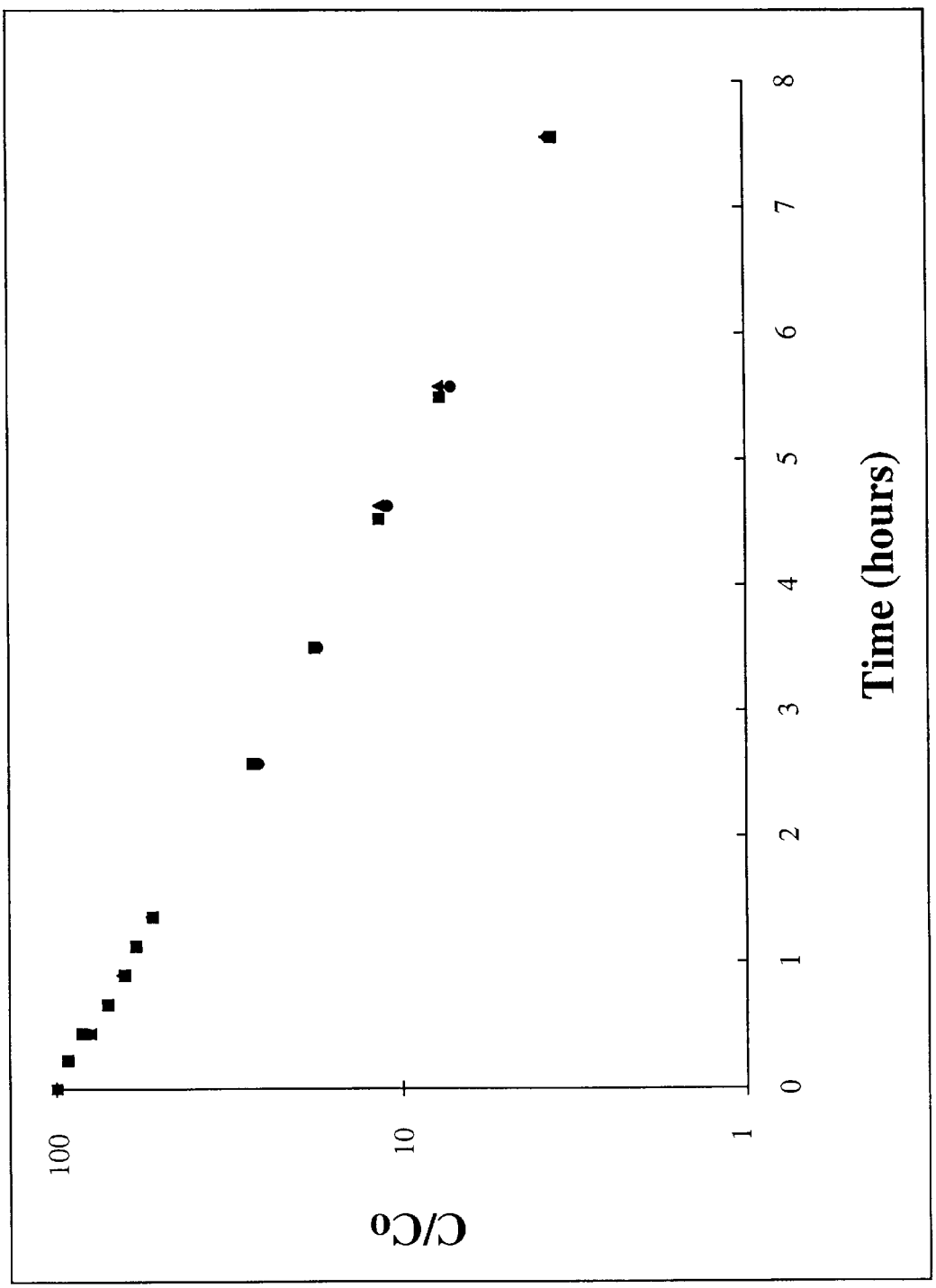
Figure 20:
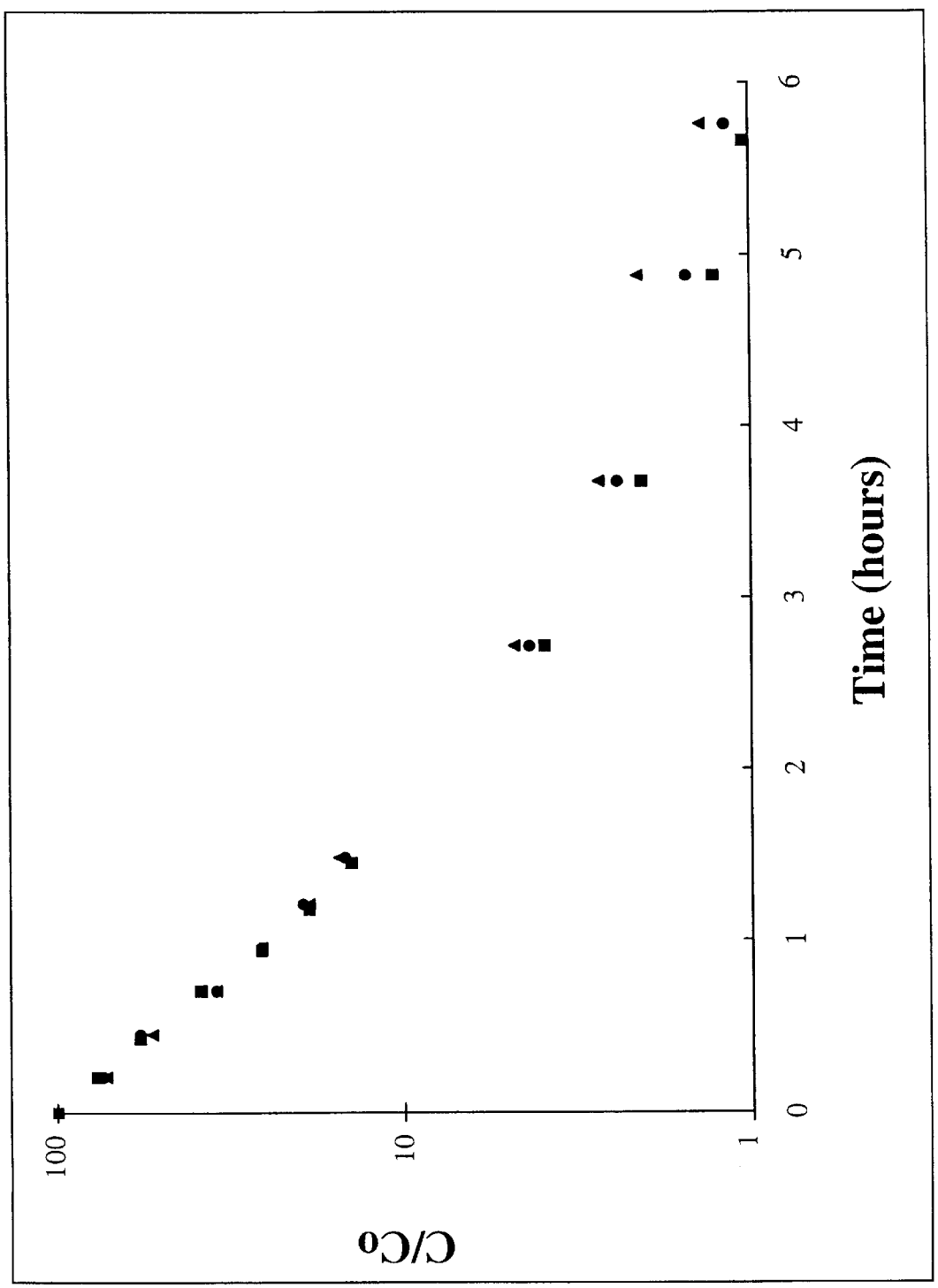

Sorption rates are recorded as the log of the percentage concentration remaining against time. $C_2N_2$ could still be detected 24 hours after application in the 25% filling ration samples (FIG. 18) although its rate of depletion remained linear. $C_2N_2$ concentrations in the 50% (FIG. 19) and 95% (FIG. 20) filling ratio samples also showed linear rates of $C_2N_2$ depletion which increased in accordance with increasing fill. The 95% filling ratio sample had dropped to below the limits of detection within 6 hours of fumigant application.

Figure 21:
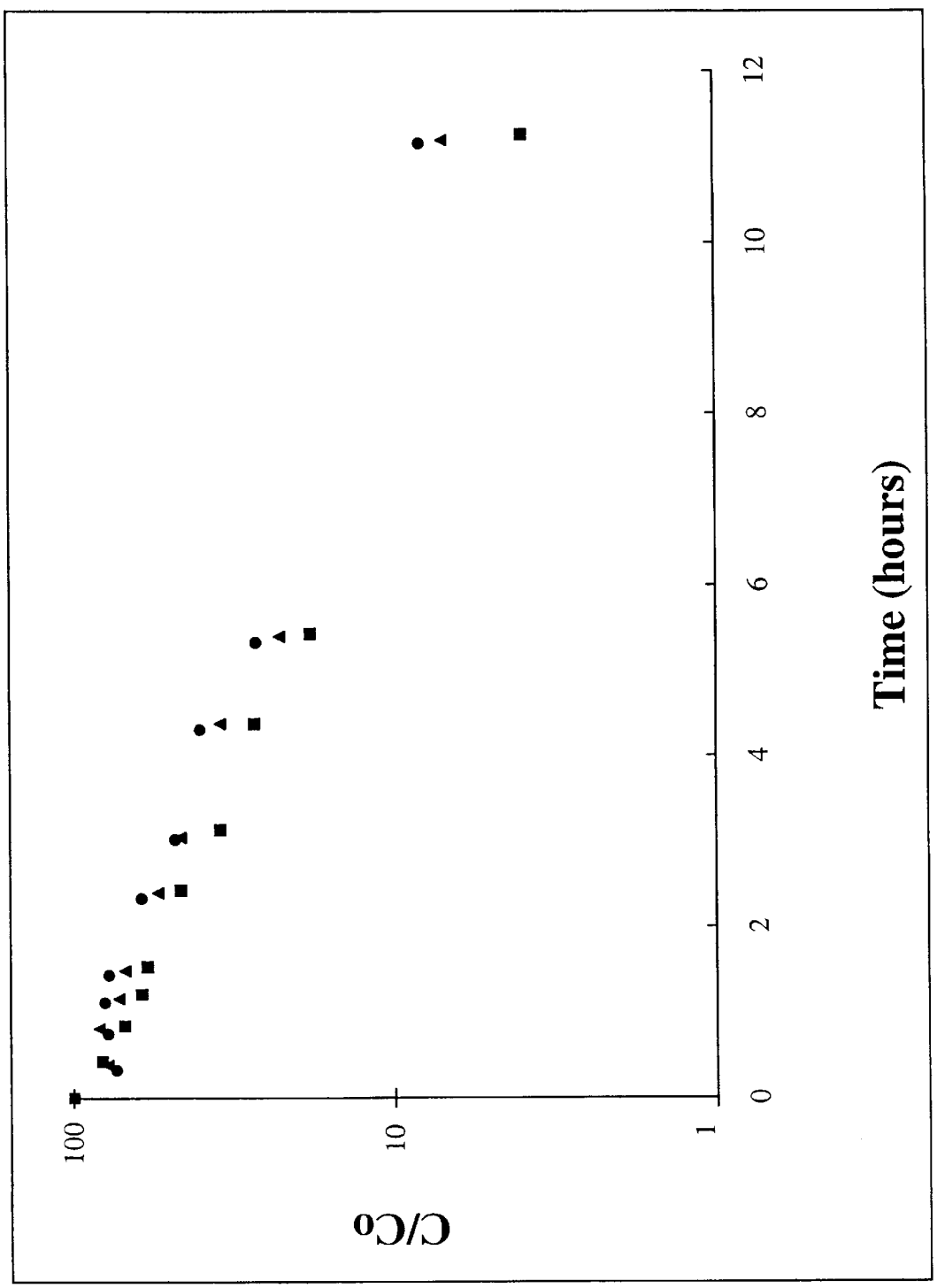
Figure 22:
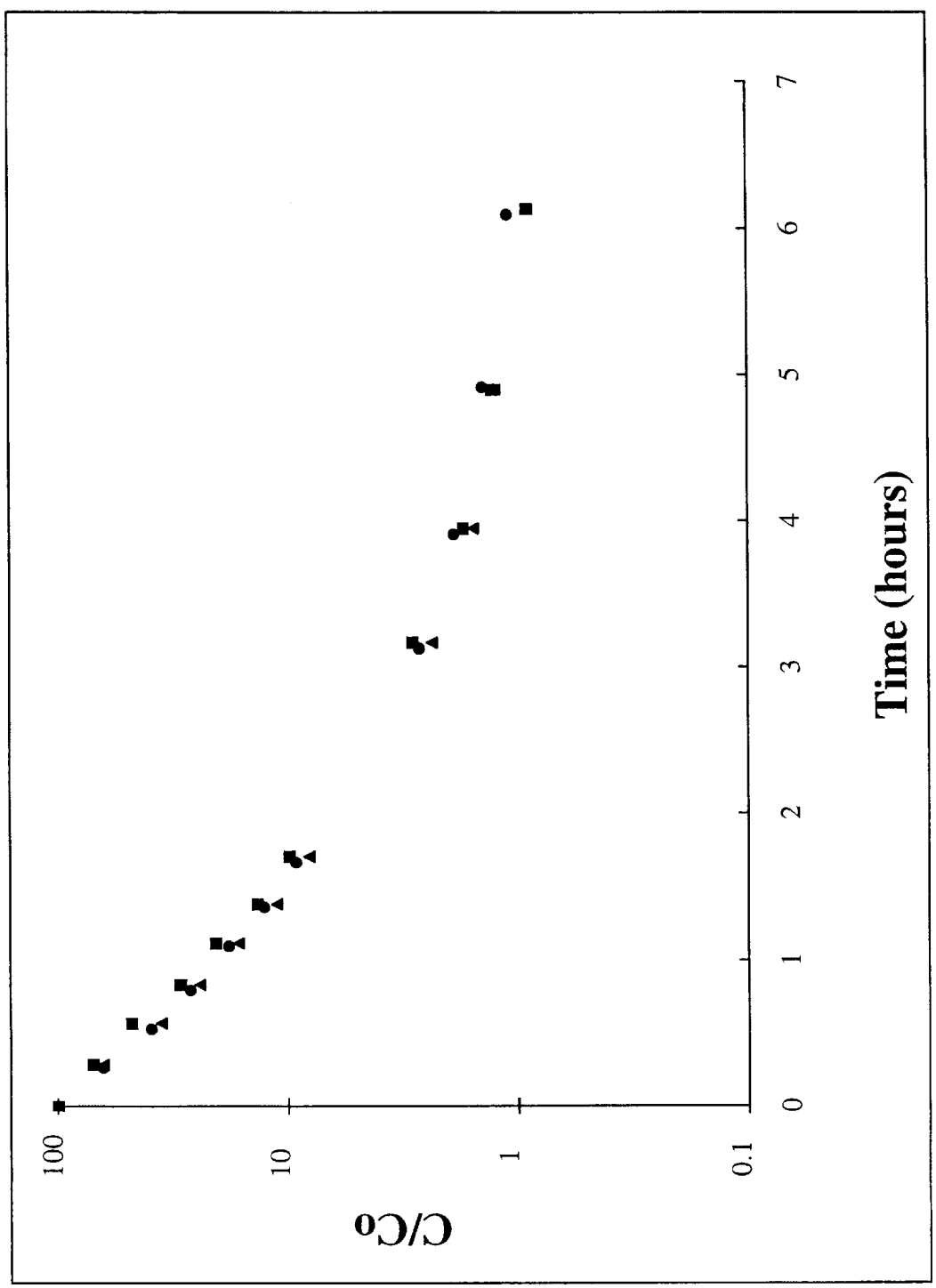
Figure 23:
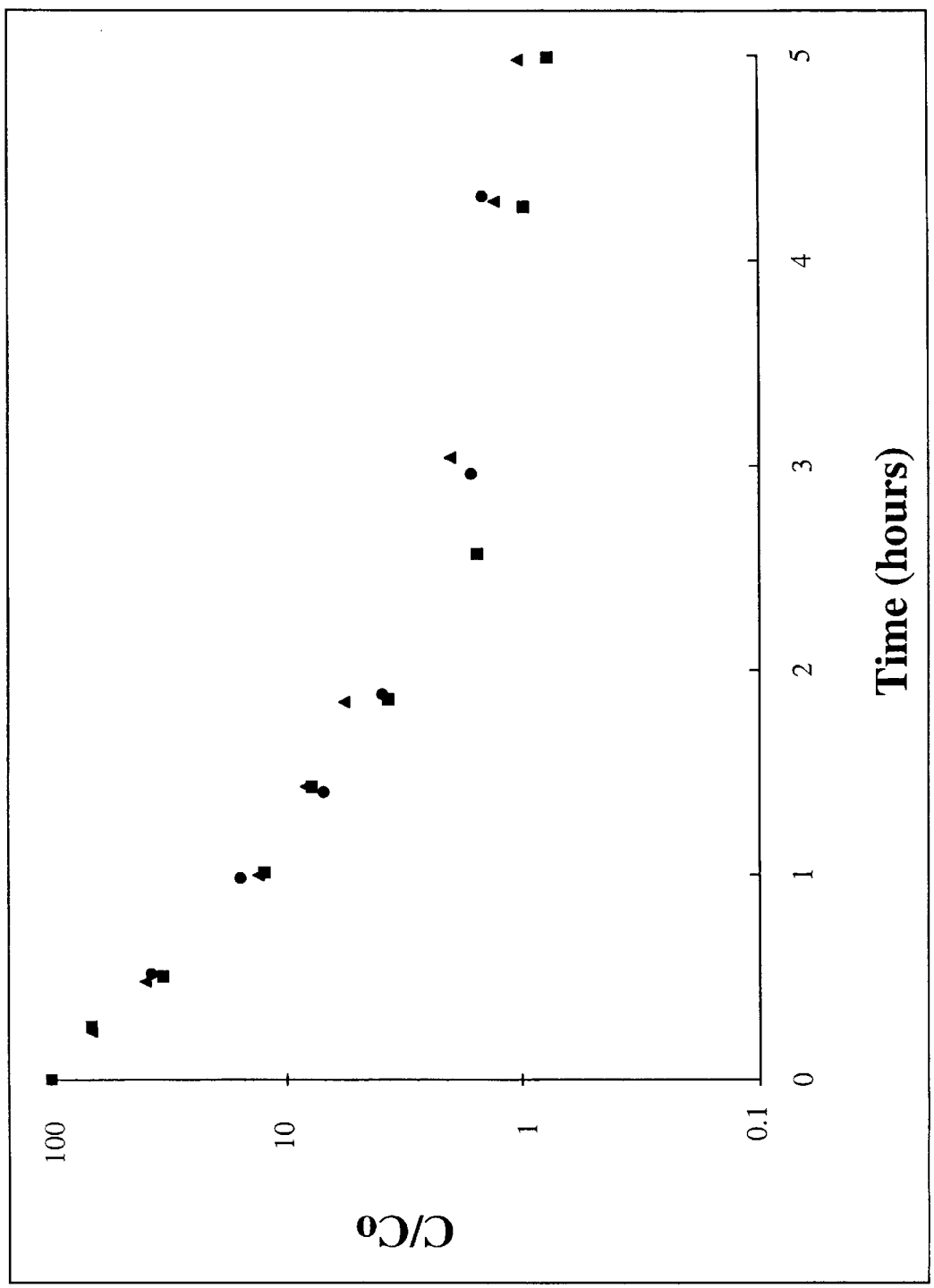
Figure 24:
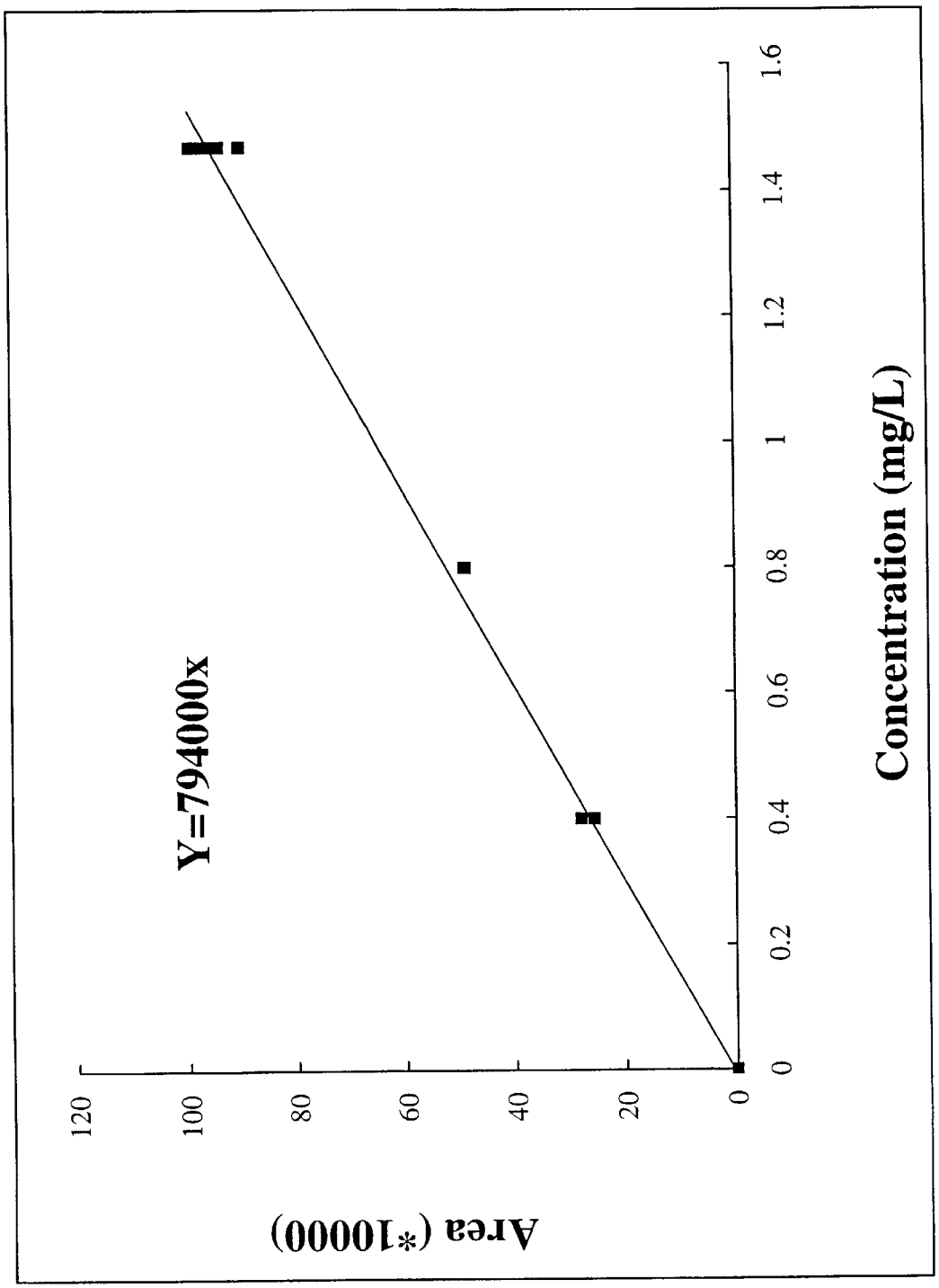
FIG. 24 graphically shows measured concentrations of $C_2N_2$ in water.
Figure 25:
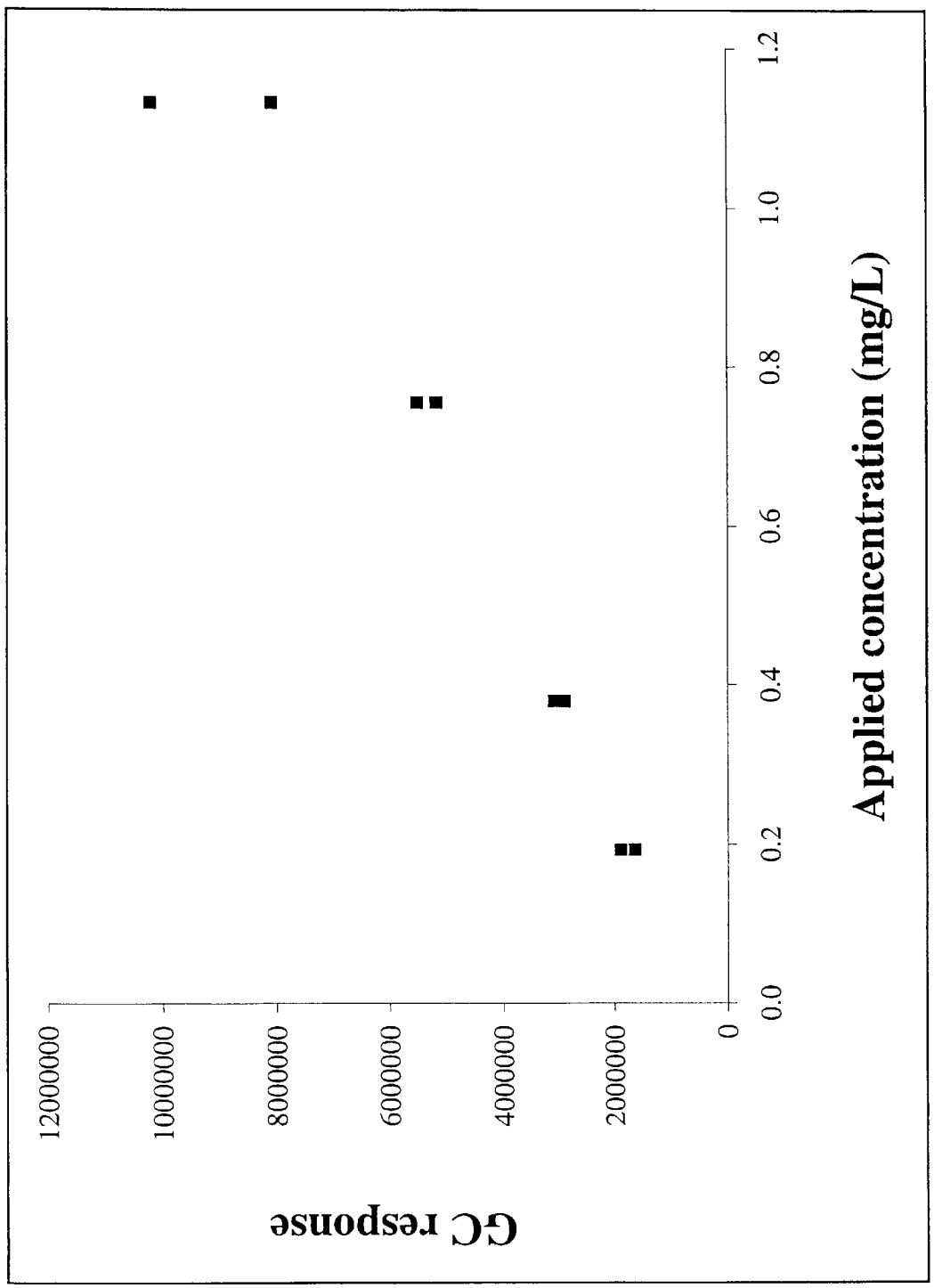
FIGS. 25 and 26 show the residue amounts of $C_2N_2$ in wheat to which fumigant had been added immediately before extraction, when added as a liquid and as a gas.
Figure 26:
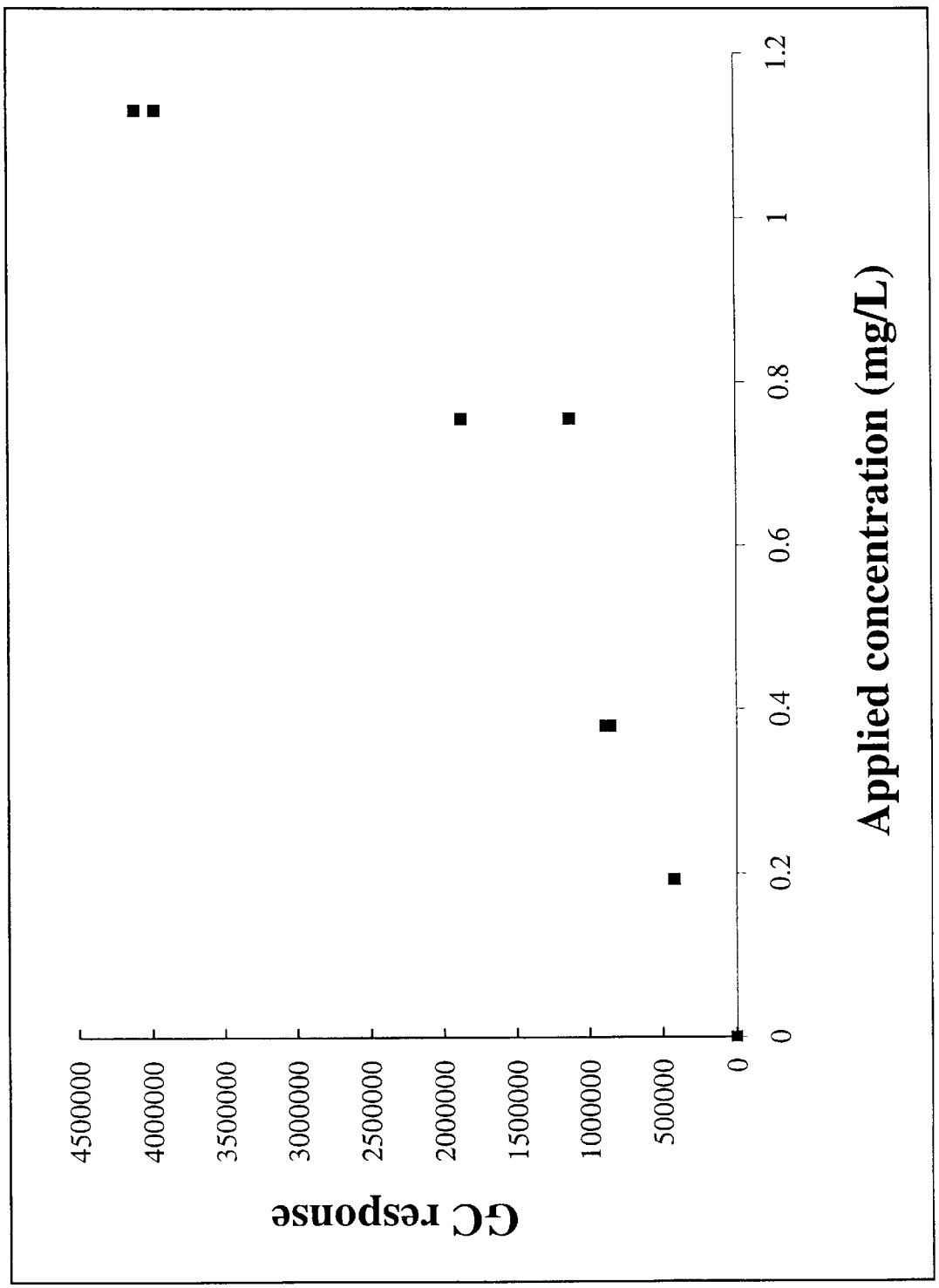

Rates of $C_2N_2$ depletion appeared to strongly correlate to increasing moisture contents of the wheat. The 10% moisture content wheat showed ten fold reduction after over 11 hours fumigation (FIG. 21) whilst a similar reduction was achieved in under 2 hours for the 12% moisture content wheat (FIG. 22) and at approximately 1 hour for the 14% moisture content wheat (FIG. 23). Initial rates of sorption were linear for all moisture content samples although this linearity was lost after about 2 hours for the 12% and 14% moisture content samples.

Discussion

The rapid rate of $C_2N_2$ depletion in high moisture content wheat samples correlates with the high solubility of $C_2N_2$ in water, $C_2N_2$ and HCN residues from wheat that has sorbed $C_2N_2$ have, however, proven to be very low (Examples 3, 26) even after short holding substitute periods, implying that sorbed $C_2N_2$ undergoes rapid chemical degradation which may contribute to the rate of $C_2N_2$ sorption with a corresponding equilibria shift.

Example 25

Method for Measuring and Calculating $C_2N_2$ Concentrations in Water

Introduction and Aim $C_2N_2$ dissolves in water at a ratio of 4:1, V/V (Merck Index). It would be desirable to be able to apply it as a liquid or gas. This study was done to determine an effective way of dosing Queensland fruit fly, *Dacus tyroni* or other target species with $C_2N_2$ dissolved in water and measuring gas and liquid concentrations of the fumigant. It also assessed a method of determining the concentration of fumigant in water.

Material and Methods 1 and 4 mL of 82% $C_2N_2$ was gradually injected into two 16 mL vials fitted with a Mininert screw lid containing 10 mL 0.01 M hydrochloric acid (HCl). This corresponded to 190 $mgL^{-1}$ (sample 1) and 761 $mgL^{-1}$ (sample 2) respectively. After waiting 30 minutes to allow the fumigant to dissolve completely in the solution, 0.1mL of each $C_2N_2$/HCl solution was injected through a rubber septum into separate 275 mL Erlenmeyer flasks fitted with screw cone adaptors. This corresponds to 0.069 $mgL^{-1}$ (sample 3) and 0.276 $mgL^{-1}$ (sample 4) respectively. Three standard gas concentrations of 0.4, 0.8 and 1.48 $mgL^{-1}$ were made in 1.2 L Erlenmyer flasks to determine sample concentrations.

Gas and liquid concentrations were measured on a Varian gas chromatograph fitted with an electron capture detector and DBwax megabore column. Column temperature was set at 60° C., injector temperature at 100° C. and the detector at 288° C. Gas samples of 10 $\mu$L were injected using a 100 $\mu$L Pressure Lok® syringe and liquid samples of 0.1 $\mu$L were injected with a 5 $\mu$L SGE liquid syringe.

Results

For each sample and standard, 10 injections were made and the areas averaged. The standards were used to calculate the actual concentrations in each of the samples, after correcting for injection volume. Table 15.

TABLE 15

Average areas for samples and standards

| sample number | injection vol (uL) | phase | average area | calculated conc ($mgL^{-1}$) | actual conc ($mgL^{-1}$) | loss (%) |
|---|---|---|---|---|---|---|
| standard | 10 | gas | 325535 | 0.4 | — | — |
| standard | 10 | gas | 598735 | 0.8 | — | — |
| standard | 10 | gas | 1179704 | 1.48 | — | — |
| sample 1 | 0.1 | liquid | 1344534 | 190 | 170 | 11 |
| sample 2 | 0.1 | liquid | 5302757 | 761 | 675 | 11 |
| sample 3 | 10 | gas | 45936 | 0.069 | 0.059 | 14 |
| sample 4 | 10 | gas | 172196 | 0.276 | 0.219 | 21 |

Standard areas were plotted against concentration (FIG. 24) to check that the gas chromatograph responded in a linear fashion over the concentration range. Regression analysis showed that response was linear (R=0.99).

Table 15 shows that measured concentrations in both the gas and liquid samples are up to 21% lower than calculated concentrations. Both liquid samples had a loss of 11% which may be due to some $C_2N_2$ remaining in the headspace and not dissolving in the HCl solution. The slightly higher loss rates between calculated and measured concentrations in samples 3 and 4 would be due to the summed errors of the lower than expected liquid concentrations, incomplete volatilisation of $C_2N_2$ from the 0.1 mL HCl/$C_2N_2$ solution and sampling error.

Discussion

There is a 11% lower concentration of $C_2N_2$ than calculated when the fumigant is dissolved in 10 mL of 0.01 M HCl, due to phase equilibrium between the aqueous and gas phases. The proportion of total fumigant in the gas phase will depend on the phase rule and on the volumes of liquid and gas. To minimise the error, samples of the HCl/$C_2N_2$ solution should be anlaysed on the gas chromatograph before dosing *D. tyroni* or other insects. This would enable target concentrations to be more accurately predicted.

The methodology is available to measure $C_2N_2$ in the liquid phase and to calculate doses exactly.

Example 26

Residues of, and Method of Analysis for, $C_2N_2$ in Wheat

Aims: to determine residues of $C_2N_2$ in fumigated wheat, to obtain residue data.

The extent of $C_2N_2$ residues, and the extent of their conversion of HCN, is important for the use of $C_2N_2$ as a grain fumigant. The inventors are somewhat skeptical about most of the methodology used to measure fumigant residues, and therefor residues have been determined by a number of procedures (e.g. Example 3).

Materials and Methods

Australian standard white wheat, 11.6% moisture content, wet weight basis, was weighed into 120 mL flasks equipped with Mininert valves. Three filling ratios were used: 25%, 50% and 95%; for example, the flasks were filled with 25% wheat, 75% air to give a filling ratio of 25%.

For analysis of $C_2N_2$ in wheat, 20 g of wheat was placed in a 120 mL flask, fitted with a Mininert valve, and 20 mL of analytical grade tetrahydrofuran was added. The solution was left to stand overnight. The fumigant was measured in both the liquid phase (by injection of 2 $\mu$L aliquots) and in the headspace over the liquid (by injection of 100 $\mu$L aliquots). The fumigant was detected on a Varian 3300 Gas Chromatograph, equipped with a Thermionic Specific Detector, after separation on a DBwax column, of internal diameter 0.53 mm.

Fumigant was applied to give concentrations of 6.73 $mgL^{-1}$, 13.38 $mgL^{-1}$, and 12.94 $mgL^{-1}$ for the 25%, 50% and 95% filled samples respectively. These compounded to residues of 35.1, 34.2 and 17.3 $mg/kg^{-1}$, respectively. Residues were determined at timed intervals after application. All residue determinations were performed in triplicate, and all determinations for the analytical procedure in duplicate.

Results

Method of Analysis

Machine response is recorded against the amount of $C_2N_2$ added as liquid in FIG. 25, and against the amount added as gas in FIG. 26. The machine response was linear with applied concentration and reproducible. The limit of detection, defined as twice the signal to noise ratio, was determined from headspace injections and from liquid injections. It corresponded, from the headspace method, to residues in the grain of $4.3\times10^{-3}$ mg/kg (4.3 ppb, W/W) in the wheat and, from the headspace method, to 0.037 mg/kg (37 ppb, W/W) from injection of the liquid. The main reason for these differences in limits of detection was interference from the solvent, that is, to responses in the solvent that corresponded to $C_2N_2$.

Extraction of unfumigated wheat in tetrahydrofuran did not alter the limits of detection from those in solvent, indicating that the levels of $C_2N_2$ in unfumigated wheat were, at most, extremely low. The limit of detection by the headspace method, however, was increased to a level corresponding to 0.036 mg/kg.

Residues

Residue data are outlined in Table 16. The decline in residues, in a fully sealed system was substantial. It averaged 98% after 3 days, and well in excess of 99%, after 14 days.

For wheat dosed at 35.1 mg/kg, at a 25% filling ratio and held at 22° C. for 14 days, residues from the headspace method averaged 0.081 mg/kg, s.d. 0.009 mg/kg. From the liquid injection method, residues in wheat averaged 0.21 mg/kg, s.d. 0.083 mg/kg. For wheat in a container 95% full, and dosed at 17.3 mg/kg, residues on wheat by the headspace method, after a holding period of 3 days, were 0.52 mg/kg, s.d. 0.24 mg/kg. Residues were not determined by liquid injection in this case.

For wheat dosed at 34.2 mg/kg, and held for 14 days at 22° C., the headspace reading in one of the three replicates was below that in the control sample, and was below the limit of detection, defined as twice the signal to noise ratio. The difference between the sample reading and that in the control corresponded to a residue level in wheat of 0.003 mg/kg. For the liquid injection, the level was again below the limit of detection, defined as twice the signal to noise ratio. The difference between the samples and the control corresponded to a level of 0.013 mg/kg, s.d. 0.005 mg/kg. Thus the residue level is best described as a possible trace, but below the limit of quantitative detection.

Discussion

Residues of $C_2N_2$ can be detected in grains down to low levels, and can be determined from the headspace or from liquid injections. The decline of residues is very rapid. This rapid decline of residues in replicated in other experiments reported in Examples 3 and 43. Some hydrogen cyanide was observed in each method of detection, and this is covered in a separate document (Example 43).

TABLE 16

Residues of $C_2N_2$ in wheat

| Filling ratio (%) | Amount applied (mg/kg) | Interval after dosing (days) | Residue (mg/kg) Headspace mean | s.d | Residue (mg/kg) liquid mean | s.d |
|---|---|---|---|---|---|---|
| 25 | 35.1 | 14 | 0.056 | 0.021 | 0.21 | 0.08 |
| 50 | 34.2 | 14 | trace? | — | trace? | — |
| 95 | 17.3 | 3 | — | — | 0.52 | 0.24 |

Example 27

Toxicity of C2N2 to Larvae of *Ephestia cautella*

Aim: To evaluate the toxicity of $C_2N_2$ to larvae from a Lepidopteran species, *Ephestia cautella* (Walker).

Materials and Methods

Duplicate samples of 15 late instar *E. cautella* larve and a thin strip of corrugated cardboard were transferred to 120 mL glass bottles fitted with Mininert valved lids. These were sealed and appropriate volumes of air removed prior to the addition of $C_2N_2$. Fumigated samples were maintained at 30° C. except for their brief removal for gas chromatograph analysis.

$C_2N_2$ concentrations were checked by injecting 20 l aliquots from the samples into a Varian 330 Gas Chromatograph equipped with a Thermionic Specific Detector after separation on a DBwax column of 0.53 mm internal diameter. Gas chromatograph recordings were taken within 2 hours of applying $C_2N_2$ for both the 6 hour and the 24 hour exposures. A second set of gas chromatograph recordings was taken for the 24 hour exposures approximately 2 hours before the termination of the fumigation.

Results

The results for these fumigations are summarised in table 1.

TABLE 1

Toxicity of $C_2N_2$ to Larvae of *E. cautella*

| Exposure Time (hours) | Concentration (mgL$^{-1}$) | Mortality (%) |
|---|---|---|
| 24 | 0 | 3.33 |
| 24 | 0.69 | 23.33 |
| 24 | 1.37 | 93.33 |
| 24 | 2.75 | 100 |
| 6 | 0 | 0.00 |
| 6 | 1.29 | 83.33 |
| 6 | 2.59 | 100 |
| 6 | 3.88 | 100 |

Discussion $C_2N_2$ induced 100% mortality within a 6 hour exposure at 2.59 mgL$^{-1}$ for larvae from the Lepidopteran species *E. cautella*. In this study, increasing the exposure period of larvae to the fumigant did not result in a substantial increase in the mortalities for the lower doses.

Example 28

Storage of NF2 in Tedlar Bags

Aim: to determine whether $NF_2$ could be stored in Tedlar bags, and other plastic containers, to provide a convenient method of storing the fumigant, especially for small-scale uses.

Materials and Methods

Commercial Tedlar bags were used, purchased from SKC Inc. 334 Valley View Rd., 84 Pennsylvania. U.S.A. These are plastic bags with an injection system for introducing, and withdrawing, gas. The gags, as purchased, are essentially free of air. The fumigant NF2 was injected into bags, using an air-tight syringe. Concentration of NF2 was measured, over timed intervals, on a Tractor MT150 Gas Chromatography, equipped with a Gow-Mac gas density balance. In addition, hydrogen cyanide was measured on a Varian 3300 Gas Chromatograph, equipped with a Thermionic Specific Detector, after separation on a DBwax column, of internal diameter 0.53 mm. Hydrogen cyanide standards were prepared by reacting cyanide salts with acid, determining the concentration on the gas density balance, and diluting into sealed flasks.

Dilute concentrations of NF2 in air were also prepared in Tedlar bags and the concentration measured at timed intervals on a Varian 3300 Gas Chromatograph.

The bags were left in an air conditioned laboratory, at a typical temperature of 22° C., with no special precautions to protect against light.

Results

Over a 4 week period during which gas concentrations were measured weekly, the concentration of NF2 in the Tedlar bag was always between 82% and 83%, V/V, with no apparent trend. The concentration of hydrogen cyanide was always between 0.35% and 0.45%. V/V, with no apparent trend. Thus the fumigant is stable in Tedlar bags.

Lower concentrations were also stable in the system. For example, a concentration of 0.66 mgL$^{-1}$ was stable, within experimental error, over the duration of an experiment of 3 days.

Discussion

The stability of NF2 in glass and in water, of appropriate pH, and in solvents has been shown in other sections (eg phase.doc, document 33; water doc, document 23. The stability in cylinders is covered by a Department of Transport number (safety.doc. document 24). The stability in Tedlar bags offers another alternative method of storage and dosing, which is very convenient for some uses. The vapour density of NF2 is 2.3 gL$^{-1}$, such that 23 g of material can be stored in a 10 L bag, and proportional amounts in larger or smaller containers. The method of storage is convenient for situations where amounts measured in milligrams or grams, rather than kilograms, are required, as would often be the case in surgeries, hospital departments, etc. The only equipment required would be a gas-tight syringe, of appropriate capacity, and the bag containing the fumigant. As with all methods of storing toxic gases, appropriate safety procedures would be required for storage, and such procedures could include the amount stored, through variation of the size of the container and the initial concentration of fumigant. Other variations of containers are possible.

Example 29

Movement of $C_2N_2$ and Other Gases Through a Column of Wheat

Aim: To determine whether $C_2N_2$ could be blown through a column of wheat.

Materials and Methods

The procedure used was exactly as described in Desmarchelier, 1994. Fumigant was blown through a 1.1 m column of wheat, of total volume 7.9 L, at an airflow rate of 200 mL.min$^{-1}$. Fumigant was introduced to the column via a 200 mL flask at the bottom of the column. It was measured at the top of the column. Fumigants tested were phosphine, methyl bromide, $C_2N_2$ and hydrogen cyanide. In one experiment, these four fumigants were applied simultaneously. In another experiment, $C_2N_2$ was applied without other fumigants, as was hydrogen cyanide in a further experiment.

Fumigants were detected on a Varian 3300 gas chromatograph. Phosphine and $C_2N_2$ were determined on a Thermionic Specific Detector, after separation on a BP624 column, of internal diameter 0.53 mm. Methyl bromide was detected on an electron capture detector, after separation on a GSQ column, of internal diameter 0.53 mm.

Results

Figure 27:
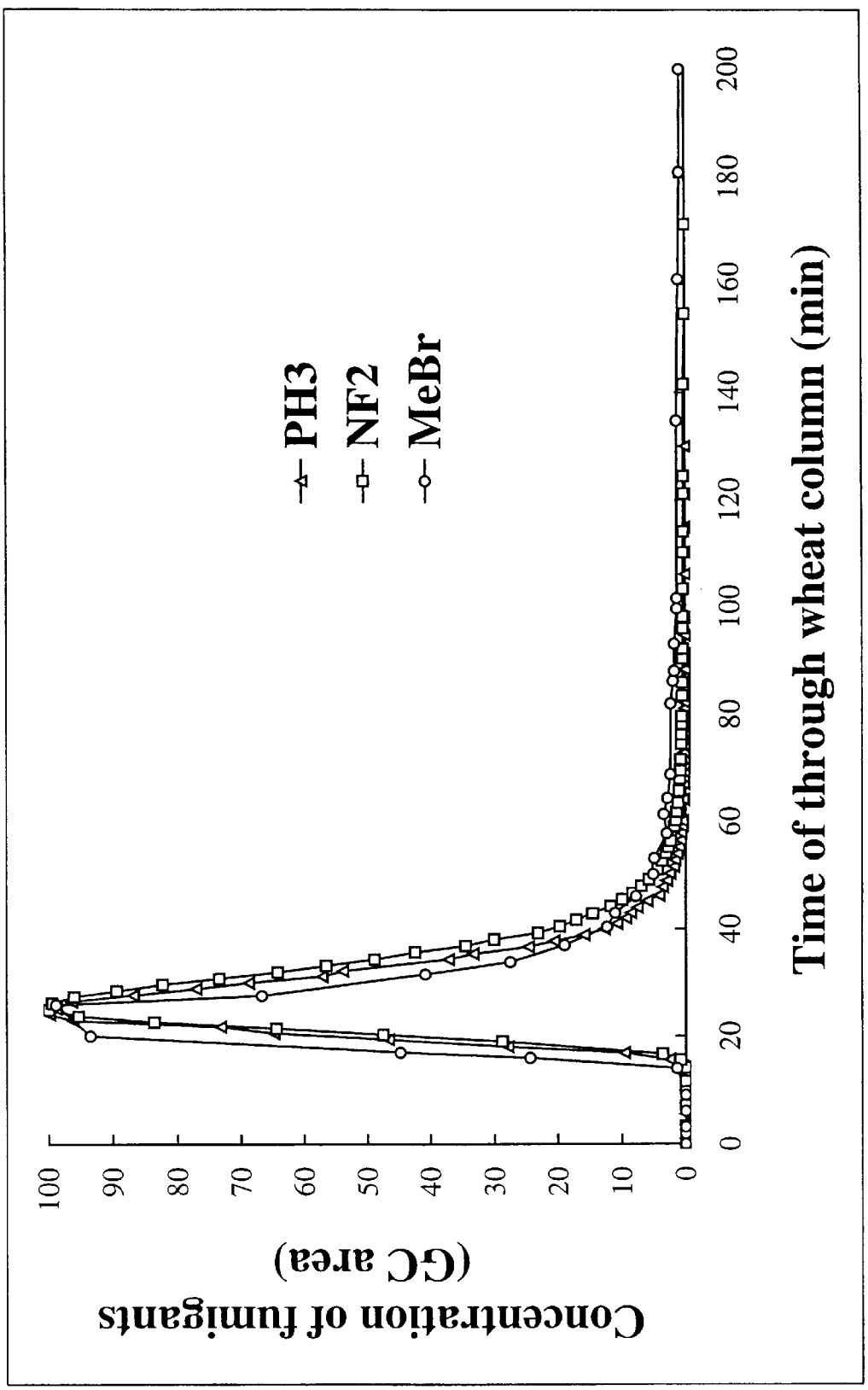
FIG. 27 shows the movement of $C_2N_2$ and other gases through a column of wheat.

Fumigant concentration in the effluent gas is shown in FIG. 27. The fumigant $C_2N_2$ is moved through wheat in a similar manner to the two most widely used fumigants, phosphine and methyl bromide. The results for these fumigants, applied simultaneously, are similar to results for these fumigants, applied individually (Desmarchelier, 1994). Under the conditions studied, hydrogen cyanide could not be moved through wheat, and no hydrogen cyanide was detected in the effluent.

Discussion

Because $C_2N_2$ can move through wheat in an air stream, it can be used in flow-through types of application and in recirculation systems. Its toxicity to insects in each type of situation has been shown in Examples 2, 8 and 10.

Example 30

Toxicity of $C_2N_2$ to Two Species of Coleoptera

Aim: to determine the toxicity of $C_2N_2$ to two species of Coleopteran pests of stored products, and to assess the dose-response curve by probit analysis.

Materials and Methods

Insects tested were adults of *Tribolium confusum* (du Val) and *Rhyzopertha dominica* (F). Insects (50) were placed in 120 mL glass jars, at 55% relative humidity and held at 25° C. The jars were fitted with Mininert valves through which the fumigant was injected. Insects were exposed for 6 h, and then transferred to jars containing flour of 12% moisture content, W/W. Insects were counted after holding periods of 7 and 28 dyas. Mortality was assessed by probit analysis, using data from 6 replicates at each dose. Mortality was corrected for control mortality by Abbot's formula.

Applied concentrations of $C_2N_2$ were calculated from the amount applied, and verified by analysis on a Varian 3300 Gas Chromatograph, equipped with a thermionic specific detector, after separation on a DBwax column, of internal diameter of 0.53 mm.

Results

After initial exposure, there was some apparent recovery from the initial "knockdown". However, over the period 1–4 weeks, mortality increased. In this respect, $C_2N_2$ is similar to phosphine, in that some insects die slowly and short holding periods after fumigation may result in underestimation of the end-point mortality.

Figure 28:
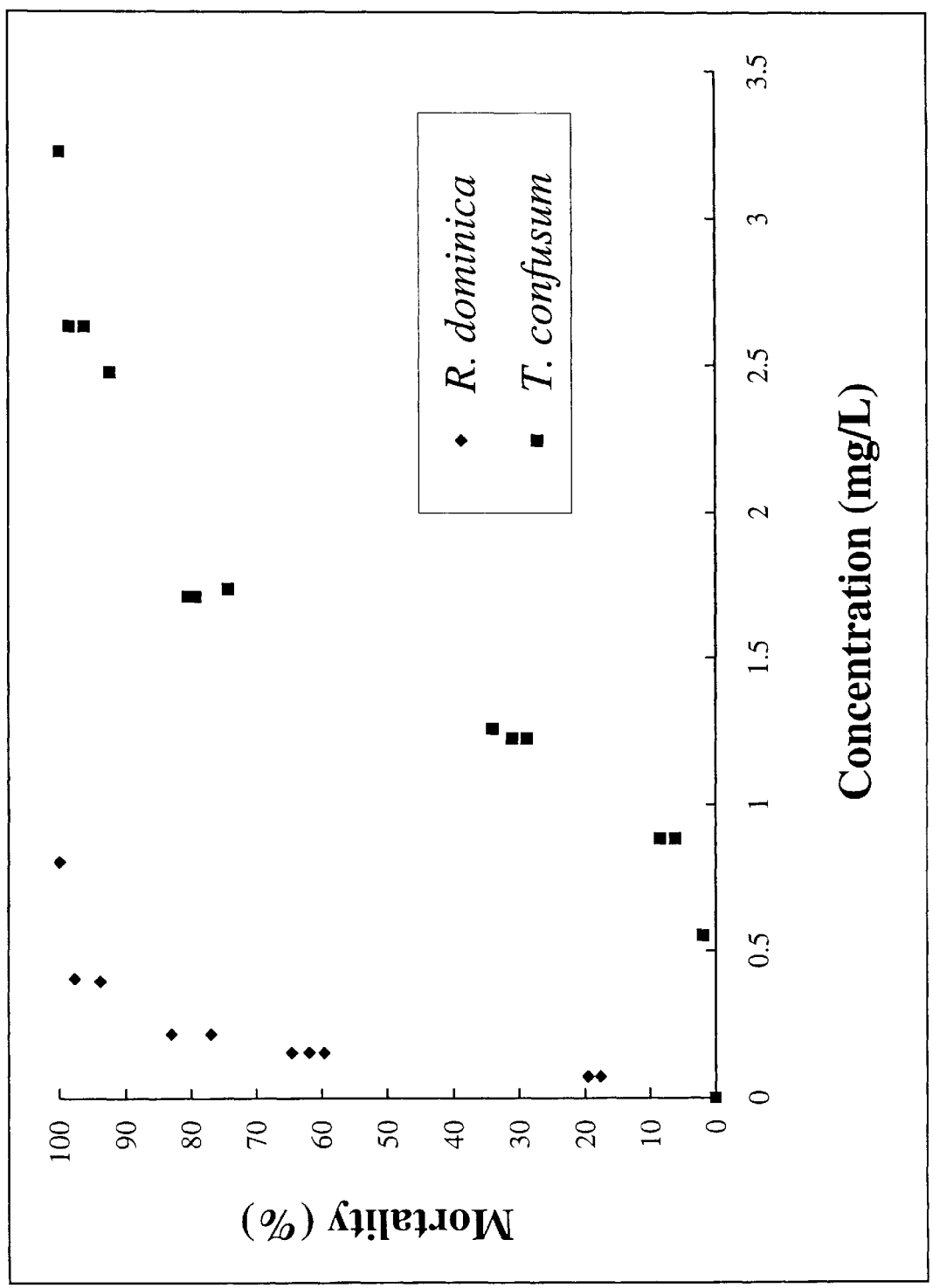
FIGS. 28 to 30 show toxicity results of $C_2N_2$ to two species of Coleoptera.

Mortality is plotted against the concentration in FIG. 28. The curves for each insect are typical "S-shaped" curves.

Figure 29:
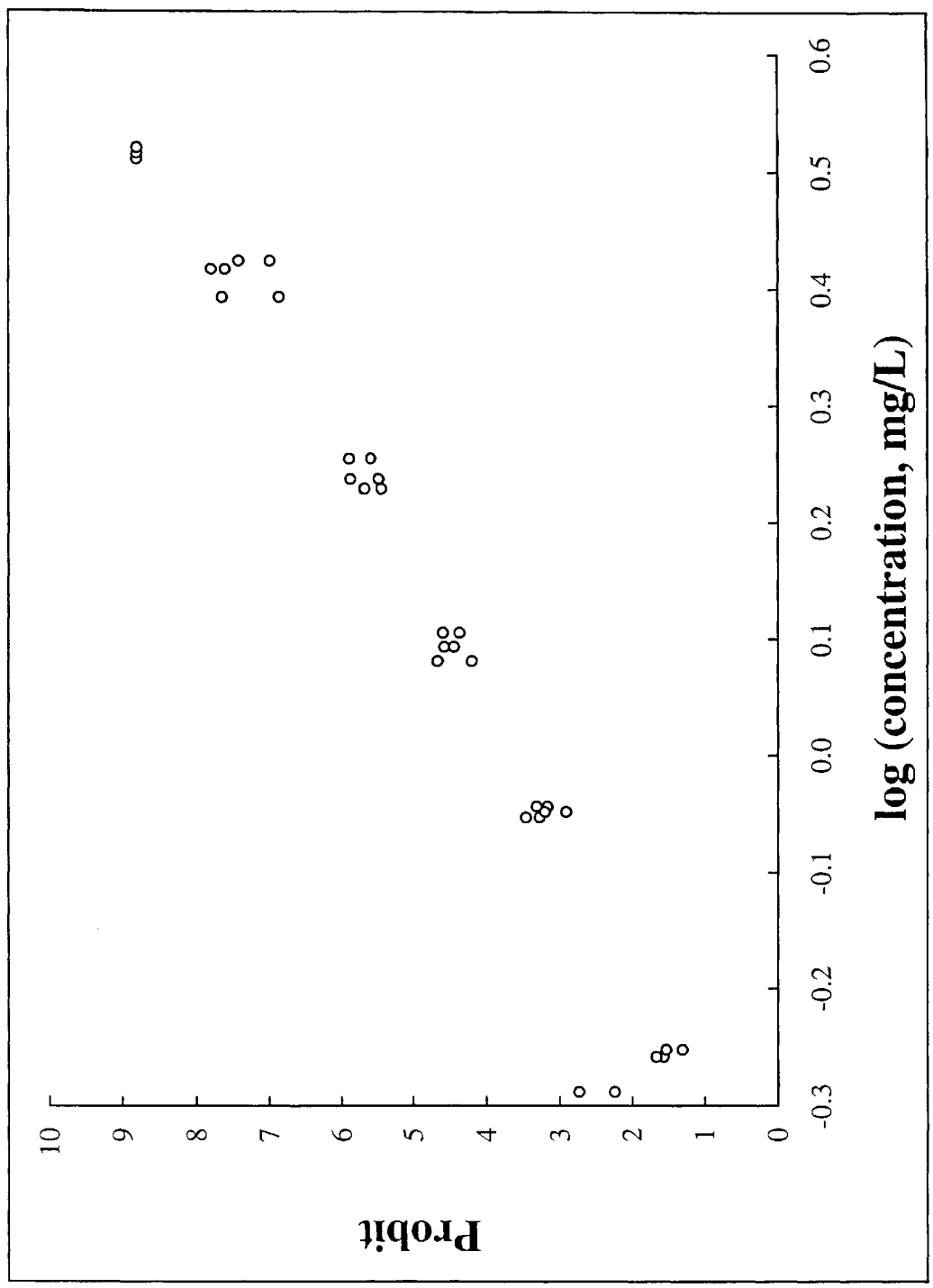
Figure 30:
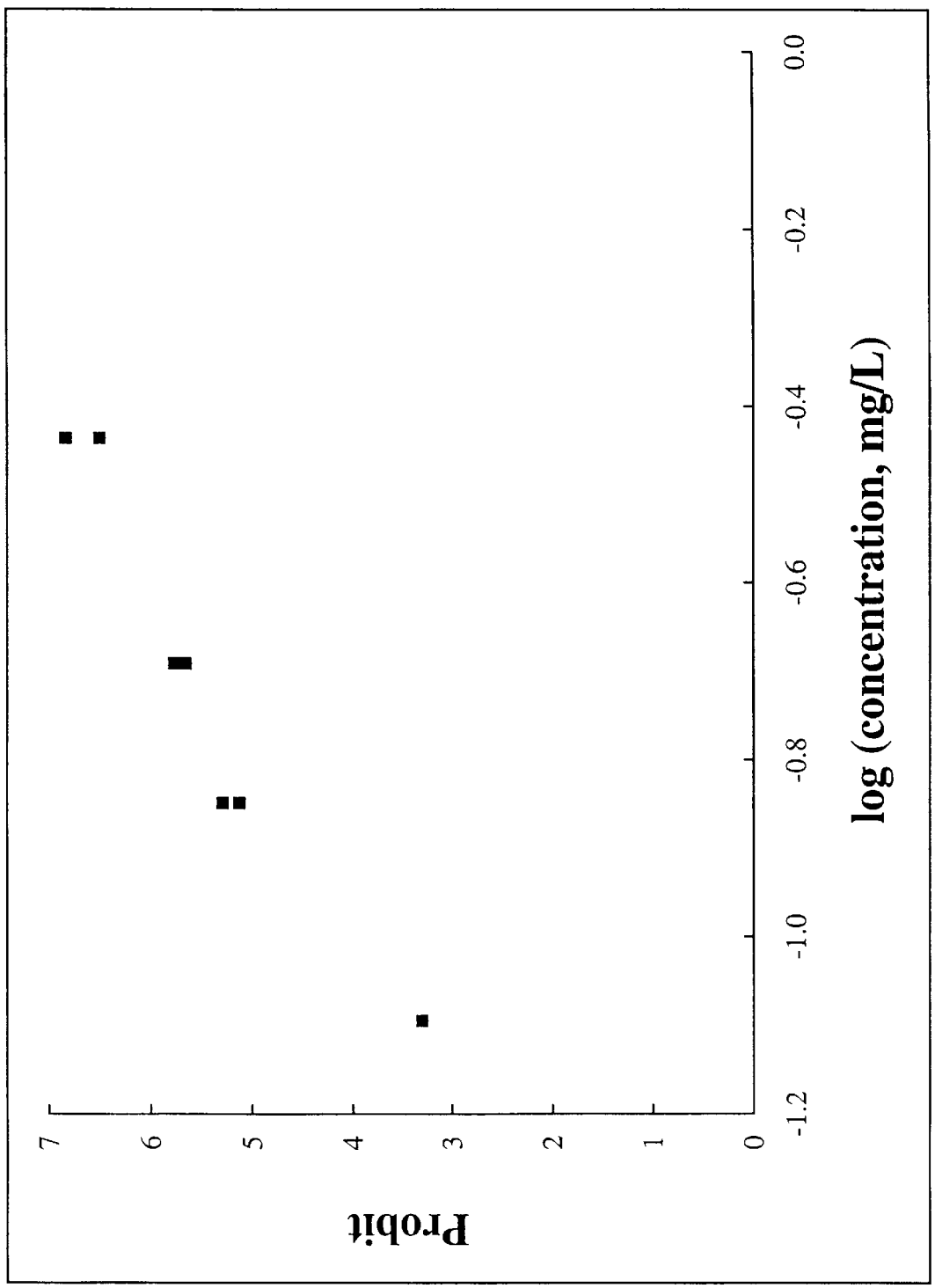

The plot of probit mortality versus log concentration for *T. confusum* is shown in FIG. 29. The response is linear, indicating that the response follows the expected pattern of a linear correlation between probait mortality and log concentration. A similar plot for *R. dominica* is shown in FIG. 30.

For 6 h exposure, the $LC_{50}$ values for *T. confusum* and *R. dominica* were, respectively, 1.41 and 0.141 mgL$^{-1}$.

Monro (1969) lists the $L(C \times T)_{95}$ values of 9 fumigants, for 5 h or 6 h exposures, against *R. dominica* at 21° C. and the $L(C \times T)_{99}$ values of 10 fumigants against *T. confusum* at 25° C. The fumigant $C_2N_2$ was more toxic than any of the fumigants, in the case of *R. dominica,* and more toxic than any fumigant except hydrogen cyanide, in the case of *T. confusum.* The list of fumigants included ethylene dibromide, chloropicrin and methyl bromide. The toxicity of phosphine was also recorded, but only for 24 h exposures at 27° C.

Discussion $C_2N_2$ is highly toxic to the insects tested, and more toxic than methyl bromide or ethylene dibromide and approximately equi-toxic with hydrogen cyanide. The linearity of response of probit mortality with log concentration assists in the calculation of the required concentration to achieve required levels of mortality.

Example 31

Phase Distribution of $C_2N_2$ Between Solvents and Air, in Sealed Containers, and Stability in Solvents Aim: to determine the stability of $C_2N_2$ in various solvents, and the distribution between liquid and vapour phases. This is useful information for purposes of dosing, and for purposes of analysis.

Materials and Methods

Solvents (25 mL) were placed in Erlenmeyer flasks, of capacity 270 mL, equipped with a septum seal. The fumigant (2 mL. of 80–82% purity, V/V) was injected into the flask, which was stirred with a magnetic stirrer. At timed intervals, aliquots (50 µL) were taken from the vapour phase, and aliquots of 1 µL were taken from the liquid phase. These were injected into a Varian 3300 Gas Chromatograph, equipped with a thermionic specific detector, and $C_2N_2$ was separated from the solvents on a DBwax column, of internal diameter 0.53 mm.

All solvents tested were analytical grade, and water was distilled.

The concentrations in each phase were determined with reference to standards freshly prepared daily. Concentrations recorded in the figures are the mean of triplicate determinations.

Results

Figure 31:
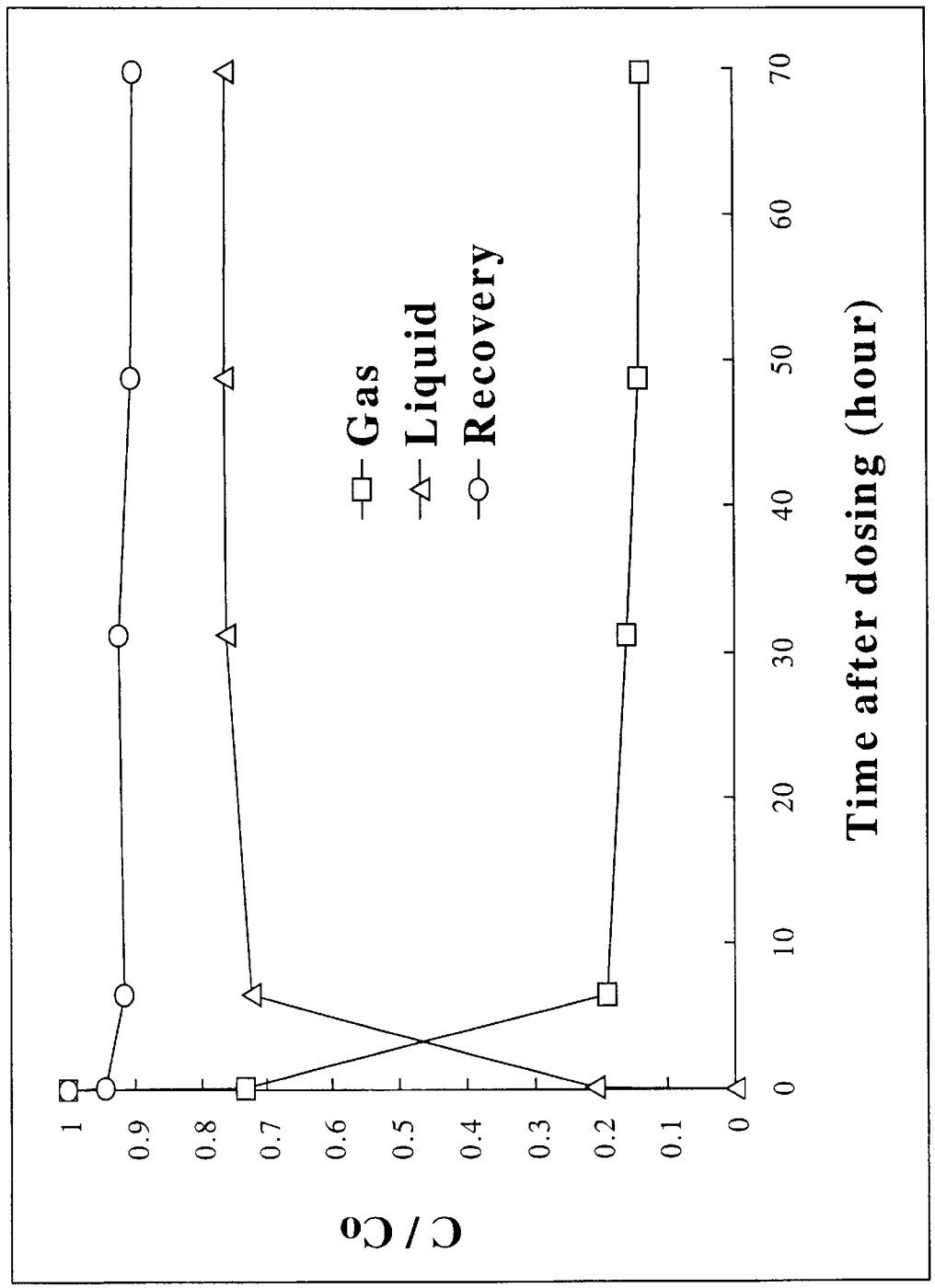
FIGS. 31 to 36 illustrate the stability and phase equilibrium of $C_2N_2$ in various solvents.

The distribution of $C_2N_2$ in 0.1 M hydrochloric acid is shown in FIG. 31. A stable distribution was achieved between phases by 8 h after dosing, and this distribution, plus total amount of $C_2N_2$, remained stable for the duration of the experiment (70 h). In other experiments, $C_2N_2$ was also shown to be stable in 0.01 M hydrochloric acid.

Figure 32:
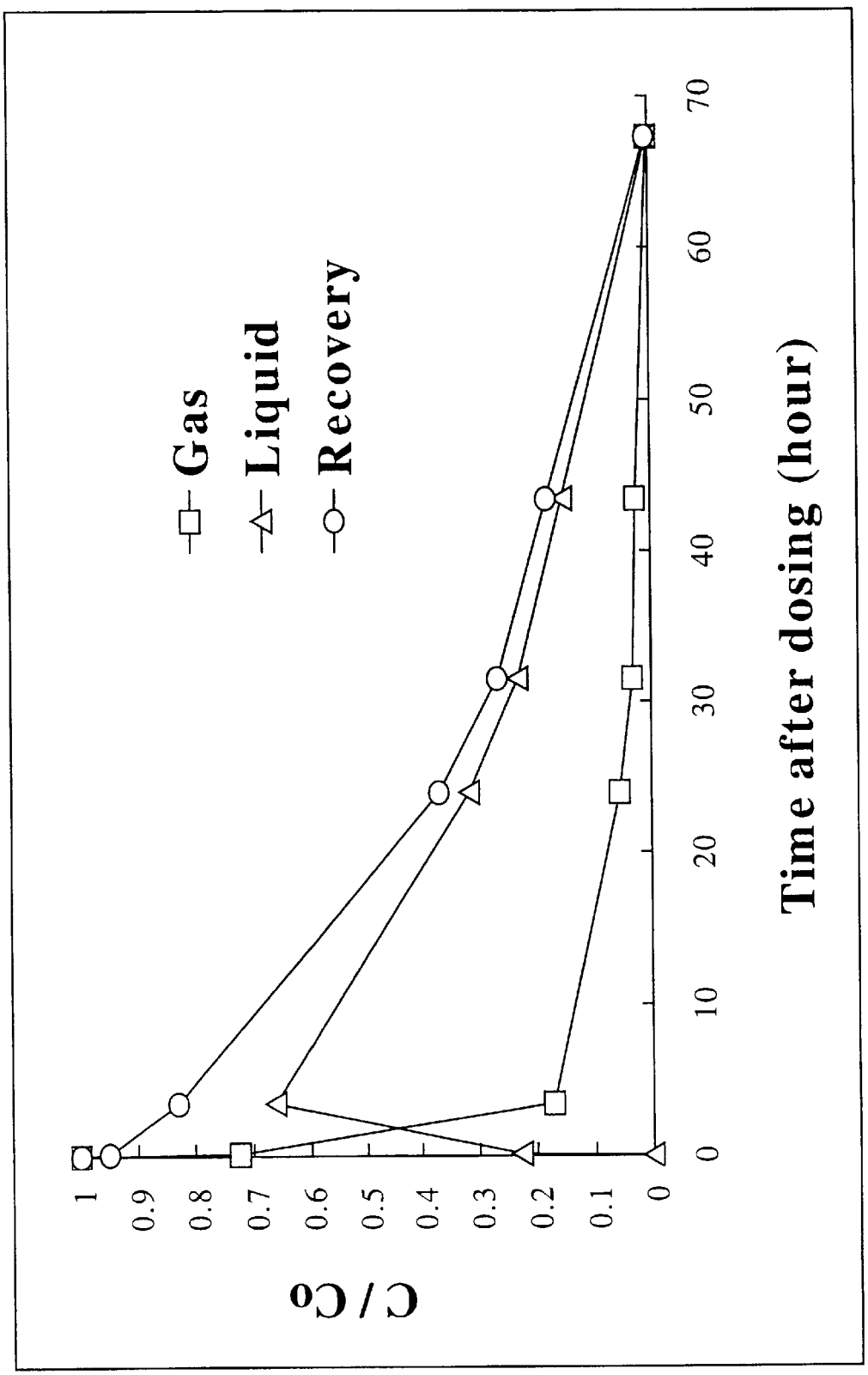
Figure 33:
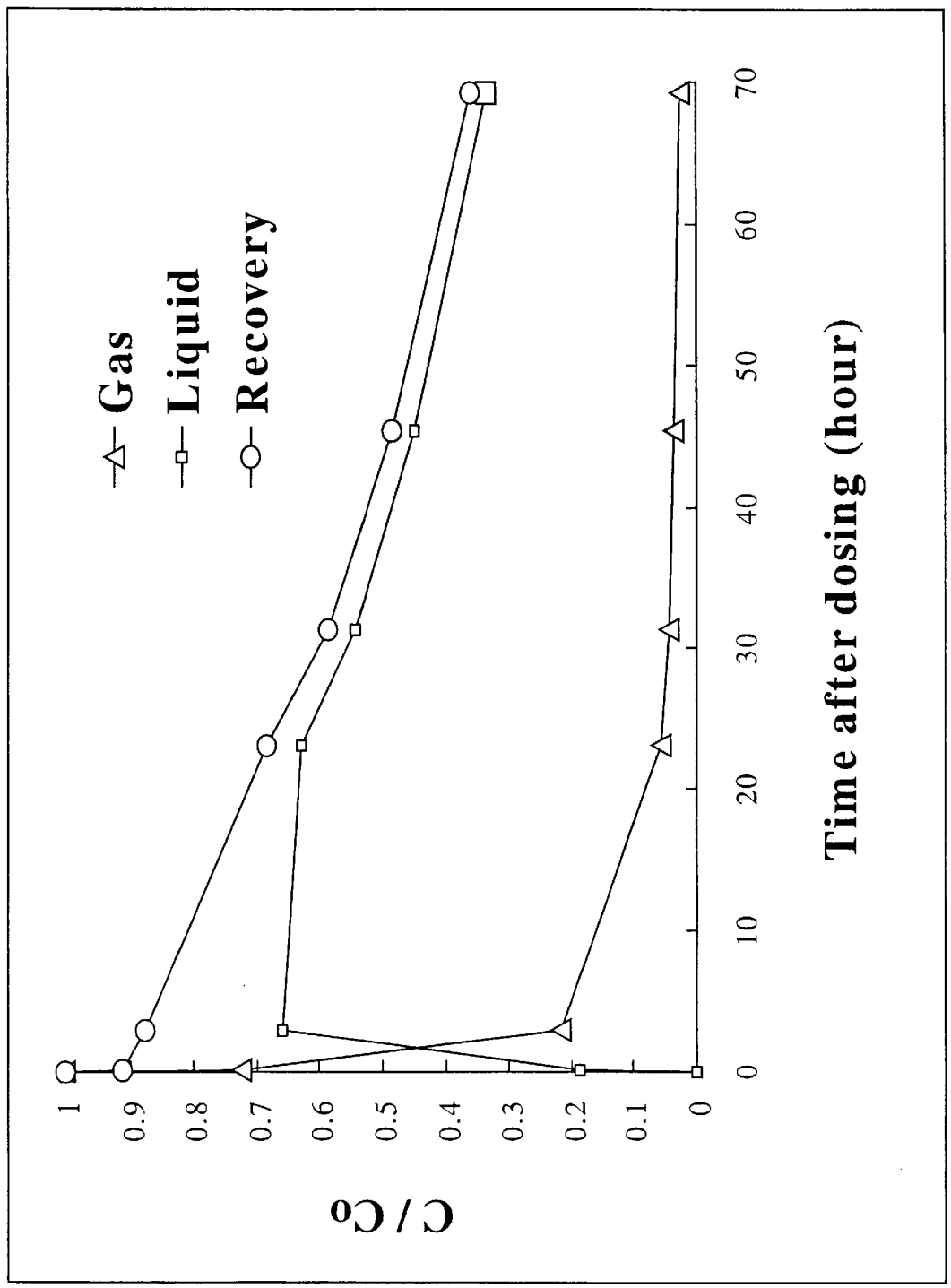

In water (FIG. 32) $C_2N_2$ was relatively stable (FIG. 32) but, in other experiments, it was shown to be very unstable at high pH values (e.g. 8.0, 10.5). However, $C_2N_2$ was unstable in 50% acetic acid, 50% water (FIG. 33).

Figure 34:
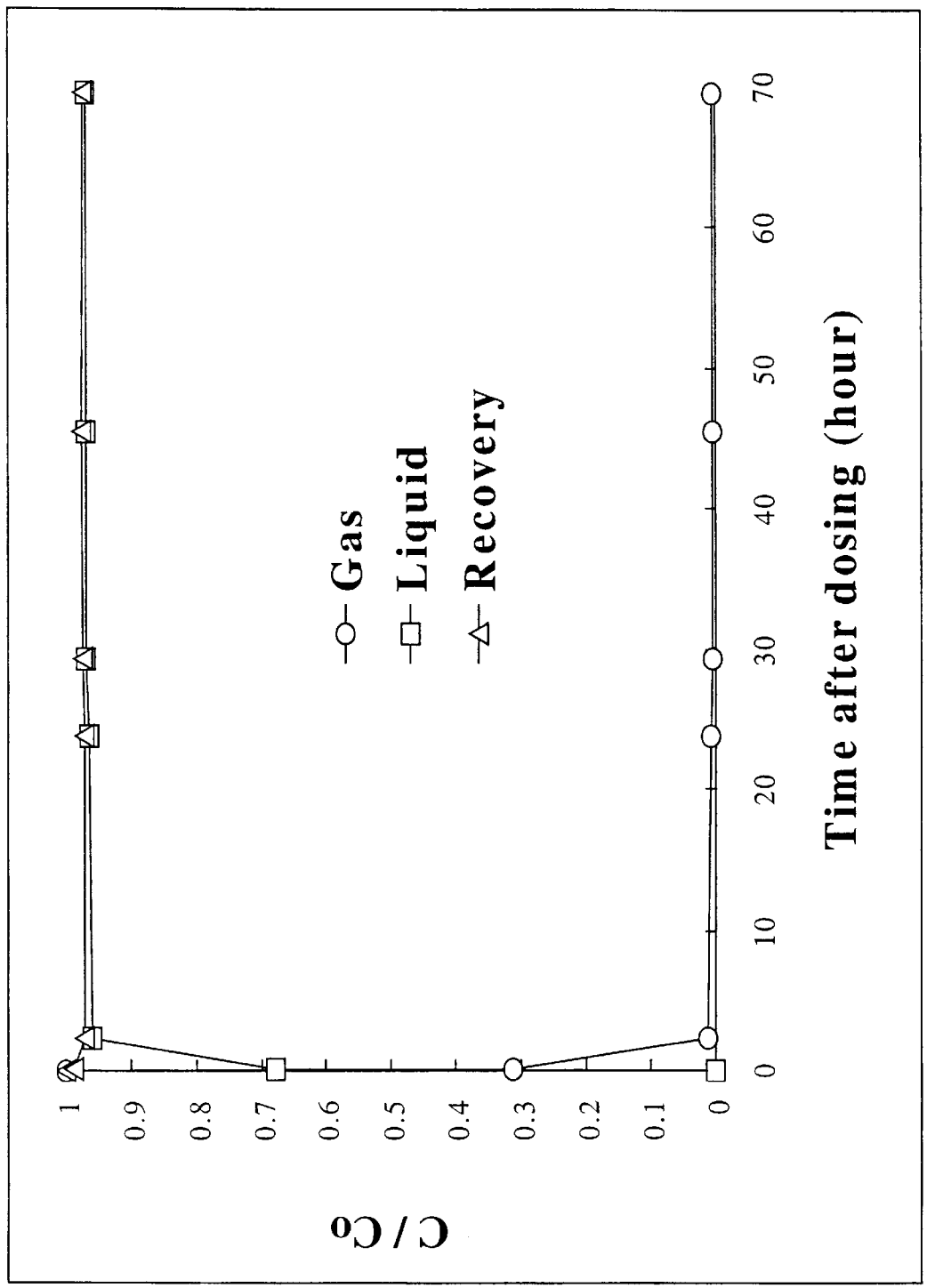
Figure 35:
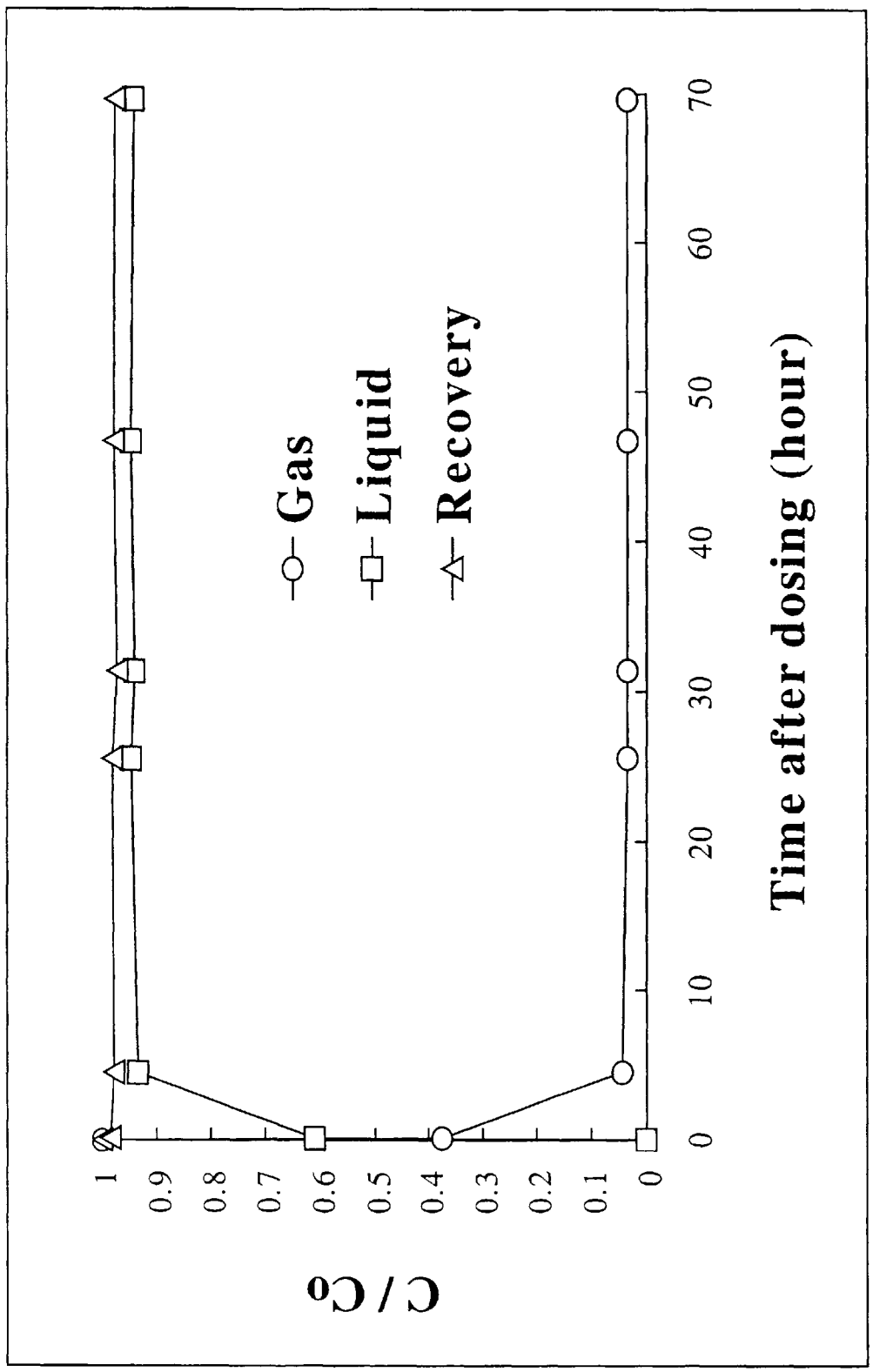
Figure 36:
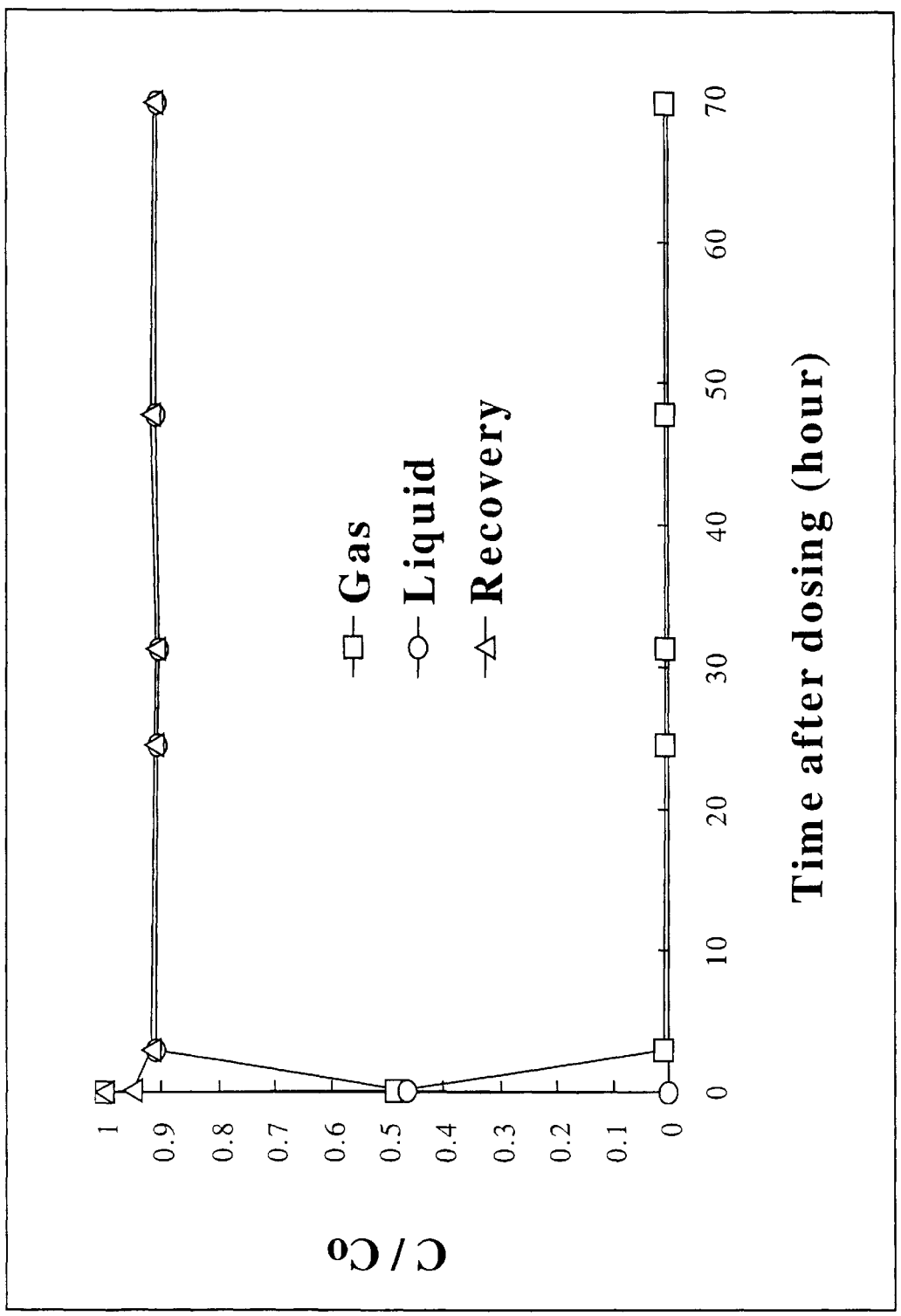

In dioxan (FIG. 34), the distribution between phases and the overall stability was unchanged over a period of approximately 3 days, the period of the experiment. Similar results were obtained for tetrahydrofuran. The phase distribution and overall stability was also excellent in toluene (FIG. 35) and acetone (FIG. 36). The last result is especially pleasing from the point of view of analytical chemistry, because of the wide use of acetone as a solvent in multi-residue analysis.

Discussion

Stability in aqueous and non-aqueous solutions is useful in many areas, e.g. in providing the fumigant in liquids which can be readily measured into appropriate dosing chambers.

Such stability is also very useful in analytical chemistry, where the fumigant is extracted from a commodity into a solvent such as acetone, toluene or water of appropriate pH. This enables determination of residues in the liquid phase and, because of the phase equilibrium distribution, analysis by determination of concentration in the headspace, i.e., in the vapour phase. As in all analytical chemistry, appropriate care is required in preparation of standards and of fortified commodities.

In the section on removal of $C_2N_2$, it was shown that it could be rapidly destroyed by reaction with amines or alcohols. In other sections it was shown that it is stable in certain types of plastic bags and in glass. Thus the stability of the fumigant, as a gas or as a liquid, can be maintained, where required, or conveniently destroyed, where required.

Example 32

Penetration of $C_2N_2$ Through Timber and Sorption of $C_2N_2$ by Timber

Aim: to determine the extent of sorption of $C_2N_2$ by timber, and the extent to which it penetrates timber, and thus, in conjunction with bioassay data against termites, to assess its suitability as a timber fumigant.

Materials and Methods

Timber cubes (100×100 mm) were prepared from two species of timber. These were a softwood species (Oregon) and a tropical hardwood species (Merbein).

To determine sorption, timber cubes were placed in desiccators, of capacity 2.5 L, fitted with a septum inlet and stirred with a magnetic stirrer. Before fumigation, timber blocks were left at 30° C., 55% R.H. for 5 months, in order to obtain the appropriate equilibrium relative humidity. The moisture content, measured by a standard method (American Standard Test Method, 1983), was 11.2% for the hardwood and 10.6% for the softwood. Fumigant was injected into the headspace. Concentrations in the headspace were determined over a period of 100 h after dosing at a calculated concentration of 30 mgL$^{-1}$.

Fumigant concentrations were determined on a Varian 3300 Gas Chromatograph, equipped with a Thermionic Specific Detector, after separation on a DBwax column, of internal diameter 0.53 mm.

To determine penetration through timber, sides of the timber parallel to the grain were sealed with a then layer of silicone sealer, dried, and a thicker layer applied. The cubes were then wrapped in aluminium foil which overlapped the ends, allowing the foil to cover the end-grain surfaces by 5 mm, which was fastened to the timber with a layer of silicone. The blocks were then air-dried for 24 h. Transparent PVC panels (200 mm×105 mm×2 mm) containing sampling septa at each end were fastened to the wood blocks with silicone to construct chambers at each end. The chambers were sealed with silicone. Fumigant was injected at the inlet septum, on one side of the timber block, and sampled at the outlet septum.

Results

Figure 37:
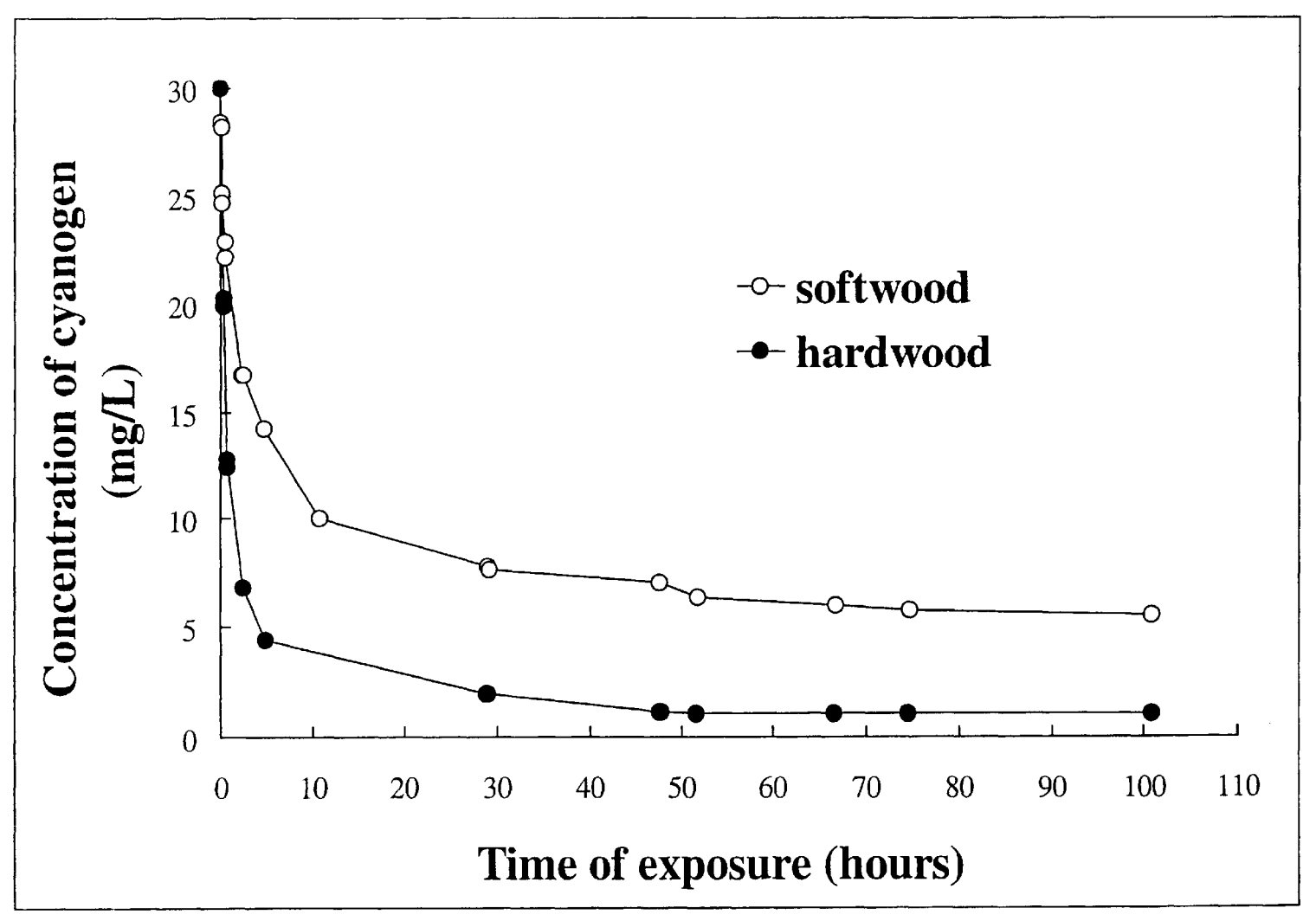

Sorption of $C_2N_2$ on softwood and on hardwood is shown in FIG. 37, which plots $C_2N_2$ concentration in the headspace over both hardwood and softwood. The fumigant was more rapidly sorbed by the hardwood than by the softwood (and similar results were obtained for methyl bromide). The concentration×time product considerably exceeded, for each type of wood, the (C×T) product required to control the three tested species of drywood termites (see Example 36).

Figure 38:
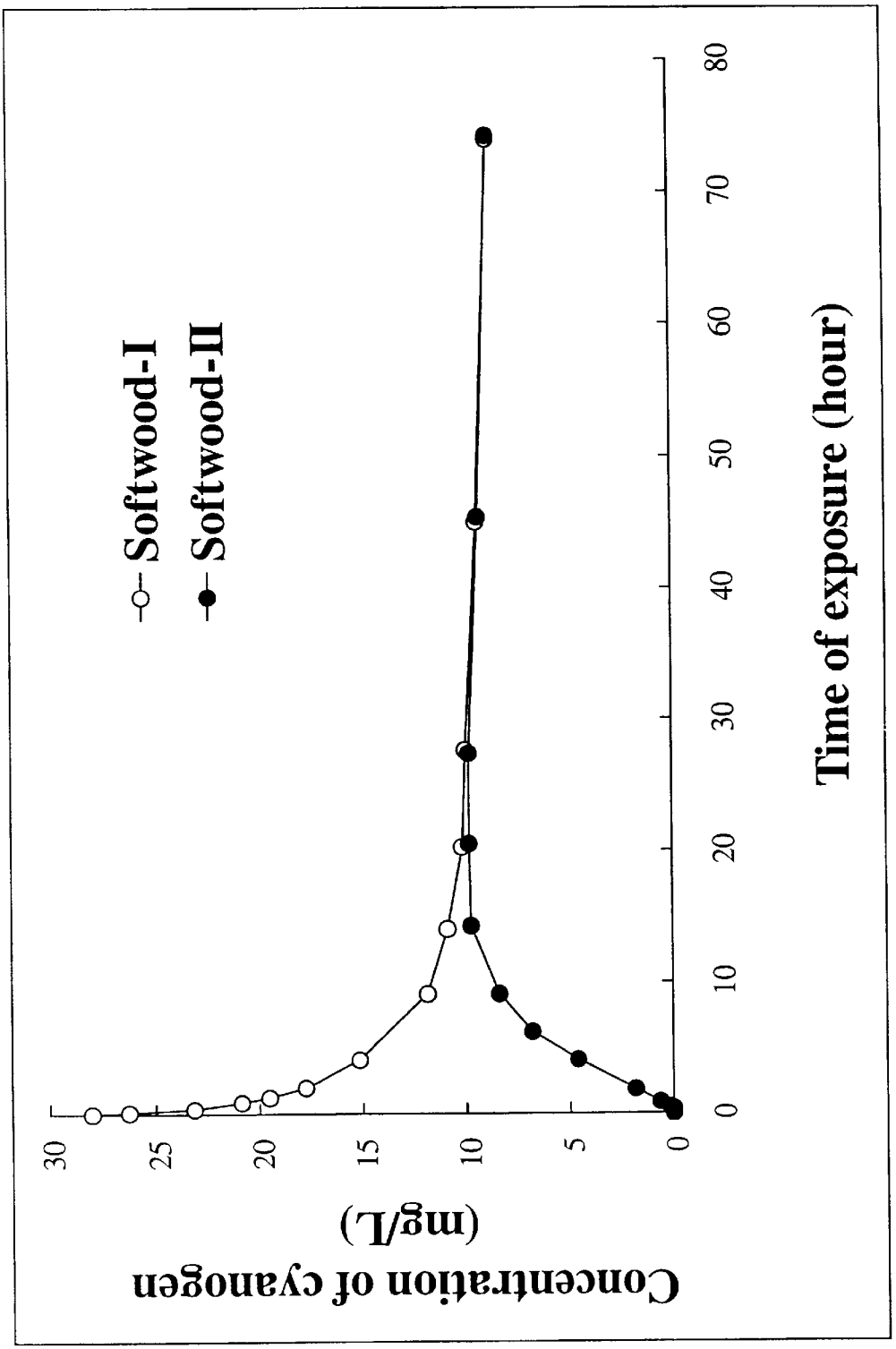
Figure 39:
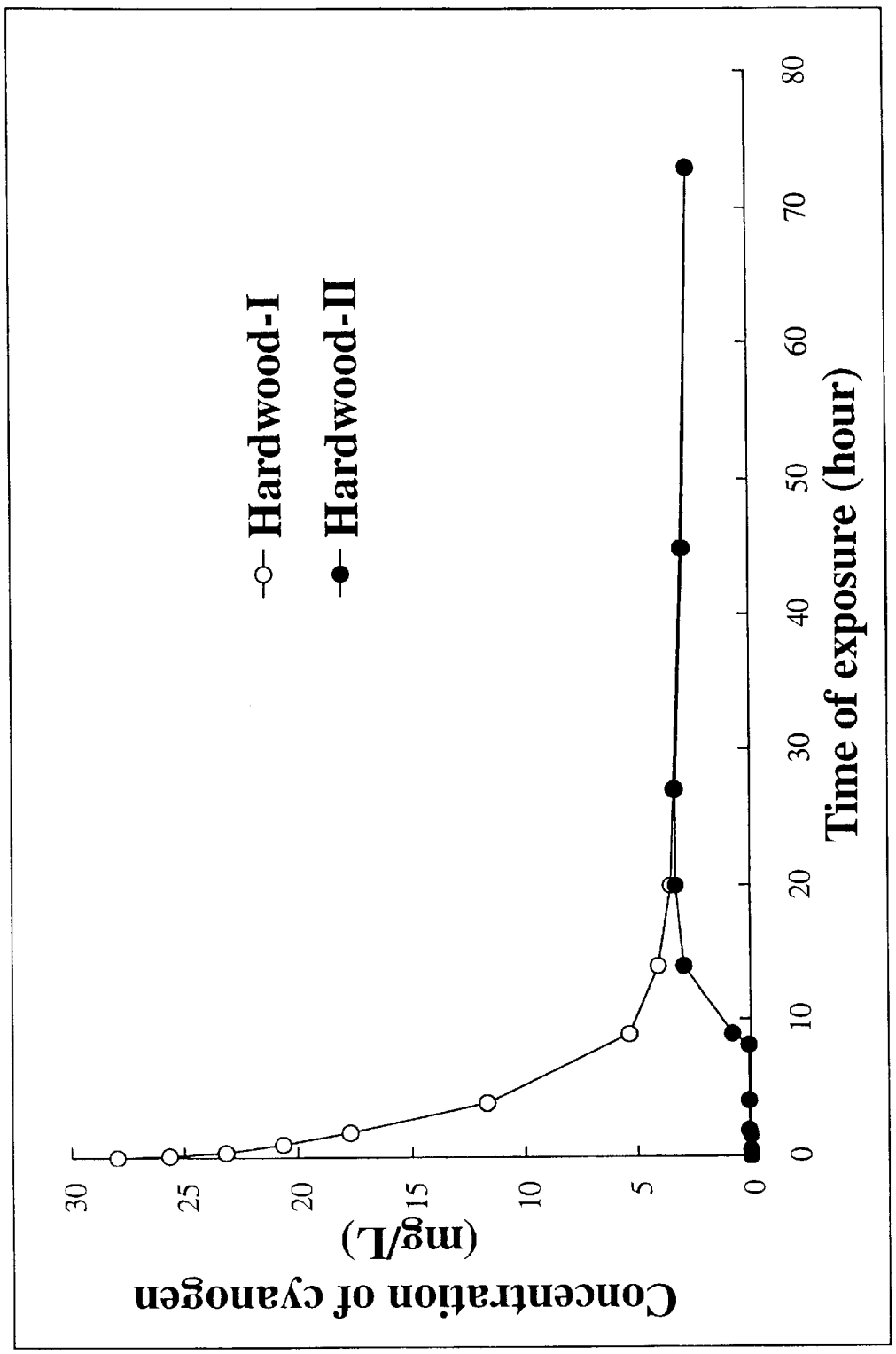

Penetration of $C_2N_2$ through softwood is shown in FIG. 38. After an exposure period of 20 h, concentrations in each chamber were at equilibrium, at a concentration of approximately 10 mgL$^{-1}$. Penetration through hardwood (FIG. 39) was less rapid, and the concentration at equilibrium was lower (2.5 mgL$^{-1}$).

Figure 40:
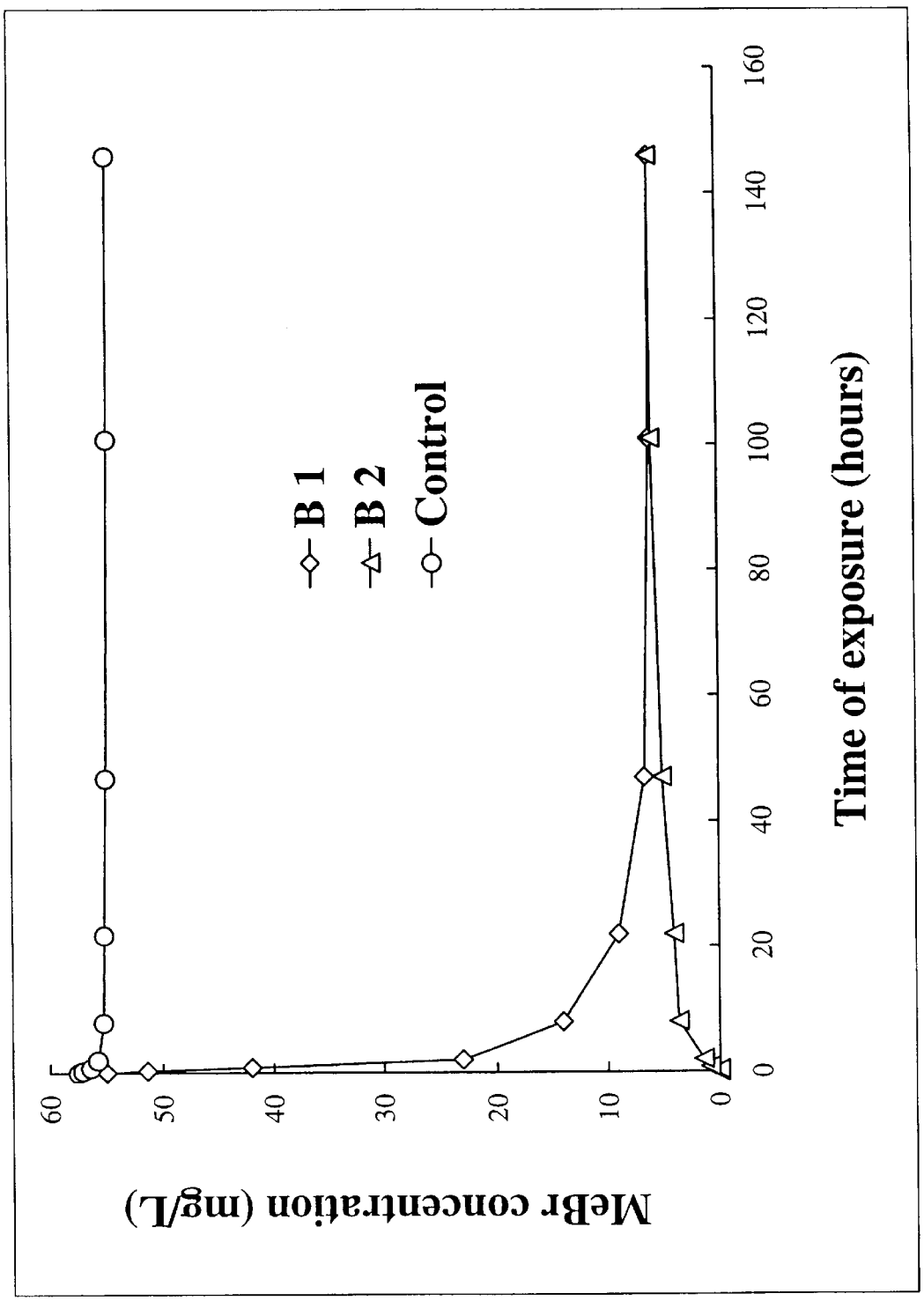
Figure 41:
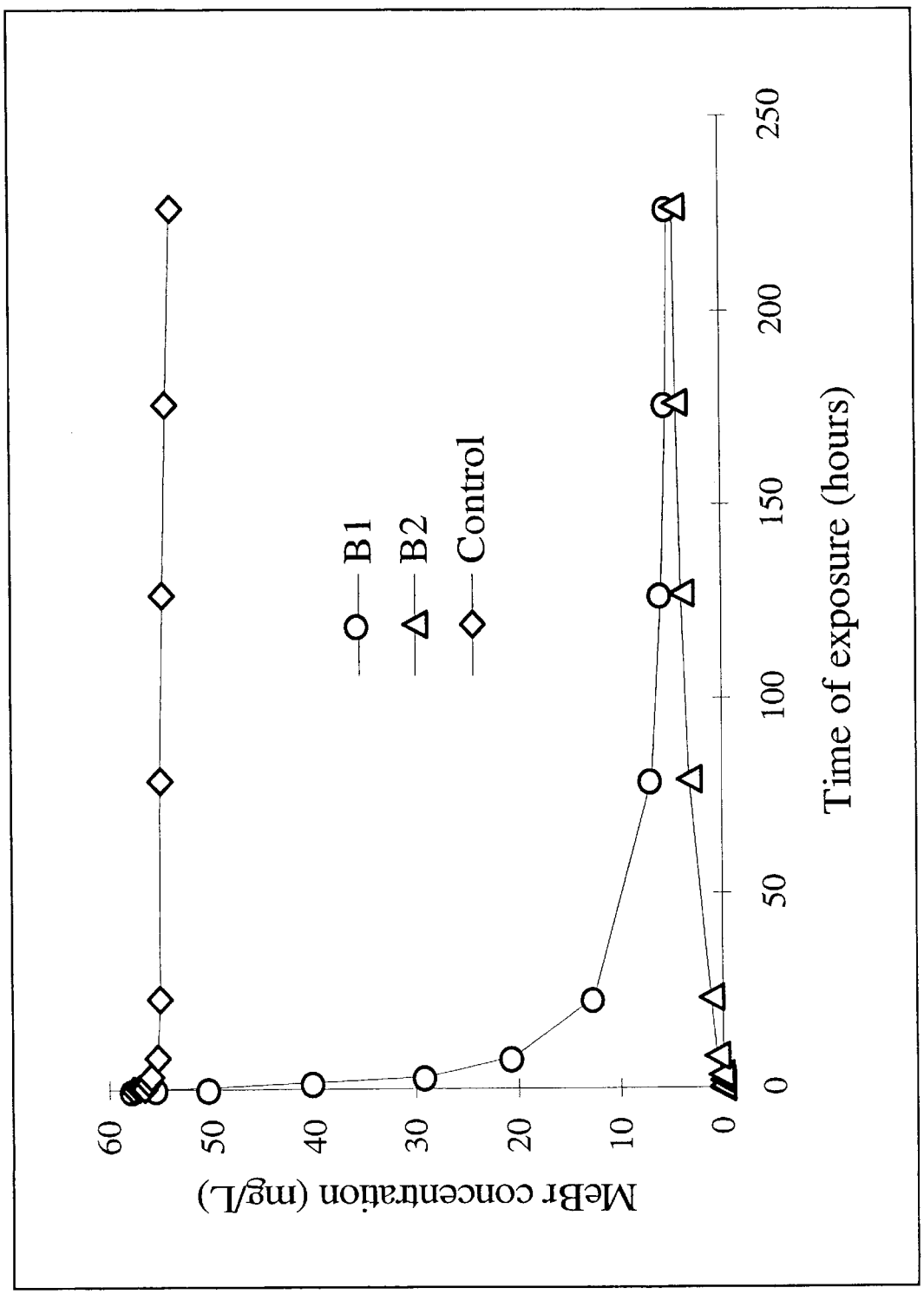

Data for methyl bromide, taken under comparable conditions, are shown in FIGS. 40 and 41. For both hardwood and softwood, the fumigant $C_2N_2$ penetrates timber more quickly than does methyl bromide, and the vapour

Example 33

The effect of $C_2N_2$ Fumigation on the vase Life of Cut Flowers

Aim: To assess the suitability of $C_2N_2$ as a fumigant for cut flowers.

Materials and Methods

Field Carnations and Leucadendrons were purchased from a local wholesale florist.

Fumigations were carried out in sealed 63.5 liter drums using $C_2N_2$ (at a concentration of 1.8 mg $L^{-1}$ for 2 hours), Methyl Bromide (at 32 mg $L^{-1}$ for 2 hours—the dose recommended for the Export Flower Industry by Australian Quarantine Inspection Service—and a control with no fumigant added.

The 63.5 liter drums were each fitted with a sampling port and pump fittings. After dosing, the gaseous contents of the drum were circulated via the pump for 15 minutes to produce an even distribution of fumigant gas through out the drum.

The appropriate concentration of fumigant was achieved by removing a given amount of air from the drum and introducing the same amount of concentrated gas. Concentrations in the drums were verified against standard concentrations (prepared in 1 liter Erlenmeyer flasks with "quick fit" septum tops) using Gas Chromatography. $C_2N_2$ was measured on a Varian 3300 Gas Chromatograph fitted with a thermionic specific detector. DBwax column (0.53 mm diam.) and the Methyl Bromide on a Shimadzu 6AM Flame Ionization Detector fitted with a 20% OV101 on Gas Chrom Q column.

The concentration of each fumigant was checked initially, after one hour and just prior to the completion of fumigation.

After 2 hours the drums were opened and allowed to air in a fume hood, the flowers were removed from the drums, the stems trimmed and the bunches placed in water and left in the fume hood to air for 2 hours then placed in a cool room.

Assessment of the phytoxicity of the fumigants was done after one week of cold storage.

Results

The actual concentrations of fumigant gases achieved were 30 mg $L^{-1}$ MeBr and 1.8 mg $L^{-1}$ NF2. Over the 2 hour fumigation there was a 33% drop in the concentration of $C_2N_2$ due to either sorption or breakdown of $C_2N_2$ by the flowers (see FIG. 42). In contrast the concentration of MeBr remained relatively unchanged throughout the exposure.

The phytoxicity assessments were made by a panel of six people who were asked independently to give a value out of 10 (Where 10 is excellent and 1 is unsaleable) for each flower and each treatment. The figures given below are the averaged results.

| Treatment | Carnation | Leucadendron |
|---|---|---|
| Control | 5 | 7 |
| $C_2N_2$ | 3 | 5 |
| MeBr | 3 | 6 |

Discussion $C_2N_2$ is comparable to MeBr as a fumigant gas for cut flowers. Its efficacy against insects fount in cut flowers is outlined in Example 46.

Example 34

Toxicity of $C_2N_2$ to the External Stages of Stored Product Coleoptera

Aim: to determine $C_2N_2$ toxicity to the external stages of a variety of stored grain Coleoptera pests.

Materials and Methods

Preparation and Analysis of $C_2N_2$ $C_2N_2$ is available commercially as a liquefied gas shipped in gas cylinders. It was however elected to prepare it from stock reagents on the day of use for these preliminary trials. Approximately 50 g of $CuSO_4.5H_2O$ (analaR) was added to 500 ml of distilled $H_2O$. The solution was heated to approximately 90° C. and immediately removed from the hotplate. A bell tube fitted with a septa lid was immersed into the solution and the air removed from the tube via a syringe. To the bell tube was added approximately 10 ml of saturated KCN solution. Generated $C_2N_2$ was allowed to stand for a minimum of 30 minutes prior to sampling.

Purity of $C_2N_2$ was measured on a GOW-MAC gas density detector (model 40-001). Purity was typically between 65–85% with $CO_2$ being the main impurity. $C_2N_2$ concentrations in the glass bottles were monitored using a Varian 3300 Gas Chromatograph fitted with a Thermionic Specific Detector and a DBwax megabore column with an internal diameter of 0.53 mm. An injector temperature of 125° C., a column temperature of 80° C. and a detector temperature of 300° C. was used for all gas sampling.

Insect Species

Insect species tested were *Oryzaephilus surinamensis* (L.), strain NOS405) *Rhyzopertha dominica* (F.), strain Rd2), *Sitophilus granarius* (L.), strain SG4), *Sitophilus oryzae (L.)*, strain CSO418), *Tribolium castaneum* (Herbst), strain TC4), and *Tribolium confusum* (Duv.), strain TCO37). All insects were cultured at 30° C. and 60% relative a humidity except where specified otherwise.

All external stages of these species were tested were the adults of all species, pupae of *T. castaneum* and *T. confusum*, larvae of *T. castaneum* and *T. confusum* and the eggs of *R. dominica*, *T. castaneum* and *T. confusum*.

Bioassay Procedure

Bioassays were performed in 120 ml glass bottles fitted with a Mininert valved lid (Alltech Associates). Assays were performed in duplicate using between 15 and 30 insects of various stages. A quantity of air equal to the volume of gas to be added was removed from the bottles prior to the addition of fumigant. Bioassay bottles were sampled at approximately one hour after the addition of $C_2N_2$ and at approximately two hours before its removal. After fumigation, insects were placed on a small amount of an appropriate culture medium and were allowed to remain at 30° C. and 60% relative humidity for 1 week prior to scoring.

Results

Toxicity of $C_2N_2$ to External Stages of Coleoptera

The toxicity of $C_2N_2$ to the external stages of six species of coleoptera are summarised in Table 18.

The minimum lethal doses shown are generous and further bioassay experiments are likely to show lethal doses which are conceivably much lower. The concentration×time products (CT products) shown are substantially lower than those for a variety of other fumigants. For example, *R. dominica* adults could be controlled with an $C_2N_2$ CT product of 8.82 mghL$^{-1}$ (6hrs., 30° C.) as compared to CT products of 33.0 mghL$^{-1}$ for methyl bromide, 294.0 mghL$^{-1}$ for carbon disulphide, 15.6 mghL$^{-1}$ for hydrogen cyanide, 636.0 mghL$^{-1}$ for ethylene dichloride (Monro, 1967) and 68.7 mghL$^{-1}$ for carbonyl sulphide (Desmarchelier 1994).

Extending the exposure period by a factor of four to 24 hours enabled the dose to be lowered by factors of between approximately 2 (eg. larvae of *T. castaneum*) and 6 (eg. eggs of *T. confusum*). The average factor was 3.2 for adults, 2.0 for larvae, 3.0 for pupae and 3.3 for eggs.

Discussion $C_2N_2$ was effective against all stages of all species of Coleoptera tested. The amount required to kill insects varied with time of exposure, as also shown over a wider range of exposure times in Example 35.

TABLE 28

Toxicity of $C_2N_2$ to External Stages of Coleoptera

| Species | Stage | Exposure (hours) | Minimum Lethal Dose (mgL$^{-1}$)* | CxT (mghL$^{-1}$) |
|---|---|---|---|---|
| O. surinamensis | Adult | 24 | 1.09 | 26.16 |
| R. dominica | Adult | 24 | 0.43 | 10.32 |
| S. granarius | Adult | 24 | 1.12 | 26.88 |
| S. oryzae | Adult | 24 | 0.61 | 14.64 |
| T. castaneum | Adult | 24 | 1.23 | 29.52 |
| T. confusum | Adult | 24 | 1.31 | 31.44 |
| O. surinamensis | Adult | 6 | 1.32 | 7.92 |
| R. dominica | Adult | 6 | 1.47 | 8.82 |
| S. granarius | Adult | 6 | 3.5+ | 21+ |
| S. oryzae | Adult | 6 | 4.5+ | 27+ |
| T. castaneum | Adult | 6 | 2.94 | 17.64 |
| O. surinamensis | Adult | 3 | 2.28 | 6.84 |
| R. dominica | Eggs | 24 | 0.69 | 16.56 |
| T. castaneum | Eggs | 24 | 2.56 | 61.44 |
| T. confusum | Eggs | 24 | 0.73 | 17.52 |
| R. dominica | Eggs | 6 | 1.38 | 8.28 |
| T. castaneum | Eggs | 6 | 4.5+ | 27+ |
| T. confusum | Eggs | 6 | 4.40 | 26.4 |
| T. castaneum | Larvae | 24 | 1.29 | 30.96 |
| T. confusum | Larvae | 24 | 1.28 | 30.72 |
| T. castaneum | Larvae | 6 | 2.59 | 15.54 |
| T. castaneum | Pupae | 24 | 1.40 | 33.6 |
| T. confusum | Pupae | 24 | 1.28 | 30.72 |
| T. castaneum | Pupae | 6 | 4.5+ | 27+ |
| T. confusum | Pupae | 6 | 3.68 | 22.08 |

*The minimum tested dose that caused 100% mortality.

Example 35

Toxicity of $C_2N_2$ for Short and Long Exposures

Aim: to determine the toxicity of $C_2N_2$ for short term exposures and for long term exposures.

Materials and Methods

Test insects (20) were exposed in 275 ml Erlenmeyer flasks, fitted with a septum inlet. The fumigant was injected, and insects exposed for periods between 5 minutes and 14 days. After exposure, insects were transferred to jars containing 20 g of wheat, and kept at 30° C. 55% relative humidity for two weeks prior to mortality assessment.

Test insects were *Rhyzopertha dominica* (F.), strain CRD2, *Oryzaephilus surinamensis* (L.), strain NOS405 and *Tribolium castaneum* (Herbst), strain CTC4.

Results

Mortality at the end of the exposure period (acute) and after a holding period of 2 weeks is recorded in Table 19.

Significant mortality was achieved after a holding period of only 5 minutes, and 100% mortality after a holding period of 10 min. In contrast, long exposure to a low concentration resulted in 100% mortality in a system where carbon dioxide concentration increase.

Discussion

The fumigant $C_2N_2$ is able to kill extremely quickly, and also to kill at low doses, over long exposure periods. Thus it can be used in a variety of situations. The data also indicate that there is no clear relationship between acute mortality (or knockdown) and final mortality (see Example 30).

TABLE 19

Toxicity of $C_2N_2$ over different exposure periods

| Exposure period | Applied fumigant (mgL$^{-1}$) | Strain | Acute Mortality (%) | Mortality at 2 weeks (%) |
|---|---|---|---|---|
| 5 min | 17 | CRD2 | 100 | 20 |
| 5 min | 17 | NOS405 | 100 | 50 |
| 5 min | 17 | CTC4 | 95 | 0 |
| 10 min | 30 | CRD2 | 100 | 100 |
| 10 min | 17 | CTC4 | 95 | 0 |
| 10 min | 17 | NOS405 | 100 | 90 |
| 10 min | 17 | CRD2 | 100 | 80 |
| 20 min | 30 | CRD2 | 100 | 100 |
| 14 days | 0.01 | CRD2 | 0 | 100 |

Example 36

Evaluation of $C_2N_2$ and Phosphine Toxicities to Dry Wood Termites with Reference to Methyl Bromide Aim: To evaluate the toxicity of $C_2N_2$ and phosphine to three species of dry wood termites, namely *Cryptotermes brevis*, *Cryptotermes cyanocephalos* and *Cryptotermes domesticus*, as potential replacements for methyl bromide.

Materials and Methods

Termites were obtained from cultures kept at 30° C. and 80% RH. Termites were transferred to 120 mL bottles fitted with Mininert valved lids and a 325 mg chip of plywood and sealed whilst at 80% RH and 30° C. All fumigations were performed in duplicate with a sample size of 10–11 insects for *C. brevis*, 25 insects for *C. cyanocephalos* and 22 insects for *C. domesticus*. An appropriate volume of air was removed from the sample bottles prior to the addition of fumigants. Dosed samples were analysed on a gas chromatograph to ensure concentrations were as predicted. A second set of gas chromatograph readings was taken prior to airing to ensure fumigant concentrations had remained static throughout the exposure period. All fumigations were maintained at 30° C. for 24 hours except while undergoing gas chromatograph analysis which took place at 25° C.

$C_2N_2$ concentrations were measured on a Varian 3300 Gas Chromatograph equipped with a Thermionic Specific Detactor after separation on a DBwax column of internal diameter 0.53 mm. Phosphine concentrations were measured on a Shimadzu 6AM equipped with a Flame Photometric Detector. Methyl bromide concentrations were measured on a Shimadzu 6AM equipped with a Flame Ionisation Detector after separation on a GasChromQ with 20% OV-IO1 column.

After 24 hours exposure, termites and wood chips were transferred to plastic Petri dishes each containing a large piece of plywood. Initial and one week survivals were recorded.

Results

Figure 42:
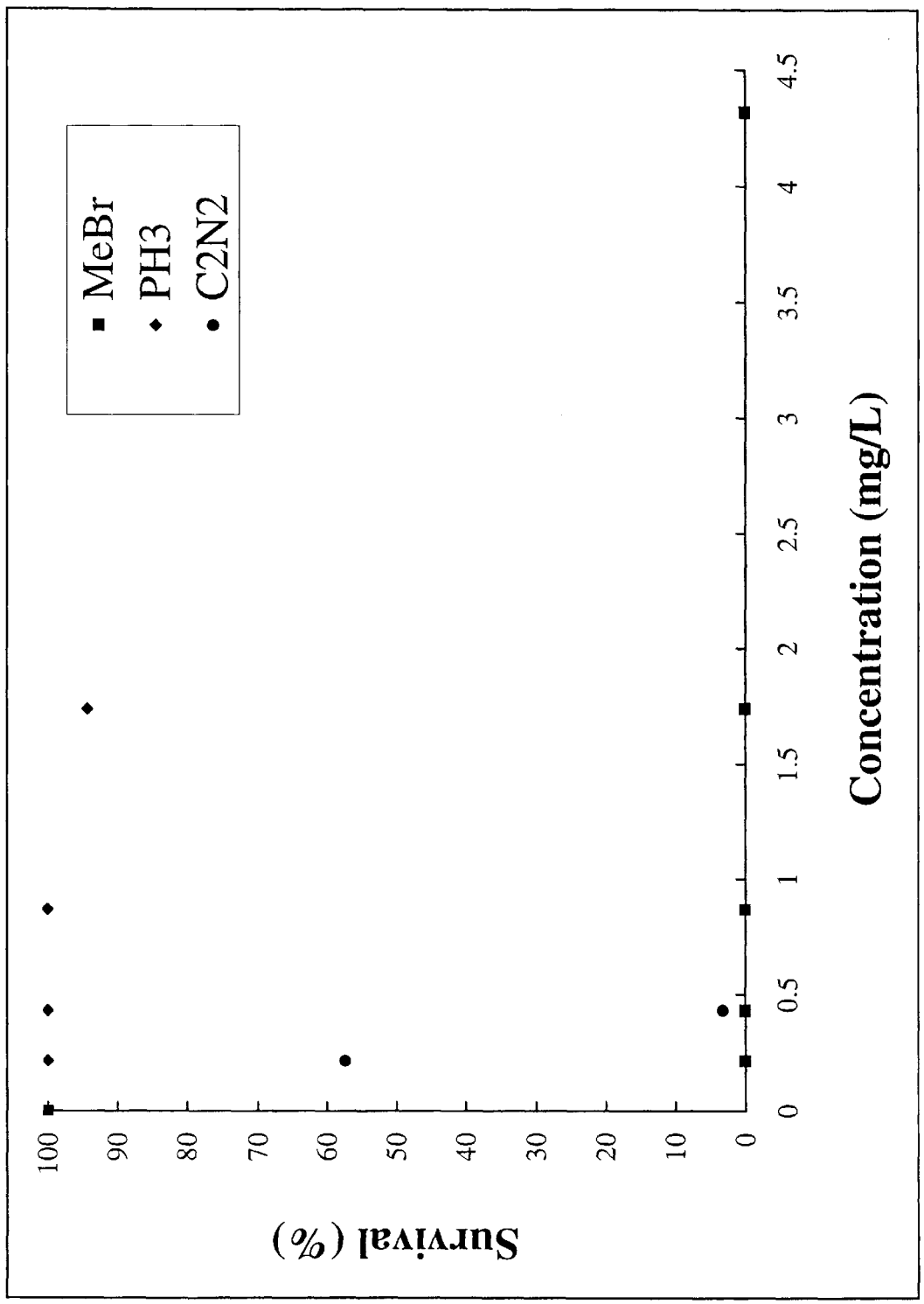
FIGS. 42 to 44 show the toxicity of $C_2N_2$ to three species of dry wood termites.
Figure 43:
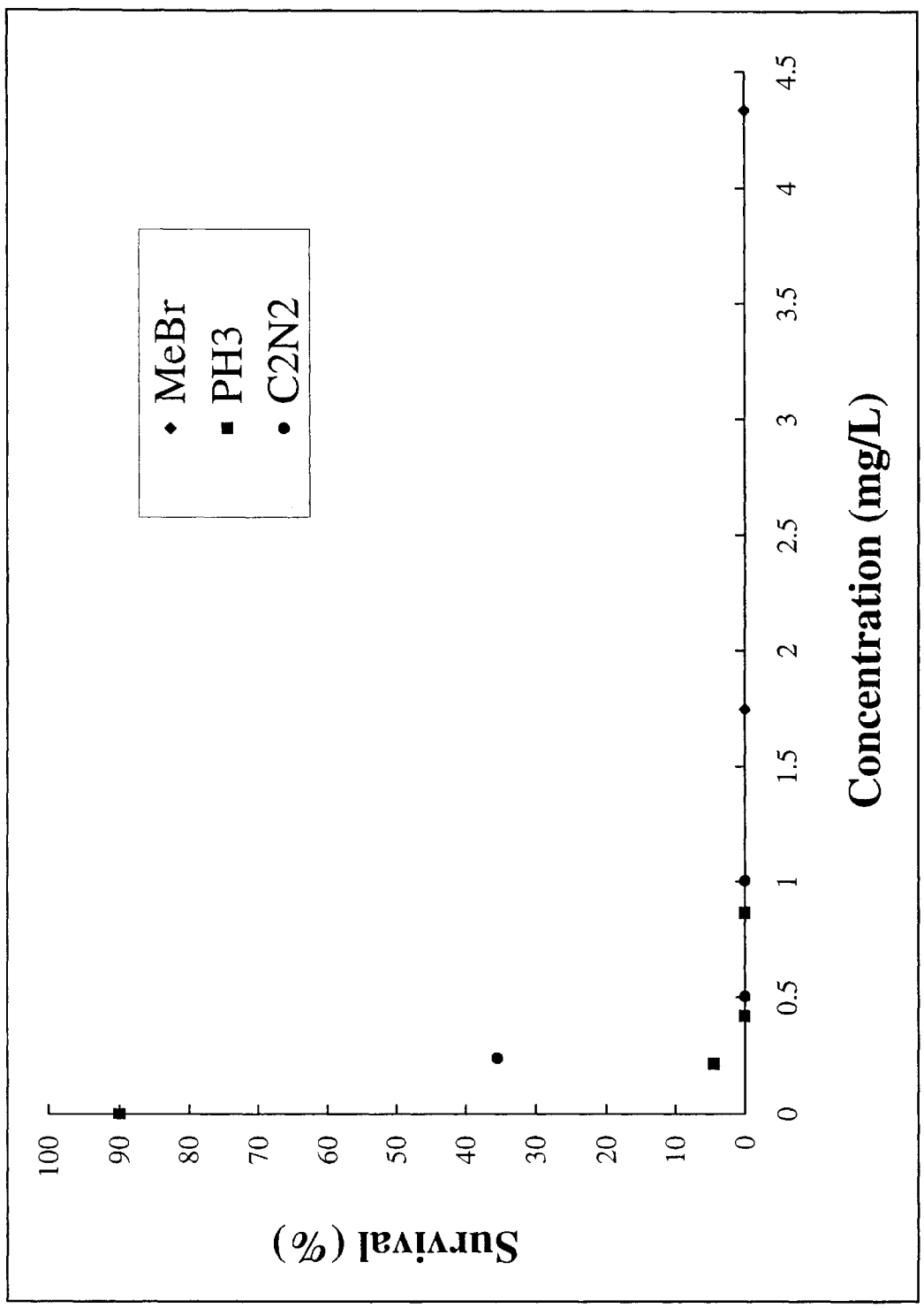
Figure 44:
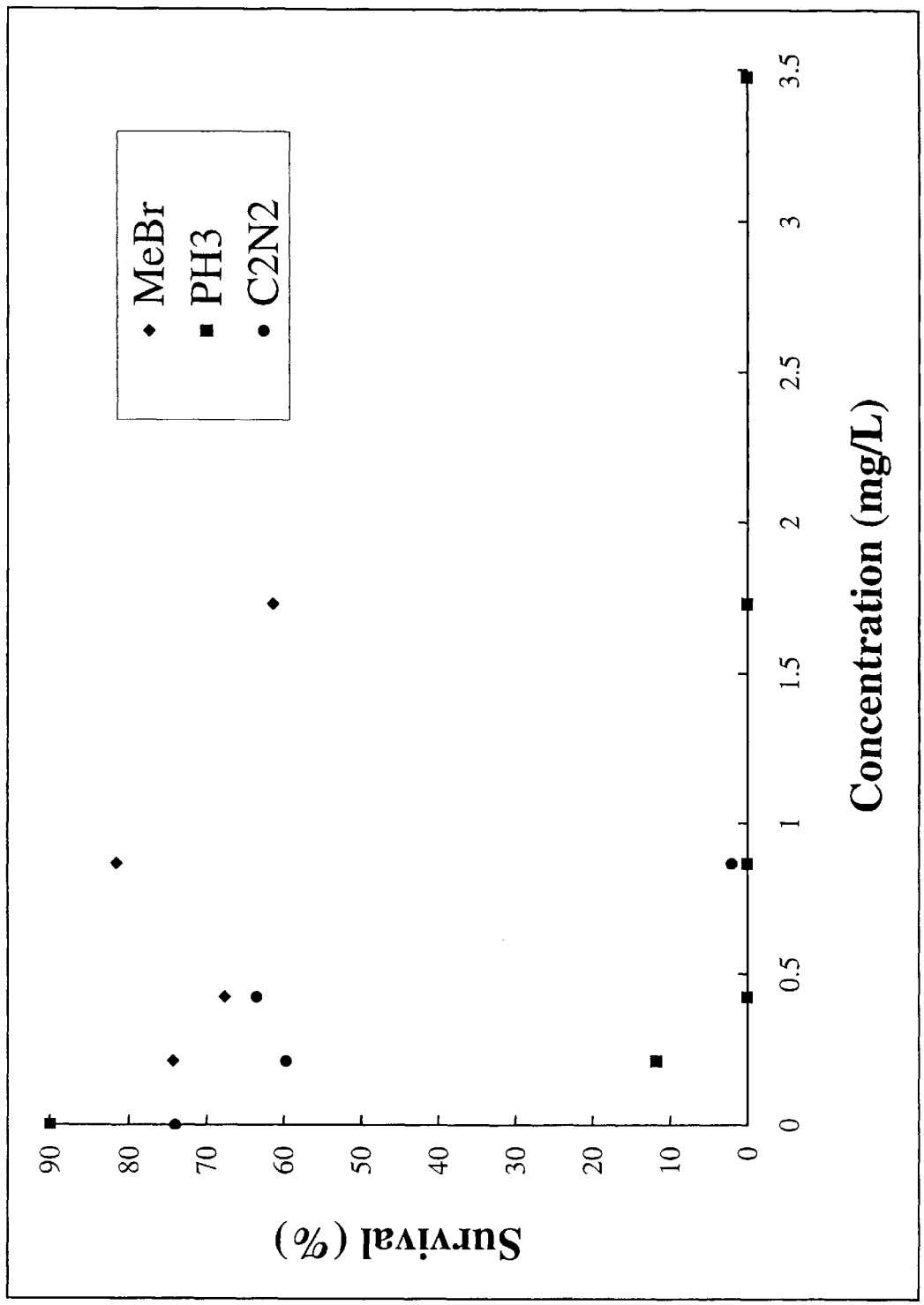
Figure 45:
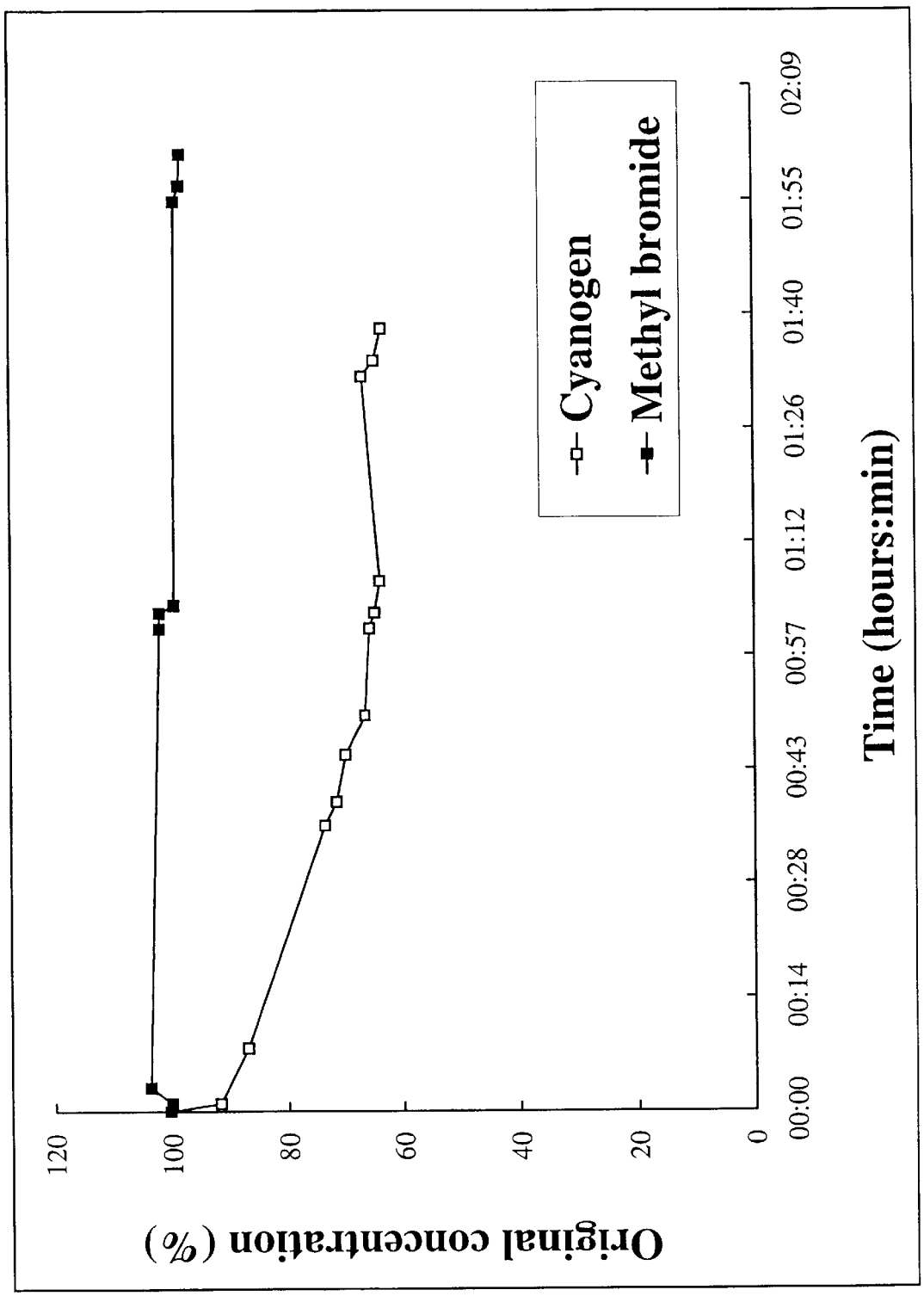
FIG. 45 illustrates the sorption of $C_2N_2$ by cut flowers.

Fumigation results for *C. domesticus C. brevis, C. cyanocephalos* and are summarised in FIGS. 42–44 respectively based upon survivals after one week.

A 100% mortality for *C. domesticus* was obtained after 24 hours fumigation with an $C_2N_2$ applied concentration of 0.87 mgL$^{-1}$, a phosphine applied concentration of 0.22 mgL$^{-1}$ and a methyl bromide applied concentration of 4.35 mgL$^{-1}$ (FIG. 42).

A 100% mortality for *C. brevis* was obtained after 24 hours fumigation with an $C_2N_2$ applied concentration of 0.43 mgL$^{-1}$, a phosphine applied concentration of 0.43 mgL$^{-1}$ and a methyl bromide applied concentration of 1.74 mgL$^{-1}$ (FIG. 43).

A 100% mortality for *C. cyanocephalos* was obtained after 24 hours fumigation with an $C_2N_2$ applied concentration of 1.74 mgL$^{-1}$, a phosphine applied concentration of 0.43 mgl$^{-1}$ and a methyl bromide applied concentration of 3.47 mgL$^{-1}$(FIG. 44).

Discussion

This study demonstrated that the fumigants $C_2N_2$ and phosphine have superior toxicities to methyl bromide for at least three species of dry wood termites and are subsequently viable candidates for replacing methyl bromide for dry wood termite control.

Of the potential alternatives to methyl bromide for timber fumigation, phosphine requires long exposures to control all stages of Coleoptera, though not to control dry-wood termites, and sulfluryl flouride is relatively ineffective against eggs of most tested species. In contrast, as shown in other examples especially Example 34 and Example 35, $C_2N_2$ can act quickly and can kill eggs and all other stages of Coleopteran and other orders. Example 32 shows that the concentration of $C_2N_2$ applied to chambers containing hardwood or softwood achieved concentration by time products well in excess of those needed to control termites.

Example 37

Reaction of Amines with $C_2N_2$

Aim: to determine whether the reaction of $C_2N_2$ with amines was reversible, ie if the amine could be considered as a catalyst, and would be recovered without change. This work is relevant to the possible loss of amines of nutritive value, such as lysine.

Materials and Methods

Benzylamine was used a model amine partly because lysine cannot be determined by HPLC using a UV detector.

Benzylamine (0.04 M) in methanol (20 mL) was placed in a 275 mL Erlenmeyer flasks with a septum inlet. The fumigant $C_2N_2$ was injected (0.5 mL). The benzylamine was determined by High Performance Liquid Chromatography (HPLC) at timed intervals after the addition of fumigant. More fumigant (5 mL) was then added, and the procedure repeated.

The HPCL analyses used an Alltech Ultima C18 250 mm×4.6 mm column, and a Shimadzu SCI-61A system controller. Analysis was by absorption, using a Waters 490E programmable multiwavelength detector. The mobile phase was 20% acetonitrile, 80% water to 100% acetonitrile over 20 min, at a flow rate of 1 mL/min.

Results

The HPLC spectrum, 26 h after addition of 0.5 mL of $C_2N_2$, showed 3 extra peaks. These had disappeared after 47.5 hours, and again after 53.5 h. At each of these intervals, the spectrum of the "product" was identical to that of benzylamine. This is in contrast to the reaction of benzylamine with another fumigant, carbon bisulphide, where labile peaks were again identified, but the benzylamine was not recovered.

After addition of 5 mL of $C_2N_2$, the benzylamine was again quantitatively recovered.

0.5 mL of $C_2N_2$ gas contains $2.2 \times 10^{-5}$ of fumigant, and the number of moles of benzylamine was 36 times this level. This ratio was reduced to 3.6, when 5 mL of fumigant was added. As two moles of amine can react with one mole of benyzlamine, the mole ratio used was more than adequate to detect irreversible changes.

Discussion

The rapid reaction of amines with $C_2N_2$ was discussed in Examples 14 and 15. The reversible nature of the reaction of amines (eg lysine) with $C_2N_2$ indicates that such biological chemicals are not destroyed, and thus causing a nutritive loss.

Example 38

$C_2N_2$ as a Fumigant for Use on Cut Flowers, and Related Uses

Aim: To assess the ability of $C_2N_2$ to act as a fumigant against insects commonly found on cut flowers.

Materials and Methods

Insects were collected from freshly cut flowers (Protea and Thryptomene) and placed into glass vials (approximate capacity 8 mL) and sealed with lids containing a septum. Vials with representative samples of each insect order were kept as controls and the remainder were dosed with 1 mL of $C_2N_2$ of a concentration of 92 mgL$^{-1}$ giving a final concentration of approximately 11.5 mgL$^{-1}$. These vials were left at ambient temperature (approximately 18° C.) for 2 hours. After that time had elapsed the insects were checked for signs of life then aired and preserved for further identification.

Results

The control vials showed no mortality over the two hour period whilst all of the insects, mites and spiders exposed to $C_2N_2$ were dead after the two hour exposure.

| Insect (Common Name) | (Order) | (Family) | No. Alive | No. Dead |
|---|---|---|---|---|
| Thrips | Thysanoptera | phaleothripida | 0 | 15 |
| Leaf beetle | Coleoptera | chrysomalidae | 0 | 1 |
| Springtails | Colembola | | 0 | 10 |
| Moths | Lepidoptera | geometridae | 0 | 2 |
| Moth (larva) | | | 0 | 1 |
| Mites | Acarina | | 0 | 8 |
| Spiders | Arachnida | | 0 | 6 |
| Flies | Diptera | sciaridae | 0 | 6 |

Discussion

These preliminary results indicate that $C_2N_2$ will kill these insects, spiders and mites commonly found on cut flowers, growing plants and elsewhere. Insects controlled were from the orders Thysanoptera, Coleoptera, Colembola, Lepidoptera and Dipters. Other major orders killed were Aracina (mites) and Aracnida (spiders). Cross reference is made to control of Coleoptera (e.g. Example 30, Example 34), Lepidoptera (Example 27), Diptera (Example 12) and Acarina (Example 40).

Example 39

Effect of $C_2N_2$ on Insects at Different Atmospheric Pressures

Aim: To determine the effect of high and low pressure on the toxicity of $C_2N_2$. Two different stored product pests, *Sitophilus oryzae* and *Rhyzopertha dominica*, were treated with $C_2N_2$ in stainless steel vessels where the pressure was held at ambient, one atmosphere above ambient or one half an atmosphere below ambient. End point mortalities were determined for the two species after 24 h exposure to a given amount of $C_2N_2$ at the three different pressures.

Materials and Methods

Figure 46:
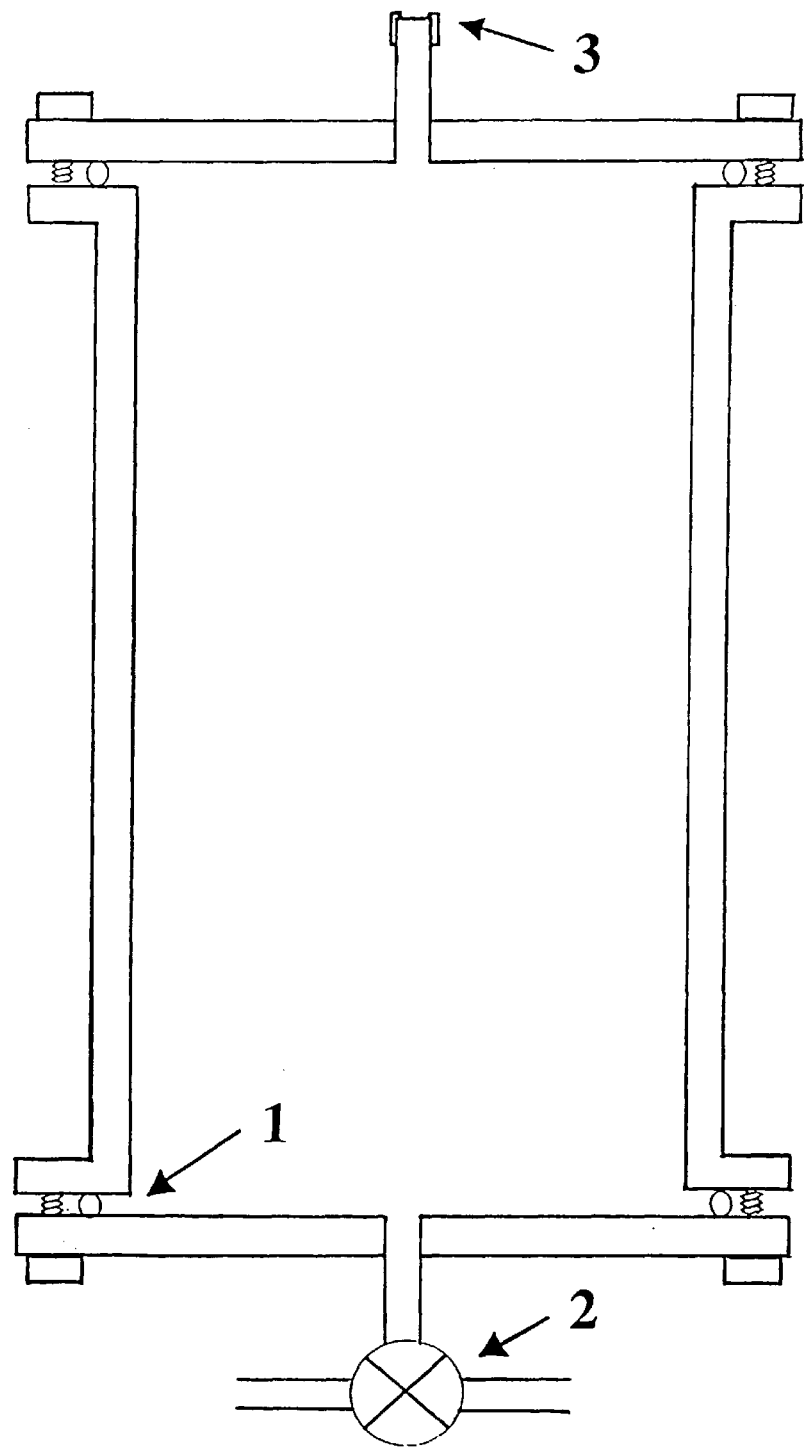
FIG. 46 shows a fumigation apparatus used in measuring the effect of high and low pressure on the toxicity of $C_2N_2$ on insects.

Fumigations were carried out in stainless steel cylinders. Stainless steel cylinders (approx. 100 mm diam.×353 mm) were fitted with end plates secured by bolts and sealed with rubber O-rings. Each end plate had a ¼ inch inlet (outlet) tube which allowed the connection of a three-way tap or a rubber septum sampling port. The apparatus is shown in FIG. 46. Cylinder volumes were calculated from the weight of water in a filled cylinder.

Mixed age adults were taken from laboratory cultures of *Sitophilus oryzae* (Strain LS2) and *Rhyzopertha dominica* (Strain CRD2). These were placed, 20 to a container, in small glass tubes (25 mm diam.×25 mm) capped both ends by fine stainless steel mesh. Three containers of each species (i.e. 6 containers, 120 insects) were placed in a stainless steel cylinder which was then closed. Cylinders to be dosed at atmospheric pressure or above were partially evacuated (pressure reduced by 5–10 mm Hg) and then the measured amount of fumigant was introduced by injection through the septum. The pressure was then allowed to equalise with atmospheric pressure. Elevated pressure s were achieved by connection to a cylinder of air until the required pressure was achieved. Low pressure cylinders were evacuated to the required pressure, measured with a Hg manometer, before the injection of the fumigant. When loading or unloading the cylinders, all pressure changes were carried out over at least one minute in order to avoid insect damage resulting from rapid pressure change (Ulrichs, 1994; Nakakita and Kawashima, 1994). The absolute amount of $C_2N_2$ used was either 0.94, 0.4, 0.2 or 0.1 mg per 'cylinder liter'. A control was kept for each treatment cylinder. After 24 h fumigation the fumigant concentration in the cylinders was checked by gas chromatography, the insects were removed from the treatment and control cylinders and survivors were counted. The insects were kept until end-point mortalities could be determined.

Results

The results are shown in Table 20. *R. dominica* was most susceptible to $C_2N_2$ and 100% mortality was achieved for nearly all doses. At 0.1 mg/L the mortality was 63%. The toxicity of $C_2N_2$ for the less susceptible *S oryzae* was found to depend on the concentration of the fumigant expressed as a dose at NTP. That is, for the same dose (mg) per container, the toxicity was found to be lower at higher pressure, or conversely, in terms of absolute amounts of fumigant, the toxicity of the fumigant increases with decreasing pressure. On the other hand, when the dose is expressed as a dose at NTP, equivalent doses are found to have the same toxicity (see Table 20).

Discussion

The data in Table 20 indicate the toxicity of $C_2N_2$ is enhanced by lowering the air pressure in the fumigation chamber. The reason for this has not been proved, however it is possible that the toxicities reflect the $C_2N_2/O_2$ ratios which were used. When the doses and pressures are corrected to doses at NTP (Table 1), it is apparent that pressure per se is not the governing parameter as equivalent doses (at NTP) give close to equivalent responses. Change in atmospheric pressure, while holding the absolute dose of fumigant constant, effectively alters the $C_2N_2/O_2$ ratio. That is, for the same dose, the fumigation at high pressure has a lower $C_2N_2/2$ ratio than that at low pressure and mortalities at high pressure are correspondingly lower than those at low pressure. The present results contrast with those of Bond (1962) who suggested that exposure to increased oxygen levels increases the toxicity of hydrogen cyanide to insects.

The data illustrate the ability to use $C_2N_2$ at either high or how pressures.

TABLE 20

Relationships between mortality concentration and pressure in $C_2N_2$ fumigation of *Sitophilus oryzae*

| | Mortality (%), Dose at NTP | | |
|---|---|---|---|
| dose/container | 2 atmos. | 1 atmos. | 0.44 atmos. |
| 0.94 mg/L | 94% | 100% | |
| | 0.47 mg/L | 0.94 mg/L | |
| 0.4 mg/L | 58% | 92% | 100% |
| | 0.2 mg/L | 0.4 mg/L | 0.8 mg/L |
| 0.2 mg/L | 0% | 57% | 97% |
| | 0.1 mg/L | 0.2 mg/L | 0.4 mg/L |
| 0.1 mg/L | | 0% | 33% |
| | | 0.1 mg/L | 0.2 mg/L |

Example 40

Control of Mites with $C_2N_2$

Aim: to determine the efficacy of $C_2N_2$ against mites.

Materials and Methods

Mites were placed in 270 mL Erlenmeyer flasks containing a small amount of food conditioned at 65% relative humidity. The food was organic rice bubbles plus yeast. The fumigant was injected through a septum inlet.

"Knockdown" mortality was observed at timed intervals, that is, the number of immobile mites was assessed. At the end of the exposure period, mite mortality was assessed, and again after holding periods on food conditioned at 65% relative humidity.

The species of mite tested was *Tyrophagus putrecentiae*, a cosmopolitan detritus feeder, of the sub-order Astigmata.

Results

Results are summarised in Table 21. Complete knockdown was achieved at low concentration by time products. Mites were completely killed from exposures to 1 $mgL^{-1}$. For low exposures, eg for 6 h exposure to 1 $mgL^{-1}$, dead mites appeared normal, but did not move. At high concentrations, or after longer exposure periods, mites appeared shrivelled.

Discussion

Control of mites in fumigation chambers correlates with control of mites during flower fumigations (see example 38), under conditions where phosphine, failed to achieve control. The ability to kill both mites and insects is important in many area, including stored durable and perishable commodities, museums, etc.

TABLE 21

Mortality of *T. putrecentiae* exposed to $C_2N_2$

| Species | Concentration (mg/L) | Exposure period (h) | Knockdown (%) | Mortality (%) (24h post-assay) |
|---|---|---|---|---|
| | 2 | 2 | 95 | — |
| | 4 | 18 | 100* | 100* |
| | 2 | 18 | 100* | 100* |
| | 1 | 6 | 50 | 50 |
| | 1 | 18 | 100 | 100* |
| | 1 | 24 | 100 | 100* |
| | 1 | 48 | 100* | 100* |

*shrivelled

Example 41

Control of Plant Diseases with $C_2N_2$

Aim: to determine the efficacy of $C_2N_2$ against plant diseases.

Materials and Methods

Standard medium for propagation of plant fungi, potato-dextrose agar plates plus glucose, were prepared in Erlenmeyer flasks, of capacity 275 mL, equipped with Quickfit connections with sampling septa. The whole equipment, including the top, had previously been sterilized at 130° C. The centre of each plate was innoculated with plant fungi. Fungi used were the take-all fungus, *Gauemannomyces graminis* var. *tritici* and *Rhizoctonia solani*.

The former fungus is a major cause of loss of yield in wheat and the latter fungus is a common cause of yield loss in many situations.

The fumigant $C_2N_2$ was added to the flasks through the sampling septum. Calculated applied concentrations, in experiments to control *G. graminis*, were 0.6, 2.4, 6 and 15 $mgL^{-1}$, as well as a control. The flasks were left at 22° C. The tops were removed after 24 h, to allow the airing of any residual fumigant, and then replaced. Calculated applied concentrations, in experiments to control *R. solani*, were 0.78, 1.56, 3.1 and 12.5 $mgL^{-1}$, but initial measure concentrations were only 0.50, 1.0, 2.15 and 8.7 $mgL^{-1}$.

All experiments were performed in duplicate.

Results

*G. graminis*

After 48 h. fungal growth was clearly visible in the controls, but not in any of the treatments. Over each of the next 3 days, growth in the control progressed, but no growth was observed in any of the fumigated fungi.

With *R. solani*, colony diameter at time of dosing was between 10 and 12 mm in all cases, and diameters were recorded. One day (24 h) after dosing, the colony diameters in fumigated samples had not changed, whereas the control diameter had increased to 29 mm. After 72 h. there was some growth in the samples fumigated at a calculated concentration of 0.8 $mgL^{-1}$, to an average diameter of 27.5 mm, whereas there was no growth in samples fumigated at the higher concentrations. The average diameter in control samples was 61 mm.

Discussion

Control of plant pathogens is an important area of horticulture and agriculture, and is a major reason for the current usage of methyl bromide on soils.

Cross Reference

Examples 7 and 42 discuss sorption in soil and efficacy in soil. Control of moulds on wheat (Examples 21 and 41) are also relevant. The fumigant can be applied either as a gas or in solution, and each method of application has potential uses for soil fumigation.

Example 42

Sorption of $C_2N_2$ on Soil

Aim: to determine the sorption of $C_2N_2$ in soils, using the soils used from previous studies on other fumigants (Mathiesson, Desmarchelier, Shakelton and Vu, unpublished results) and used in the assessment of the toxicity of $C_2N_2$ to whitefringed weevil (see Example 7).

Materials and Methods

Three types of soils were tested. These were Pemberton loam, Myaluys sand and Sadie peat.

Soil (50 g) was placed in Erlenmeyer flasks, capacity 138.5 mL. The flasks were sealed with a septum inlet. The fumigant was applied in two ways. One method was as a gas, by injection of 1 mL or 0.5 mL. The other method was to apply the same amount of fumigant in an aqueous solution, obtained by adding 10 mL of fumigant gas to 20 mL of 0.01M HCl in a 25 mL Erlenmeyer flasks.

The headspace concentration of fumigant was determined on a Varian Gas Chromatograph, equipped with a thermionic specific detector, after separation on a DBwax column, of internal diameter 0.53 mm.

Experiments were performed in duplicate, the average result recorded.

Results

Results are summarised in Table 22. For each method of application, the concentration of fumigant in the headspace fell more rapidly in the peat soil than in the other soils. The initial concentration of fumigant in the headspace was greater for the addition of the fumigant as gas than in aqueous solution.

Discussion

These results, together with those outlined in Example 7, are consistent with the use of $C_2N_2$ as a soil fumigant, whether applied as a gas or as a liquid. The ability to apply $C_{2N2}$ as a gas or as a liquid is an unusual property of this fumigant.

The loss of $C_2N_2$ on soils, as measured by sorption, is good from the point of view of reduced release of gas to the environment, although it makes pest control more difficult.

The C×T products achieved on the loam and the sand exceeded those needed to control take-all fungus (see Example 41), although this is indicative only, because of the differences in bioassay conditions.

TABLE 22

Sorption of $C_2N_2$ by soils

| Soils | Calculated amount added (mg) | Method of application | $C_2N_2$ concentration in headspace ($mgL^{-1}$) at time (h) | | | |
|---|---|---|---|---|---|---|
| | | | 0 | 1.5 | 5 | 24 |
| M | 0.851 | dry | 5.03 | 0.96 | 0.15 | 0.013 |
| P | 0.851 | dry | 5.16 | 3.29 | 1.12 | 0.003 |

TABLE 22-continued

Sorption of $C_2N_2$ by soils

| Soils | Calculated amount added (mg) | Method of application | $C_2N_2$ concentration in headspace (mgL$^{-1}$) at time (h) | | | |
|---|---|---|---|---|---|---|
| | | | 0 | 1.5 | 5 | 24 |
| S | 0.851 | dry | 4.69 | 0.005 | 0 | 0 |
| M | 1.90 | dry | 12.54 | 1.73 | 0.43 | 0.043 |
| P | 1.90 | dry | 11.25 | 7.25 | 4.80 | 0.15 |
| S | 1.90 | dry | 11.05 | 0.01 | 0.002 | 0 |
| M | 0.423 | wet | 2.07 | 0.55 | 0.06 | 0.004 |
| P | 0.423 | wet | 1.99 | 1.45 | 0.28 | 0 |
| S | 0.423 | wet | 1.22 | 0.009 | 0 | 0 |
| M | 0.964 | wet | 2.42 | 0.91 | 0.14 | 0.01 |
| P | 0.964 | wet | 2.81 | 2.08 | 0.81 | 0.002 |
| S | 0.964 | wet | 2.70 | 0.0055 | 0.001 | 0 |

Example 43

The Extent of Conversion of $C_2N_2$ to Hydrogen Cyanide in Wheat

Aim: to study the extent to which $C_2N_2$ is converted to cyanide in grain.

Introduction

In Example 15, it was shown, from a review of the literature data, that cyanogen can be degraded by two pathways. The first, to formates plus cyanide, predominates at low or high pH but the second, to oxalates without cyanide, predominates at neutral pH.

Materials and Methods

Cyanide in wheat was determined by the method of Vu and desmarchelier. This method uses a standard procedure (American Association of Cereal Chemists, 1983) to remove cyanide from wheat by distillation over water and trapping in dilute alkali. It captures the desorbed hydrogen cyanide in a flask which is sealed, then acidified, to enable determination of hydrogen cyanide in the headspace. Note that this method determines, as is normal practice, all compounds that can decompose to give cyanide, under the conditions employed, and calculates such chemicals as hydrogen cyanide.

In addition, cyanide levels in different grains legumes were determined by the same procedure, from the mean of determinations repeated 5 times.

Australian standard white wheat, 11.6% moisture, was placed in 120 mL flasks which were 95% full of wheat. Flasks were sealed with a Mininert valve. Fumigant was injected and the wheat stored for different periods of time. In addition, fumigated wheat was germinated to assess the effects of germination on residues of hydrogen cyanide.

Both hydrogen cyanide and $C_2N_2$ were measured on a Varian 3300 Gas Chromatograph, equipped with a thermionic specific detector, after isothermal separation on a DBwax column at 60° C.

Experiments were performed in triplicate, and the mean result is recorded.

Results

Residues of cyanide in different grains were, on average, 0.046 mg/kg for wheat, 0.11 mg/kg for canola, 0.058 mg/kg for field peas, 0.125 mg/kg for barley and 1.1 mg/kg for sorghum.

Residues of cyanide subsequent to fumigation with $C_2N_2$ are shown in Table 23. These results show that the predominant method of loss of $C_2N_2$ is not through decomposition to cyanide, but that such decomposition does occur. The replication in percentage conversion is not good, and the extend of conversion to hydrogen cyanide needs further investigation.

TABLE 23

Residues of cyanide in wheat after fumigation with $C_2N_2$

| Added $C_2N_2$ (mg) | Added $C_2N_2$ (mg/kg) | Time after dosing (weeks) | HCN in wheat (mg/kg) | HCN (ratio to $C_2N_2$, W/W) | HCN in germinated wheat (mg/kg) |
|---|---|---|---|---|---|
| 3.64 | 40.6 | 2 | 1.46 | 0.031 | 1.86 |
| 7.67 | 86.2 | 1.5 | 13.2 | 0.13 | 1.5 |

Discussion

Cyanogen is not extensively degraded on wheat to cyanide. Thus, its efficacy is not based on it being a percursor to cyanide. Hydrogen cyanide was not identified in Example 3.

Example 44

Virus Inactivation by a Solution of $C_2N_2$

Aim To assess the virocidal activity of $C_2N_2$.

Introduction

To assess the virocidal activity of $C_2N_2$ we chose to look at two viral-host systems. The first of these involve a nuclear polyhedrosis virus (NPV) and its lepidopteran host, Helicoverpa armigera and the second, a small RNA-containing virus originally isolated from crickets (Cricket Paralysis Virus—CrPV) and a permissive Drosophila melanogster cell line (Scotti, 1972).

Nuclear polyhedrosis viruses (NPV) are large double stranded DNA viruses with circular genomes in the region of 120–150 kilobase pairs. They are one of three groups of insect viruses (the other two being the cytoplasmmic polyhedrosis viruses and the entomopoxviruses) that are characterised by the mature virus particles being embedded in a large pseudo-crystalline protein matrix known as the polyhedral inclusion body (PIB). The PIB is generally upwards of a micron in diameter and can contain from 20 to several hundred virus particles embedded in its protein matrix. Normally, NPVs initiate an infection in their insect host after ingestion of the PIB. In the alkaline conditons of the insect fore-gut the PIB dissolves releasing the virus particles to establish an infection in a susceptible cell (usually basal columnar cells at the apex of the mid-gut). After initial replication the virus goes on to infect a large number of tissues in the insect host which will eventually lead to the death of the host in between 4–8 days (depending on temperature and initial infecting dose).

The small RNA-containing virus Cricket Paralysis Virus (CrPV) was originally isolated from crickets although has been subsequently been isolated from and found to replicate in a wide range of insects species (Christian and Scotti, 1994). In contrast to the NPV, CrPV has a single-stranded RNA genome of around 8 kilobases and encodes only four major structural proteins and a replicase. CrPV has been found to replicate readily in cell lines derived from the vinegar-fly Drosophila melanogaster (Scotti, 1976) and this permissive cell system is routinely used for the estimation of virus titre.

Materials

1) Helicoverpa armigera nuclear polyhedrosis virus (HaNPV) stock suspension at $1.8 \times 10^7$ polyhedral inclusion bodies (PIBs)/ml stored at 4° C.

2) Cricket paralysis virus (CrPV$_{VIC}$/Gm/D2²/Gm/D2²) (*Teleogryllus commodus*, Victoria, Australia) (Christian and Scotti, 1994). Untitred stock stored at −20° C.

3) *Drosophila melanogaster* line 2 (DL2) cells maintained in Schneider's insect medium (Schneider, 1972) supplemented with 10% foetal calf serum.

4) Standard Helicoverpa rearing medium (Shorey and Hale, 1960)—without formalin) dispensed in 4 ml aliquots into J2jelly trays (Nu-trend Containers, Jacksonville, Fla.).

5) NF2 stock solution in double-distilled water, at a final concentration of 2 mg/ml. This was obtained by adding 59 mg of gas to 15 mL of water in an erlenmeyer flask of measured capacity 27.5 mL, and measuring the concentrations in air and water.

7) 5 ml McCartney bottles with neoprene seals. The actual measured capacity was 6.8 mL.

8) Standard 96 well flat-bottomed microtitre plates (Crown Corning, Corning, N.Y.).

9) Heat-sealable Mylar™ (Dupont Australia Ltd., Bayswater, Vic).

Methods

Treatment of Virus Samples

1) Two 100 microliter aliquots of HaNPV or CrPV were dispensed into a five ml McCartney bottle (actual capacity 6.8 mL). To one aliquot was added 900 microliters of double-distilled water (untreated control) and to the second 900 microliters of $C_2N_2$ stock solution (treated sample ). An $C_2N_2$ blank (1 ml of $C_2N_2$ solution) was placed in a fifth bottle.

2) All bottles were tightly sealed and placed at 4° C. overnight (16 hours).

3) Prior to bioassay the concentration of $C_2N_2$ was measured in the gas phase above the samples. The gas was measured on a Varian 3300 Gas Chromatograph, equipped with a thermionic specific detector, after separation on a DBwax column, of internal diameter 0.53 mm. at 60° C.

Bioassay of HaNPV

1) Samples of HaNPV were diluted 1:10 with double distilled water to give a final putative concentration of 1.8×10⁵ PIBs/ml. A dilution series was then made of both the untreated control and treated sample in which the final putative PIB concentrations were 7.2×10⁴, 1.8×10⁴, 7.2×10³, 1.8×10³ and 7.2×10² PIBs/ml.

2) One hundred microliters of each virus dilution was then dispensed into each of twenty five wells of a J2 jelly tray containing 4 ml of standard Helicoverpa rearing diet and the suspension spread of the surface of the diet using a glass rod. The glass rod was sterilised between dilutions by flaming.

3) After airdrying the trays for 15–30 minutes, individual 24 hour old (maintained at 25° C.—mid-first instar) *Helicoverpa armigera* larvae were placed into each well, the well sealed was with heat-sealable Mylar™, the Mylar ™ perforated to allow gas-transfer, and the trays stacked with an intervening layer of wire-gauze.

4) In order to separate the effect on $C_2N_2$ on the virus from its possible effects on the insects, a sample of 25 insects were treated as above but with the ¹⁄₁₀ dilution of the $C_2N_2$ stock solution (Blank) added to the diet before drying and a group of 50 larvae were maintained with not treatment at all.

5) Insects were maintained at 30° C. (70% R.H.) and scored at 3 days post-infection and 10 days post-infection. Larvae dead at 3 days were deemed to have died from causes other than NPV and were excluded from subsequent analysis.

Bioassay of CrPV

1) Cells were subcultured from a confluent monolayer of DL2 cells at a dilution of ¹⁄₁₀₀.

2) Forty microliters of this cell suspension was dispensed into each well of a 96 well microtire plate and the cells allowed to attache for one hour.

3) Samples of CrPV were diluted ¹⁄₁₀ with distilled water and large cell debris removed by centrifugation at 14,000 r.p.m. for 2 minutes in a bench top centrifuge.

4) A ten-fold dilution series of the virus was then made in sterile Schneiders medium supplemented with foetal calf serum and fifty microliters of each dilution aliquotted into each of eight wells of a microtitre plate containing the attached DL2 cells.

5) In addition to the two virus samples (untreated control and treated sample), the $C_2N_2$ blank was also titrated in a similar fashion.

6) Cells were maintained at 27° C. and scored after seven days for the presence on an observable cytopathic effect (C.P.E.).

Results

Measurement of $C_2N_2$

The theoretical amount of $C_2N_2$ added per bottle was 1.8 mg. The partition coefficient was measured at 1.1, that is, the weight of the fumigant in air (per mL) was 1.1 times its weight in water (per mL). The concentration in water was, therefore, approximately 0.25 mg/mL. Thus a mass of 1.8 mg in a 6.8 mL vial resulted, in the system studied, in a theoretical concentration of 0.25 mg/mL in the aqueous phase.

The concentration in the stock solution of $C_2N_2$ was estimated before dosing at 2 mg/mL and measured 2 weeks after dosing, where it was found to be 1.6 mg/mL. The concentrations in a McCartney bottle dedicated to this purpose was also measured by quickly removing the top, sampling with an air tight syringe, and resealing. By this method of analysis the amount of $C_2N_2$ added was only 25% of the theoretical amount, in the case of HaNPV, and 23%, in the case of CrPV. This low recovery is probably due to a combination of both low dosing and a sampling procedure that would underestimate the real amount of gas.

Bioassay of HaNPV

1) Mortality recorded at 10 days in the virus test groups (untreated control and treated sample) are presented in Table 24.

Table 24: Mortality recorded in bioassay of HaNPV treated with (treated sample) or without (untreated control) $C_2N_2$ solution in water. Mortality is expressed as the number of NPV-related deaths/total number insects examined.

| Virus Conc. | Untreated Control Treated Sample |
|---|---|
| 1.8 × 10⁵ | 26/280/24 |
| 7.2 × 10⁴ | 28/310/26 |
| 1.8 × 10⁴ | 12/261/24 |
| 7.2 × 10³ | 8/280/25 |
| 1.8 × 10³ | 2/270/25 |
| 7.2 × 10² | 2/260/25 |

2) Using the data presented in Table 1 a probit analysis was carried out using the computer program POLO. Concentration of virus was expressed as PIBs/mm² (the surface area of diet in each well of the J2tray is 770 mm²). An $LC_{50}$ estimate of 1.960 PIBs/mm² was obtained with upper and lower 95% confidence intervals of 1.094–1.571 PIBs/mm$^2$ respectively for the untreated control. No estimate of LC50 could be obtained from the treated sample.

2) There was no observable differences between the insects kept on diet treated, before drying, with $C_2N_2$ at a concentration of 0.025 mg/mL and those left untreated.

Bioassay of CrPV

1) Titres and standard deviations of virus in the two virus samples were estimated using the method of Reed and Muench (see Davis et. al. 1968).

2) Titres of the two samples were:
Untreated Control 1.38×10$^8$ IU*/ml(+/−4.36×10$^7$)
Treated Sample 2.21×10$^5$IU/ml (+/−6.98×10$^4$)
*IU=infectious units 3) Titration of the $C_2N_2$ blank also revealed that $C_2N_2$ had a strong cytotocity to DL2 cells at a concentration of 0.4 mg/mL of water, but at a concentration of one tenth this amount there was no observable effect.

Discussion

Inactivation of HaNPV by $C_2N_2$ in Solution

1) From the data presented it would appear that $C_2N_2$ in solution at a final concentration of 0.25 mg/mL inactivates HaNPV by at least 240 fold after 16 hours at 40° C. i.e. the highest putative virus concentration in the treated sample (1.8×10$^5$ PIBs/ml) fails to produce the mortality observed in the lowest concentration (7.2×10$^2$PIBs/ml) of the untreated control.

Inactivation of CrPV

1) The data presented above demonstrate that $C_2N_2$ in solution at a concentration of 0.25 mg/mL inactivates CrPV 640-fold after treatment overnight at 4° C.

Discussion

The ability to control viruses is of major importance in a large number of areas pertaining to medical, dental, veterinary and scientific premises and equipment. This control of viruses is in addition to control of bacteria (Example 19), control of moulds (Example 21) and fungal diseases (Example 41). The ability to move through water (Example 22), and its activity in both the vapour phase and in solution, is an important and novel aspect of control of viruses, bacteria and other organisms important for human and animal health.

Example 45

Effect of Oxygen at Various Concentrations and the Effect of Carbon Dioxide at Various Pressures on the Toxicity of $C_2N_2$ Aim: To determine the effect of different concentrations of oxygen and different pressures of carbon dioxide on the toxicity of $C_2N_2$.

Materials and Methods

Fumigations were carried out in stainless steel cylinders as described in Example 39. Adults of *Sitophilus oryzae* were treated with $C_2N_2$ in stainless steel vessels where the oxygen level was adjusted to 60%, 20% or 10%. Similarly adults of *Sitophilus oryzae* were treated with $C_2N_2$ in the presence of 50% and 30% carbon dioxide at one atmosphere above ambient, and also in 30% carbon dioxide at atmospheric pressure. End point mortalities were determined after 24 h exposure to a given amount of $C_2N_2$.

Mixed age adults were taken from laboratory cultures of *Sitophilus oryzae* (Strain LS2) and placed, 20 to a container, in small glass tubes (25 mm diam. 25 mm) capped both ends by fine stainless steel mesh. Three containers were placed in a stainless steel cylinder which was then closed. The different oxygen levels were obtained by pressurising the stainless steel cylinder with a cylinder of oxygen or nitrogen until the required oxygen ratio was obtained and then allowing the pressure to return to atmospheric by releasing gas to the atmosphere. Carbon dioxide levels were obtained in a similar fashion. When loading or unloading the cylinders, all pressure changes were carried out over at least one minute in order to avoid insect damage resulting from rapid pressure change (Ulrichs, 1994; Nakakita and Kawashima, 1994). The absolute amount of $C_2N_2$ used was either 0.94, 0.4, 0.2 or 0.1 mg per liter. A control was kept for each treatment cylinder. After 24 h fumigation the fumigant concentration in the cylinders was checked by gas chromatography, the insects were removed from the treatment and control cylinders and survivors were counted. The insects were kept until end-point mortalities could be determined.

Results

The results are shown in Tables 25 and 26. Lowering the oxygen level below normal levels (but still above the levels where anoxia might be expected) had little or no effect on the toxicity of $C_2N_2$. However there was evidence to suggest that high oxygen levels reduce the toxicity of low levels of $C_2N_2$ (Table 25).

The presence of increased levels of carbon dioxide was found to enhance the toxicity of $C_2N_2$. With 30% carbon dioxide at 1 atmosphere above ambient, a mortality of 75% was obtained. This increased to 100% in the presence of only 0.1 mg/L of $C_2N_2$ (Table 26).

Discussion

The toxicity of $C_2N_2$ is reduced by levels of oxygen above ambient but is not affected by lower oxygen levels (presuming the oxygen level is above the level where anoxia can occur). Carbon dioxide enhances the toxicity of $C_2N_2$ (see example 2) and the effect is further enhanced by increased pressure (cf example 39). The use of carbon dioxide and increased pressures may be pertinent to the treatment of high value commodities in pressurised fumigation chambers.

TABLE 25

Relationships between mortality, concentration and Oxygen level in $C_2N_2$ fumigation of *Sitophilus oryzae*

| dose/container | Mortality (%) | | |
| --- | --- | --- | --- |
| | 60% $O_2$ | 20% $O_2$ | 10% $O_2$ |
| 0.94 mg/L | | 100% | |
| 0.4 mg/L | 100% | 93% | 100% |
| 0.2 mg/L | 3% | 53% | 47% |
| 0.1 mg/L | | 0% | 0% |

TABLE 26

Relationships between mortality, concentration and carbon dioxide pressure in $C_2N_2$ fumigation of *Sitophilus oryzae*

| dose/container | Mortality (%) | | | |
|---|---|---|---|---|
| | 50% $CO_2$ | 30% $CO_2$ | 30% $CO_2$ | normal |
| 0.94 mg/L | | | | 100% |
| 0.4 mg/L | | | | 93% |
| 0.2 mg/L | 100% | 100% | | 53% |
| 0.1 mg/L | | 100% | 100% | 0% |
| 0 mg/L | | 75% | | |

Example 46

$C_2N_2$ as a Fumigant for Use on Cut Flowers, and Related Uses

Aim: To assess the ability of $C_2N_2$ to act as a fumigant against insects commonly found on cut flowers.

Materials and Methods

Insects were collected from freshly cut flowers (Protea and Thryptomene) and placed into glass vials (approximate capacity 8 mL) and sealed with lids containing a septum. Vials with representative samples of each insect order were kept as controls and the remainder were dosed with 1 mL of $C_2N_2$ of a concentration of 92 $mgL^{-1}$ giving a final concentration of approximately 11.5 $mgL^{-1}$. These vials were left at ambient temperature (approximately 18° C.) for 2 hours. After that time had elapsed the insects were checked for signs of life then aired and preserved for further identification.

Results

The control vials showed no mortality over the two hour period whilst all of the insects, mites and spiders exposed to $C_2N_2$ were dead after the two hour exposure.

| | Insect | | | |
|---|---|---|---|---|
| (Common Name) | (Order) | (Family) | No. Alive | No. Dead |
| Thrips | Thysanoptera | phaelothripida | 0 | 15 |
| Leaf beetle | Coleoptera | chrysomalidae | 0 | 1 |
| Springtails | Colembola | | 0 | 10 |
| Moths | Lepidoptera | geometridae | 0 | 2 |
| Moth (larva) | | | 0 | 1 |
| Mites | Acarina | | 0 | 8 |
| Spiders | Arachnida | | 0 | 6 |
| Flies | Diptera | sciaridae | 0 | 6 |

Discussion

These preliminary results indicate that $C_2N_2$ will kill these insects, spiders and mites commonly found on cut flowers, growing plants and elsewhere. Insects controlled were from the orders Thysanoptera, Coleoptera, Colembola, Lepidoptera and Diptera. Other major orders killed were Aracina (mites) and Aracnida (spiders). Cross reference is made to control of Coleoptera (e.g. Example 30, Example 34), Lepidoptera (Example 27), Diptera (Example 12) and Acarina (Example 40).

Example 47

Mortality of *Dacus tyroni* (Queensland Fruit Fly) Eggs Treated with $C_2N_2$

Aim: To determine the toxicity of $C_2N_2$ when dissolved in an aqueous solution to a Dipteran species, *Dacus tyroni* (Queensland fruit fly) eggs and to measure gas concentrations over the exposure period to obtain a concentration× time relationship.

Materials and Methods

*D. tyroni* eggs were treated at 25° C. for 2 hours in duplicate with seven different concentrations, including a flask control, of $C_2N_2$ dissolved in a 0.01 M solution of hydrochloric acid (HCl). 10 mL of 0.01 M HCl was places into seven 16 mL vials fitted with Miniert gastight valves and either 0, 0.45, 4.5, 9.0, 18.0, 27.0 or 36.0 mL of 72% pure $C_2N_2$ gas was injected very slowly into each vial. This corresponded to 0, 68, 684, 1369, 2738, 4106 and 5475 $mgL^{-1}$ $C_2N_2$ in solution respectively. Approximately 200 (±10) one day old eggs were placed onto 14 moistened 7×1 cm strips of filter paper and the paper attached with tape to 14, 11×1 cm strips of stainless steel. Each strip was then placed in a 275 mL Erlenmeyer flask fitted with a ground glass septum sealed top. 0.1 mL of each of the $C_2N_2$ solutions was introduced into two flasks using a Precision Sampling Corp. liquid syringe, taking care to avoid touching the eggs with the solution. This corresponded to a concentration of approximately 0, 0.025, 0.25, 0.5, 1.0, 1.5, 2.0 $mgL^{-1}$ $C_2N_2$ gas in duplicate flasks. An additional laboratory control in duplicate was kept on moistened filter paper on petri dish filled with rearing medium (dried carrots, torula yeast, Nipagin, HCl and water) and held in a controlled temperature (CT) room at 25° C. and 59% r.h. for the duration of the exposure period.

$C_2N_2$ gas concentrations in the headspace of each of the flasks were measured on a Varian gas chromatograph fitted with a thermionic specific detector and a DBwax megabore column. Column temperature was set at 60° C., injector temperature at 100° C. and the detector at 288° C. Concentrations were calculated using three standards of 0.25, 0.4 and 1.51 $mgL^{-1}$ $C_2n_2$ made in 1.2 L Erlenmeyer flasks. Concentration×time (CT products for each of the samples were calculated from the results.

After 2 hours of exposure to the gas the flasks were aired in a fumehood and the paper strips holding the eggs were placed on moistened 7 cm circles of filter paper in petri dishes containing culturing medium. They were then kept at 25° C. and 59% r.h. Assessment of mortality was made by counting the number of eggs remaining each day for 6 days.

Results

Concentrations, measured CT products and percent mortality for each of the samples are recorded in Table 27. Mortality was calculated by comparing the number of unhatched eggs in the samples to the number in the controls (Table 28). Flask and laboratory controls had an average of 33 of 200 eggs unhatched, so the total number of eggs treated was reduced to 167 to account for this. Samples 1 to 4 showed a greater hatching rate than the controls (an average of 183 for 0.025 $mgL^{-1}$ and 186 for 0.25 $mgL^{-1}$) which could indicate that a low $C_2N_2$ concentrations the fumigant could have a beneficial effect. These samples were assumed to have 100% survival. Complete mortality was achieved at concentrations greater than 1.5 $mgL^{-1}$ for two hours (CT product of 2.1 mg h $L^{-1}$), greater than 73% mortality at 1.0 $mgL^{-1}$ (CT product of 1.4 mg h $L^{-1}$), 5% mortality at 0.5 $mgL^{-1}$ (CT product of 0.8 mg h $L^{-1}$) and no mortality at 0.25 $mgL^{-1}$ or below (CT product of 0.38 mg h $L^{-1}$).

In addition, at 1.0 $mgL^{-1}$ hatching was delayed for 24 hours as compared to controls and lower concentrations.

TABLE 27

$C_2N_2$ concentration, CT product and percent mortality of samples containing 200 *D. tyroni* eggs dosed for 2 hours

| sample | concentration (mgL-1) | measured product (mg h L$^{-1}$) | mortality (%) |
|---|---|---|---|
| 1 | 0.025 | 0.043 | 0 |
| 2 | 0.025 | 0.043 | 0 |
| 3 | 0.25 | 0.393 | 0 |
| 4 | 0.25 | 0.368 | 0 |
| 5 | 0.5 | 0.822 | 4 |
| 6 | 0.5 | 0.809 | 5 |
| 7 | 1.0 | 1.429 | 91 |
| 8 | 1.0 | 1.393 | 73 |
| 9 | 1.5 | 2.009 | 100 |
| 10 | 1.5 | 2.161 | 100 |
| 11 | 2.0 | 2.811 | 100 |
| 12 | 2.0 | 2.667 | 100 |
| 13 | flask control | — | — |
| 14 | flask control | — | — |
| 15 | lab control | — | — |
| 16 | lab control | — | — |

Discussion

Complete mortality of *D. tyroni* eggs was achieved at fumigant concentrations greater than 1.5 mgL$^{-1}$ for 2 hours or 2.1 mg h L$^{-1}$. This result is similar to that outlined in Example 12, for control of larvae of this species. From these results, the following conclusions can be made:

$C_2N_2$ is effective when applied in an aqueous solution. The relevant chemistry of the phase distribution is discussed in Example 22 and Example 31.

$C_2N_2$ is effective against eggs, as well as against other stages, as also shown in Example 34.

TABLE 28

Counts of unhatched eggs of *D. tyroni* treated with $C_2N_2$ solution over a six day assessment period Number of unhatched eggs from total of 200

| sample | Day 1 | Day 2 | Day 3 | Day 4 | Day 5 | Day 6 |
|---|---|---|---|---|---|---|
| 1 | 19 | 19 | 19 | 19 | 19 | 19 |
| 2 | 17 | 16 | 15 | 15 | 15 | 15 |
| 3 | 38 | 23 | 23 | 23 | 21 | 21 |
| 4 | 31 | 27 | 27 | 27 | 27 | 27 |
| 5 | 40 | 40 | 40 | 40 | 40 | 40 |
| 6 | 49 | 49 | 48 | 46 | 42 | 42 |
| 7 | 193 | 188 | 185 | 185 | 185 | 185 |
| 8 | 195 | 164 | 155 | 155 | 155 | 155 |
| 9 | 204 | 204 | 204 | 204 | 204 | 204 |
| 10 | 207 | 207 | 207 | 207 | 207 | 207 |
| 11 | 207 | 207 | 207 | 207 | 207 | 207 |
| 12 | 204 | 204 | 204 | 204 | 204 | 204 |
| 13 | 33 | 33 | 33 | 33 | 33 | 33 |
| 14 | 27 | 26 | 26 | 26 | 26 | 26 |
| 5 | 33 | 33 | 33 | 33 | 33 | 33 |
| 16 | 39 | 39 | 39 | 39 | 39 | 39 |

Example 48

Properties of $C_2N_2$ as a Systemic Pesticide

Aim: To determine whether $C_2N_2$ can be applied systemically to plants through the application of an aqueous solution of the fumigant.

Materials and Methods

Freesia and Cineria seedlings purchased from a local nursery were transplanted from punnets to glass jars (60 mL) and the soil surface sealed with melted paraffin wax. Two jars of soil from discarded plants were also sealed with wax.

An aqueous solution of $C_2N_2$ was made by bubbling 10 ml of 84% $C_2N_2$ into 60 mL of tap water. Each plant and the soil in the glass jars were watered with 5 mL of this aqueous solution. This was achieved by injecting it through the wax layer into the soil of each jar, then resealing the puncture hole with the addition of more melted wax. Each test was placed inside a 525 mL glass jar and sealed with a screw top lid fitted with a septum. Two empty 525 mL jars were injected directly with 5 ml of the aqueous $C_2N_2$ solution.

the concentration of $C_2N_2$ in the head space was determined on a Varian 3300 Gas Chromatograph, equipped with a thermionic specific detector, after separation on a DBwax column (0.53 mm diameter).

Figure 47:
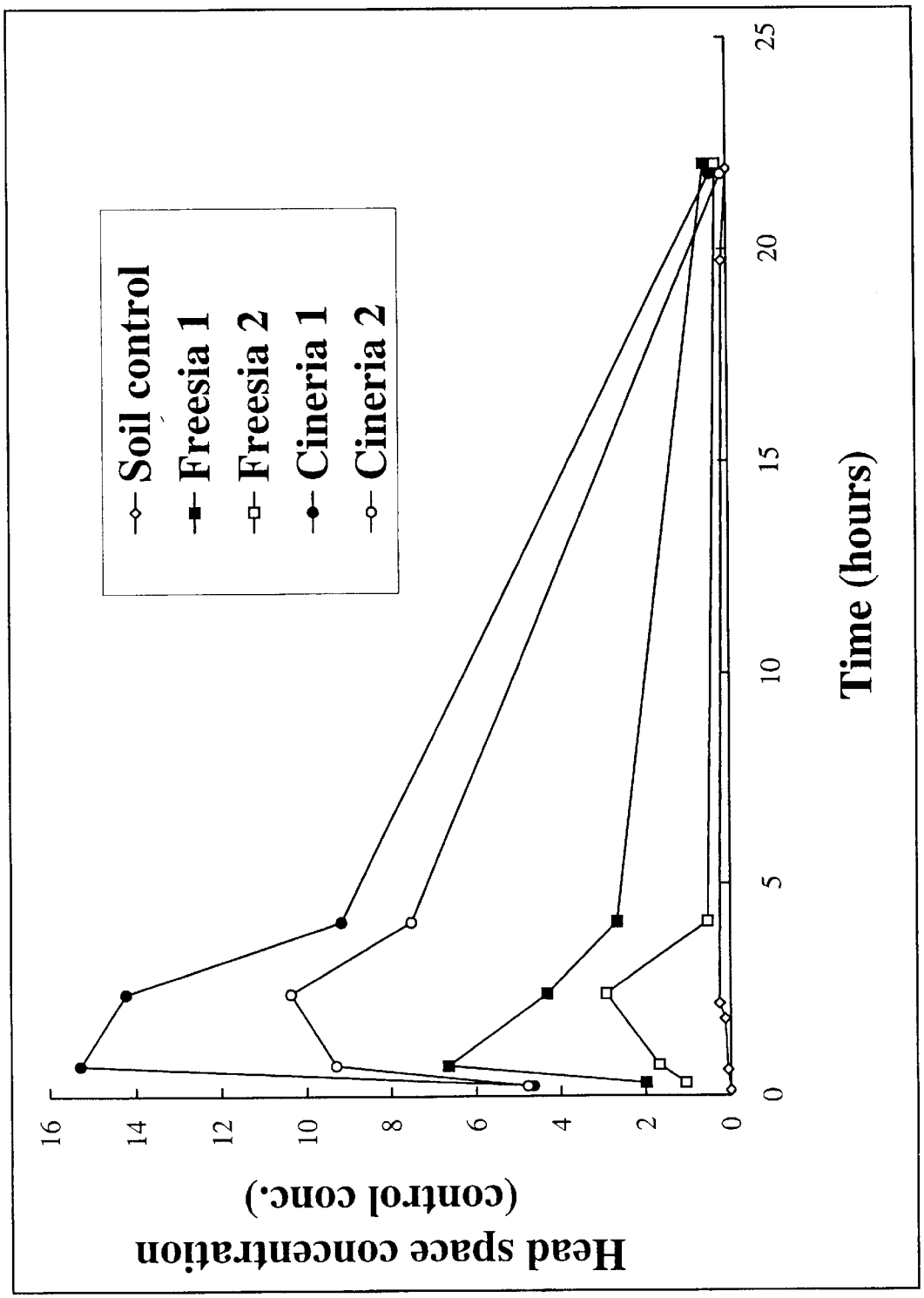
FIG. 47 illustrates the systemic transport of $C_2N_2$ from the soil to the headspace of test plants.

The concentration of $C_2N_2$ in the head space of each test was been expressed as a percentage of the concentration in the headspace of the control jars ($C_2N_2$ aqueous solution added to an empty jar). FIG. 47 indicates that the plants are transporting $C_2N_2$ from the soil to the head space. The soil control (wax sealed over soil) indicates that the wax seal is relatively impermeable to $C_2N_2$, therefore the amount of $C_2N_2$ in the head space can be attributed to the systemic transport of $C_2N_2$ by the plants.

After 24 hours the foilage was removed and weighed then placed in an 8 mL vial with with a septa fitted screw top lid. The amount of $C_2N_2$ was assessed by adding 2 mL of Tetrahydrofuran to each vial then measuring the concentration of $C_2N_2$ in the head space. For comparison, 5 microliter of 84% $C_2N_2$ was added to 2 mL Tetrahydrofuran in an 8 mL vial. The amount of fumigant detected in the foilage is listed below.

| Test | Weight of Foliage (gm) | Total Amount NF2 ($\mu$g) |
|---|---|---|
| Freesia 1 | 1.50 | 1.8 |
| Cineria 1 | 1.62 | 1.8 |
| Freesia 2 | 1.38 | 0 |
| Cineria 2 | 1.51 | 1.5 |
| Freesia Control | 0.80 | 0 |
| Cineria Control | 1.63 | 0 |

No effect of the fumigant on the quality of the plants was observed.

Discussion $C_2N_2$ is systemic in plants, as shown by the amount transported into the headspace and the detection of the chemical in the foilage.rticultural industry. This systemic activity is important for control of insects and plant diseases. Cross reference is made to Example 22, on the movement of $C_2N_2$ through water.

Example 49

Comparative Behaviour of $C_2N_2$ Phosphine and Methyl Bromide on Wheat

Aim: To compare the sorption and desorption of $C_2N_2$, phosphine and methyl bromide on wheat.

Introduction

Fumigants are absorbed by fumigants during the fumigation process. Following the treatment, fumigant can desorb from the commodity. This has implications for the treatment and safe handling of fumigants and fumigated commodities.

Materials and Methods

Samples of wheat (25 g) were placed in 250 mL conical flasks of known volume. The flasks were stoppered with a gas tight stopper containing a rubber septum (injection port). Flasks were dosed with $C_2N_2$ (10 mg/L), phosphine (2 mg/L) or methyl bromide (32 mg/L). After 24 h the headspace concentrations were determined by gas chromatography. Each flask was then opened and the wheat sample aired briefly by pouring the wheat from one container to another and then the remaining sorbed fumigant was estimated by grinding the wheat sample in a gas-tight Waring blender canister fitted was a sampling port and and determining the released fumigant by head space analysis.

Results

In the headspace after 24 h there was 91% of the initial phosphine remaining, 69% of the methyl bromide and 10% of the $C_2N_2$, gas chromatography showed that 3% of the original $C_2N_2$ had been converted to HCN. The amounts of recoverable fumigant in the wheat samples were found top be 11.78 ppm (w/w) methyl bromide, 0.48 ppm (w/w) $C_2N_2$ and 0.05 ppm (w/w) phosphine. With the recovered $C_2N_2$ there was approximately 1 ppm HCN.

Discussion

The doses used correspond to the recommended or the likely effective amount for the effective fumigation of wheat. The results indicate that the amount of $C_2N_2$ which can desorb from a freshly fumigated grain sample is not likely to present special problems in the safe handling of fumigated commodities (cf Example 3). That is the normal safety precautions associated with fumigation practice are sufficient. Of the total amount of $C_2N_2$ added (approx 2500 ug), the amount in the wheat was 10 ug $C_2N_2$ and 20 ug HCN, indicating that conversion to HCN is a minor metaolic pathway.

Experimental work with the fumigant and its gaseous and liquid formulations has shown that these fumigants can be used as an insecticide, a fungicide, a bactericide, a herbicide, a nematicide, a viruscide and as a mould inhibitor, the last particularly use for wet grain. As a sterilising agent cyanogen is a suitable replacement, in some applications, for ethylene oxide and other chemicals used for sterilising in hospitals and dental and veterinary premises. The fumigants of the present invention are also useful for treating timber and timber products, soil, plants and cut flowers. The present invention is useful in the fumigation of stored grain, nuts and other stored particulate foodstuffs, plants, fruits and vegetables and meat.

We claim:

1. A fumigant comprising cyanogen ($C_2N_2$) essentially free from hydrogen cyanide and other cyanogenic compounds, in solution or in association with carrier gas, wherein the concentration of cyanogen is in the range from 0.01 mg $L^{-1}$ to about 160 mg $L^{-1}$.

2. A fumigant as claimed in claim 1, wherein said carrier gas is an inert gas.

3. A fumigant as claimed in claim 1, wherein said carrier gas contains carbon dioxide.

4. A fumigant as claimed in claim 1, wherein said fumigant is in solution.

5. The fumigant of claim 1, wherein solution is an aqueous solution.

6. A method fumigation, comprising applying a fumigant comprising cyanogen ($C_2N_2$) essentially free from hydrogen cyanide and other cyanogenic compounds, in the gaseous form to a commodity or structure, wherein the concentration of cyanogen is in the range from 0.01 mg $L^{-1}$ to about 160 mg $L^{-1}$, or applying a fumigant comprising cyanogen in an aqueous solution to a commodity or structure, such that the cyanogen concentration, if averaged over the volume of the commodity or structure, would be in the range from 0.01 mg $L^{-1}$ to about 160 mg $L^{-1}$.

7. A method of fumigation as claimed in claim 6, wherein said commodity is selected from the group consisting of grain, seed, meat, fruit, vegetables, timber, plants, cut flowers, and soil.

8. A method of fumigation as claimed in claim 6, wherein said structure is a silo, a structure containing bulk grain or a room, premises or appliance useful for dental, medical, scientific or veterinary applications.

9. A method of fumigation as claimed in claim 6, wherein said fumigant is able to control one or more biota.

10. A method of fumigation as claimed in claim 6, wherein said fumigant either comprises carbon dioxide ($CO_2$), or is applied in an environment containing carbon dioxide ($CO_2$), or both.

11. A method of fumigation as claimed in claim 6, wherein either the humidity or pressure or both, within an environment within which said fumigant is applied, is adjusted to control the characteristics of said fumigant.

12. A method of fumigation as claimed in claim 6, wherein said fumigation includes low flow gaseous fumigation, low pressure gaseous fumigation, high pressure gaseous fumigation, spraying of a liquid fumigant, or soaking of a commodity in a liquid fumigant.

13. A method of fumigation as claimed in claim 8, wherein said structure is a structure containing wheat.

14. A method of fumigation as claimed in claim 9, wherein said biota is selected from the group consisting of viruses, insects, spiders, nematodes, mites, bacteria, molds, fungi and their spores, and rodents.

15. A method of fumigation as claimed in claim 11, wherein said characteristics of said fumigant are selected from the group consisting of increased toxicity and synergistic effects.

* * * * *